(12) United States Patent
Paterson et al.

(10) Patent No.: US 8,956,621 B2
(45) Date of Patent: Feb. 17, 2015

(54) COMPOSITIONS AND METHODS FOR TREATMENT OF CERVICAL DYSPLASIA

(75) Inventors: Yvonne Paterson, Philadelphia, PA (US); John Rothman, Lebanon, NJ (US)

(73) Assignees: The Trustees of the University of Pennsylvania, Philadelphia, PA (US); Advaxis, Inc., Princeton, NJ (US)

(*) Notice: Subject to any disclaimer, the term of this patent is extended or adjusted under 35 U.S.C. 154(b) by 348 days.

(21) Appl. No.: 13/314,583

(22) Filed: Dec. 8, 2011

(65) Prior Publication Data

US 2012/0177678 A1 Jul. 12, 2012

Related U.S. Application Data

(63) Continuation-in-part of application No. 11/715,497, filed on Mar. 8, 2007, now Pat. No. 8,114,414, which is a continuation-in-part of application No. 11/415,271, filed on May 2, 2006, now Pat. No. 8,791,237, which is a continuation-in-part of application No. 11/373,528, filed on Mar. 13, 2006, now Pat. No. 7,662,396, which is a continuation-in-part of application No. 10/835,662, filed on Apr. 30, 2004, now Pat. No. 7,588,930, which is a continuation-in-part of application No. 10/239,703, filed as application No. PCT/US01/09736 on Mar. 26, 2001, now Pat. No. 7,635,479, said application No. 11/415,271 is a continuation-in-part of application No. 11/223,945, filed on Sep. 13, 2005, now Pat. No. 7,820,180, which is a continuation-in-part of application No. 10/949,667, filed on Sep. 24, 2004, now Pat. No. 7,794,729.

(51) Int. Cl.
| | | |
|---|---|---|
| *A61K 39/12* | (2006.01) | |
| *A61P 35/00* | (2006.01) | |
| *A61K 39/00* | (2006.01) | |
| *C07K 14/195* | (2006.01) | |
| *C07K 14/705* | (2006.01) | |

(52) U.S. Cl.
CPC .............. *A61K 39/0011* (2013.01); *A61K 39/12* (2013.01); *C07K 14/195* (2013.01); *C07K 14/70503* (2013.01); *A61K 39/00* (2013.01); *A61K 2039/523* (2013.01); *A61K 2039/53* (2013.01); *C07K 2319/00* (2013.01)
USPC ..................... 424/190.1; 424/192.1; 530/350; 536/23.1

(58) Field of Classification Search
None
See application file for complete search history.

(56) References Cited

U.S. PATENT DOCUMENTS

| | | | |
|---|---|---|---|
| 4,521,382 A | 6/1985 | Kessick | |
| 4,567,041 A | 1/1986 | Likhite | |
| 4,777,239 A | 10/1988 | Schoolnik et al. | |
| 4,816,253 A | 3/1989 | Likhite | |
| 4,879,213 A | 11/1989 | Fox et al. | |
| 5,262,177 A | 11/1993 | Brown et al. | |
| 5,342,774 A | 8/1994 | Boon et al. | |
| 5,369,008 A | 11/1994 | Arlinghaus et al. | |
| 5,643,599 A | 7/1997 | Lee et al. | |
| 5,679,356 A | 10/1997 | Bonnem et al. | |
| 5,681,570 A | 10/1997 | Yang et al. | |
| 5,719,054 A * | 2/1998 | Boursnell et al. | .......... 435/320.1 |
| 5,728,399 A | 3/1998 | Wu et al. | |
| 5,824,538 A | 10/1998 | Branstrom et al. | |
| 5,830,702 A * | 11/1998 | Portnoy et al. | ............... 435/69.3 |
| 5,858,682 A | 1/1999 | Gruenwald et al. | |
| 5,876,735 A | 3/1999 | Reed | |
| 5,877,159 A | 3/1999 | Powell et al. | |
| 6,015,567 A | 1/2000 | Hudziak et al. | |
| 6,051,237 A | 4/2000 | Paterson et al. | |
| 6,306,404 B1 | 10/2001 | LaPosta et al. | |
| 6,333,169 B1 | 12/2001 | Hudziak et al. | |
| 6,479,258 B1 | 11/2002 | Short | |
| 6,521,449 B1 | 2/2003 | Polack et al. | |
| 6,565,852 B1 | 5/2003 | Paterson | |
| 6,767,542 B2 | 7/2004 | Paterson et al. | |
| 6,855,320 B2 | 2/2005 | Paterson | |
| 7,135,188 B2 | 11/2006 | Paterson | |
| 7,217,419 B2 * | 5/2007 | Wettendorff | ............... 424/204.1 |
| 7,488,490 B2 | 2/2009 | Davis et al. | |
| 2003/0028206 A1 | 2/2003 | Shiber | |
| 2003/0202985 A1 | 10/2003 | Paterson | |
| 2003/0220239 A1 | 11/2003 | Simard et al. | |

(Continued)

FOREIGN PATENT DOCUMENTS

| | | |
|---|---|---|
| EP | 0 902 086 | 3/1999 |
| JP | 63-173594 | 7/1988 |

(Continued)

OTHER PUBLICATIONS

Gene Bank Accession No. AA 435505 (1999, p. 1-4).*

(Continued)

*Primary Examiner* — Agnieszka Boesen
(74) *Attorney, Agent, or Firm* — Mark S. Cohen; Pearl Cohen; Zedek Latzer Baratz LLP

(57) ABSTRACT

The present invention provides methods of treating, protecting against, and inducing an immune response against cervical dysplasia and cancer, comprising the step of administering to a subject a recombinant *Listeria* strain, comprising a fusion peptide that comprises an LLO fragment and an E7 and/or E6 antigen. The present invention also provides methods for inducing an anti-E7 CTL response in a human subject and treating HPV-mediated diseases, disorders, and symptoms, comprising administration of the recombinant *Listeria* strain.

26 Claims, 29 Drawing Sheets

(56) References Cited

U.S. PATENT DOCUMENTS

| | | | |
|---|---|---|---|
| 2004/0228877 | A1 | 11/2004 | Dubensky et al. |
| 2005/0118184 | A1 | 6/2005 | Paterson et al. |
| 2005/0129715 | A1 | 6/2005 | Paterson et al. |
| 2006/0051380 | A1 | 3/2006 | Schulick et al. |
| 2006/0093582 | A1 | 5/2006 | Paterson et al. |
| 2006/0104991 | A1 | 5/2006 | Paterson et al. |
| 2006/0121053 | A1 | 6/2006 | Sweeney et al. |
| 2006/0205067 | A1 | 9/2006 | Paterson et al. |
| 2006/0210540 | A1 | 9/2006 | Paterson et al. |
| 2006/0223835 | A1 | 10/2006 | Liotta et al. |
| 2006/0269561 | A1 | 11/2006 | Paterson et al. |
| 2008/0124354 | A1 | 5/2008 | Paterson et al. |

FOREIGN PATENT DOCUMENTS

| | | |
|---|---|---|
| WO | WO 90/12594 | 11/1990 |
| WO | WO 92/20356 | 11/1992 |
| WO | WO 93/15212 | 8/1993 |
| WO | WO 94/17192 | 8/1994 |
| WO | WO 96/14087 | 5/1996 |
| WO | WO 96/34631 | 11/1996 |
| WO | WO 98/48026 | 10/1998 |
| WO | WO 99/06544 | 2/1999 |
| WO | WO 99/07861 | 2/1999 |
| WO | WO 99/10496 | 3/1999 |
| WO | WO 99/25376 | 5/1999 |
| WO | WO 01/27295 | 4/2001 |
| WO | WO 01/72329 | 10/2001 |
| WO | WO 03/015716 | 2/2003 |
| WO | WO 03/092600 | 11/2003 |
| WO | WO 2004/006837 | 1/2004 |
| WO | WO 2006/017856 | 2/2006 |
| WO | WO 2006/036550 | 4/2006 |
| WO | WO 2007/061848 | 5/2007 |
| WO | WO 2007/106476 | 9/2007 |
| WO | WO 2007/130455 | 11/2007 |

OTHER PUBLICATIONS

Sewell et al. (Archives in Otolaryngology, Head, Neck Surgery, vol. 130, Jan. 2004).*
Abachin et al., "Formation of D-alanyl-lipoteichoic acid is required for adhesion and virulence of *Listeria monocytogenes*", Molecular Microbiology, 2002, 43(1), 1-14.
Aggarwal et al., "Oral Salmonella: Malaria Circumsporozoite Recombinants Induce Specific CD8+ Cytotoxic T Cells", J. Exp. Med. 1990, 172, 1083-1090.
Alexander et al., "Characterization of an aromatic amino acid-dependent listeria monocytogenes mutant: attenuation, persistance, and ability to induce protective immunity in mice", infection and immunity, May 1993, p. 2245-2248.
Amici et al., "DNA vaccination with full-length or truncated Neu induces protective immunity against the development of spontaneous mammary tumors in HER-2/neu transgenic mice", Gene Therapy, 2000, 7, 703-706.
Angelov et al., "Therapeutic vaccine for acute and chronic motor neuron diseases: Implications for amyotrophic lateral sclerosis", PNAS, Apr. 2003, vol. 100, No. 8, 4790-4795.
Anido et al., "Biosynthesis of tumorigenic HER2 C-terminal fragments by alternative initiation of translation", The EMBO Journal, 2006, 25, 3234-3244.
Bai et al., "Antigenic drift as a mechanism for tumor evasion of destruction by cytplytic T lymphocytes", J. Clin. Invest., 2003, 111, 1487-1496.
Bast et al., "Antitumor activity of bacterial infection, I. Effect of listeria monocytogenes on growth of a murine fibrosarcoma", J. Natl. Cancer Inst., 54:749-756, 1975.
Baxeranis et al., "Immunobiology of HER-2/neu oncoprotein and its potential application in cancer immunotherapy", Cancer Immunol. Immunother., 2004, 53, 166-175.
Beattie et al., "Cloning and characterization of T-cell-reactive protein antigens from Listeria monocytogenes", Infect. Immun., Sep. 1990; 58(9):2792-803.

Beatty, "A dual role for IFN-gamma in resolving the balance between tumor progression and regression", University of Pennsylvania, 2001, ii-xiii, pp. 1-10, AAT 9989567, UMI No. 9989567, Bell and Howell Information and Learning Company, Ann Arbor, Michigan.
Bergmann et al., "The neu oncogene encodes an epidermal growth factor receptor-related protein", Nature, vol. 319, Jan. 1986, 226-230.
Biragyn et al., "Models for Lymphoma", Current Protocols in Immunology, 2001, 20.6.1-20.6.30.
Boon et al., "Tumor Antigens Recognized by T Lymphocytes", Annu. Rev. Immunol. 1994,12, 337-365.
Bouwer et al., "Acquired immunity to an intracellular pathogen: immunologic recognition of L. monocytogenes-infected cells", Aug. 1997;158:137-46.
Bouwer et al., "Cytotoxic-T-lymphocyte responses to epitopes of listeriolysin O and p60 following infection with Listeria monocytogenes", Infect. Immun., Jul. 1996; 64(7):2515-22.
Bowie et al., "Deciphering the message in protein sequences: tolerance to amino acid substitutions", Science 247:1306-1310, 1990.
Bron et al., "Use of the alr gene as a food-grade selection marker in lactic acid bacteria", Applied and Environmental Microbiology, Nov. 2002, vol. 68, No. 11, p. 5663-5670.
Bruder et al., "Efficient induction of cytotoxic CD8+ T cells against exogenous proteins: establishment and charcterization of a T cell line specific for the membrane protein ActA of *Listeria monocytogenes*", Eur. J. Immunol., Sep. 1998, 28(9):2630-9.
Brunner et al., "Quantitative assay of the lytic action of immune lymphoid cells on cr-labelled allogeneic target cells in vitro; inhibition by isoantibody and by drugs", Immunology, 1968, 14, 181-196.
Camilli et al., "*Listeria monocytogenes* mutants lacking phosphatidylinositol-specific phospholipase C are avirulent", J. Exp. Med., vol. 173, 751-754, Mar. 1991.
Catic et al., "Introduction of protein or DNA delivered via recombinant *Salmonella typhimurium* into the major histocompatibility complex class I pesentation pathway of macrophages", Microbes Infect., Feb. 1999, 1(2):113-21.
Chazin et al., "Transformation mediated by the human HER-2 gene independent of the epidermal growth factor receptor", Oncogene, 1992, 7, 1859-1866.
Cheever et al., "T-Cell Immunity to Oncogeneic Proteins Including Mutated RAS and Chimeric BCR-ABL", Ann. N.Y. Acad. Sci. 1993, 690:101-112.
Chen et al., "DNA Vaccines Encoding Full-Length or Truncated Neu Induce Protective Immunity against Neu-expressing Mammary Tumors", Cancer Research 58, 1965-1971, May 1, 1998.
Cho et al., "Structure of the extracellular region of HER2 alone and in complex with the herceptin Fab", Nature, vol. 421, Feb. 2003, 756-760.
Ciurea et al., "Viral persistence in vivo through selection of neutralizing antibody-escape variants", PNAS, Mar. 2000, vol. 97, No. 6, 2749-2754.
Cohen, J. "Cancer vaccines get a shot in the arm", Science 262:841-843.
Concetti et al., "Autoantibody to P185$^{erbB2/neu}$ oncoprotein by vaccination with xenogenic DNA", Cancer Immunol. Immunother., 1996, 43, 307-315.
Coussens et al., "Tyrosine kinase receptor with extansive homology to EGF receptor shares chromosomal location with neu oncogene", Sceince, vol. 230, 1132-1139, Dec. 1985.
Darji et al., "Antigen-specific T cell receptor antagonism by antigen-presenting cells treated with the hemolysin of *Lestria monocytogenes*: a novel type of immune escape", Eur. J. Immunol., Jul. 1997; 27(7):1696-703.
Darji et al., "T-cell anergy induced by antigen presenting cells treated with the hemolysin of *Listeria monocytogenes*", Immunol. Lett., Jun. 1997; 57(1-3):33-7.
Darji et al., "The role of the bacterial membrane protein ActA in immunity and protection against *Listeria monocytogenes*", J. Immunol., Sep. 1, 1998; 161(5):2414-20.
Di Carlo et al., "Inhibition of Mammary Carcinogenesis by systemic interleukin 12 or P185$^{neu}$ DNA vaccination in HER-2/neu transgenic BALB/c mice", Clinical Cancer Research, Mar. 2001, vol. 7, 830s-837s.

(56) References Cited

OTHER PUBLICATIONS

Disis et al., "Effect of dose on immune response in patients vaccinated with an her-2/neu intracellular domain protein-based vaccine", Journal of Clinical Oncology, vol. 22, No. 10, May 2004, 1916-1925.
Disis et al., "Generation of T-cell Immunity to the HER-2/neu Protein After Active Immunization with HER-2/neu Peptide-Based Vaccines", J. Clin. Oncol. 20:2624-2632, 2002.
Disis et al., "HER-2/neu protein: A target for antigen-specific immunotherapy of Human Cancer", Adv Cancer Res 71:343-371,1997.
Disis et al., "Immunity to the HER-2/neu oncogenic protein", Ciba Found. Symp. 1994 187:198-211.
Disis et al., "Peptide-Based, but not whole protein, vaccines elicit immunity to HER-2/neu, an oncogenic self-protein", The Journal of Immunology, 1996, 156:3151-3158.
Doling et al., "Cytotoxic T-lymphocyte epitopes fused to anthrax toxin induce protective antiviral immunity", Infect. Immun., Jul. 1999, 67(7):3290-6.
Dumitrescu et al., "Understanding breast cancer risk—where do we stand in 2005?", J. Cell. Mol. Med., vol. 9, No. 1, 2005, pp. 208-221.
Dunn et al., "A critical function for type I interferons in cancer immunoediting", vol. 6, No. 7, Jul. 2005, Nature Immunology, 722-729.
Dunn et al., "Cancer immunoediting from immunosurveillance to tumor escape", Nature Immunology, vol. 3, No. 11, Nov. 2002, 991-998.
Dunn et al., "Interferon-γ and cancer Immunoediting", Immunologic Research, 2005, 32/1-3: 231-245.
Dunn, "The Immunobiology of cancer Immunosurveillance and Immunoediting", Immunity, Aug. 2004, vol. 21, 137-148.
Ercolini et al., "Recruitment of latent pools of high-avidity CD8+ T cells to the antitumor immune response", JEM, vol. 201, No. 10, May 2005, 1591-1602.
Esserman et al., "Vaccination with the extracellular domain of P185$^{neu}$ prevents mammary tumor development in neu transgenic mice", Cancer Immunol. Immunother., 1999, 47, 337-342.
Fields, "Preparation of antipeptide antibodies- Introduction to peptide synthesis", Current Protocols in Molecular Biology, 2002, 11.15.1-11.15.9.
Finn et al., "MUC-1 Epithelial Tumor Mucin-Based Immunity and Cancer Vaccines", Immuno. Rev. 1995, 145:61-89.
Foy et al., "Vaccination with HER-2/neu DNA or protein subunits protects against growth of HER-2/neu—expressing murine tumor", Vaccine, 19, 2001, 2598-2606.
Freshney, "Culture of animal cells—a manual of basic technique", Chapter 1, Second Edition, 1983, 1-6.
Gallo et al., "Xenogeneic immunization in mice using HER2 DNA delivered by an adenoviral vector", Int. J. Cancer, 113, 67-77, 2005.
Gansbacher et al., "Interleukin 2 Gene Transfer into Tumor Cells Abrogates Tumorigenicity and Induces Protective Immunity", J. Exp. Med. 1990, 172, 1217-1224.
Garay-Malpartida et al., "Caspredictor: a new computer-based tool for caspase substrate prediction", Bioinformatics, vol. 21, suppl. 1, 2005, p. 169-176.
Garcia-Lora et al., "MHC class I-deficient metastatic tumor variants immunoselected by T lymphocytes originate from the corrdinated downregulation of Apm components", Int. J. Cancer, 106, 521-527, 2003.
Gillespie et al., "The potential of melanoma antigen expression in cancer therapy", Cancer Treat. Rev. 1999, 25(4):219-27.
Glenting et al., "A plasmid selection system in lactococcus lactis and its use for gene expression in L lactis and human kidney fibroblasts", Applied and Environmental Microbiology, Oct. 2002, vol. 68, No. 10, p. 5051-5056.
Golsteyn et al., "Structural and functional similarities between the human cytoskeletal protein zyxin and the ActA protein of *Listeria monocytogenes*", J. Cell Sci. 110:1893-1906, 1997.
Golumbek et al., "Treatment of Established Renal Cancer by Tumor Cells Engineered to Secrete Interleukin-4", Science 1991, 254, 713-716.

Gregory et al., 1997, "Internalin B promotes the replication of *Listeria monocytogenes* in mouse hepatocytes", Infect. Immun. 65(12):5137-41.
Gritzapis et al., "Vaccination with Human HER-2/neu (435-443) CTL peptide induces effective antitumor immunity against HER-2/neu—expressing tumor cells in vivo", Cancer Res., 66, 10, May 2006, 5452-5460.
Gunn, "Recombinant listeria monocytogenes as a tumor therapeutic", *Univ. of Pennsylvania—Electronic Dissertations*. Paper AAI3015316, UMI Microform 3015316, 2001, pp. v-vi, Bell and Howell Information and Learning Company, Ann Arbor, Michigan, abstract.
Guy et al., "Expression of the neu proto oncogene in the mammary epithelium of transgenic mice induces metastatic disease", Proc. Natl. Acad. Sci. USA, Nov. 1992, vol. 89, pp. 10578-10582.
Harris et al., "Molecular Basis for Hetreogeneity of the Human p53 protein", Molecular and Cellular Biology, Dec. 1986, vol. 6, No. 12, p. 4650-4656.
Harty et al., "CD8 T lymphocytes specific for the secreted p60 antigen protect against *Listeria monocytogenes* infection", J. Immunol., May 1, 1995; 154(9):4642-50.
Hess et al., "Live antigen carriers as tools for improved anti-tuberculosis vaccines", FEMS Immunol. Med. Microbiol., Feb. 1999, 23(2), 165-73.
Higgins et al., "Delivery of protein to the cytosol of macrophages using *Escherichia coli* K-12", Mol. Microbiol., Mar. 1999, 31(6):1631-41.
Hiltbold et al., "Mechanisms of processing and presentation of the antigens of *Listeria monocytogenes*", Infect. Agents Dis., Oct. 1993; 2(5):314-23.
Hiltbold et al., "The presentation of class I and class II epitopes of listeriolysin O is regulated by intracellular localization and by intracellular localization and by intercellular spread of *Listeria monocytogenes*", J. Immunol., Aug. 1996; 157(3):1163-75.
Hoogenboom et al., "By passing Immunisation—human antibodies from synthetic repertoires of germline V$_H$ gene segments rearranged in vitro", J. Mol. Biol., 1992, 227, 381-388.
Hueman et al., "Phase I clinical trial of a HER-2/neu peptide (E75) vaccine for the prevention of prostate—specific antigen recurrence in high-risk prostate cancer patients", Clin. Cancer Res., 11(20), Oct. 2005, 7470-7479.
Ikonomidis et al., "Influenza-specific immunity induced by recombinant *Listeria monocytogenes* vaccines", Vaccine, vol. 15, No. 4, pp. 433-440, 1997.
Ikonomidis et al., "Recombinant *Listeria monocytogenes* Cancer Vaccines", Vaccine 95, 1995, 95:317-326.
Ikonomidis et al., ASM Las Vegas, The 94th General Meeting of the American Society for Microbiology, May 23-27, 1994, Las Vegas Convention Center, Las Vages, Nevada, p. 29, 159, 662, 664.
International Search Report of Application No. PCT/US01/09736 dated Jul. 27, 2001.
International Search Report of Application No. PCT/US05/32682 dated Jun. 1, 2006.
International Search Report of Application No. PCT/US07/06292 dated Jun. 17, 2008.
International Search Report of Application No. PCT/US07/10635 dated Sep. 11, 2008.
International Search Report of Application No. PCT/US08/03067 dated Aug. 29, 2008.
International Search Report of Application No. PCT/US08/06048 dated Nov. 20, 2008.
International Search Report of Application No. PCT/US95/14741 dated Feb. 15, 1996.
Jenson et al., "Recombinant *Listeria monocytogenes* as a live vaccine vehicle and a probe for studying cell-mediated Immunity", Immunological Review, vol. 158, 147-157.
Kawashima et al., "The Multi-epitope Approach for Immunotherapy for Cancer: Identification of Several CTL Epitopes from Various Tumor-Associated Antigens Expressed on Solid Epithelial Tumors", Hum. Immunol. 1998 59:1-14.

(56) References Cited

OTHER PUBLICATIONS

Khong et al., "Identification of multiple antigens recognized by tumor-infiltrating lymphocytes from a single patient: Tumor escape by antigen loss and loss of MHC expression", J. Immunother., 2004, 27, 184-190.
King et al., "Amplification of a Novel v-erbB-related gene in a human mammary carcinoma", Science, Sep. 1985, vol. 229, 974-976.
Kohler et al., "Expression of the iap gene coding for protein p60 of *Listeria monocytogenes* is controlled on the posttranscriptional level", Journal of Bacteriology, Aug. 1991, vol. 173, No. 15, p. 4668-4674.
Kruisbeek, "In vivo depletion of CD4- and CD8-specific T cells" Current Protocols in Immunology, John Wiley & Sons, Inc., eds., 1991, V.1, 4.1.1-4.1.2.
Kumar et al., "Amino acid variations at a single residue in an autoimmune peptide profoundly affect its properties: T-cell activation, major histocompatibility complex binding, and ability to block experimental allergic encephalomyelitis", PNAS, 87:1337-1341, 1990.
Kuntson et al., "Neu antigen negative variants can be generated after neu-specific antibody therapy in neu transgenic mice", Cancer Research 64, Feb. 2004, 1146-1151.
Kuntson et al., "Immunization with a HER-2/neu helper peptide vaccine generates HER-2/neu CD8 T-cell immunity in cancer patients", The Journal of Clinical Investigation, 107:477-484,2001.
Kyte et al., "A simple method for displaying the hydropathic character of a protein", J. Mol. Biol., 1982, 157, 105-132.
Lacey et al., "Phase IIa safety and immunogenicity of a therapeutic vaccine, TA-GW, in persons with genital warts", The Journal of Infectious Diseases, 1999, 179:612-8.
Lauer et al., "Systematic mutational analysis of the amino-terminal domain of the *Listeria monocytogenes* ActA protein reveals novel functions in actin-based motility", Molecular Microbiology 42(5):1163-1177, 2001.
Lee et al., "Delivery of macromolecules into cytosol using liposomes containing hemolysin from *Listeria monocytogenes*", J. Biol. Chem., Mar. 29, 1996; 271(13):7249-52.
Lee et al., "The murine MHC class I genes, H-2D and H-2L, and two genes reported to encode tumor-specific antigens", J. Exp. Med., Nov. 1988, vol. 168, 1719-1739.
Leitner et al., "DNA and RNA-based vaccines: prinicples, progress and prospects", Vaccine, Dec. 1999, 18(9-10):765-777.
Lipford et al., "Vaccination with immunodominant peptides encapsulated in Quil A-containing liposomes induces peptide-specific primary CD8+ cytotoxic T cells", Vaccine, Jan. 1994; 12(1):73-80.
Liu, "Vaccine developments", Nature Medicine Vaccine Supplement, May 1998, vol. 4, No. 5, 515-519.
Marks et al., "By-Passing immunization human antibodies from V-gene libraries displayed on phage", J. Mol. Biol. 1991, 222, 581-597.
Mata et al., "Evaluation of a recombinant *Listeria monocytogenes* expressing an HIV protein that protects mice against viral challenge", Vaccine, 19, 2001, 1435-1445.
Mazzaccaro et al., "Major histocompatibility Class I presentation of soluble antigen facilitated by *Mycobacterium tuberculosis* infection", Proc. Natl. Acad. Sci. USA; Oct. 15, 1996; 93(21):11786-91.
McCarty et al., "Targeting p53 for Adoptive T-Cell Immunotherapy", Cancer Research 1998, 15:58 2601-5.
McKaig et al., "Human Papillomavirus and Head and Neck Cancer: Epidemiology and Molecular Biology", Head Neck 1998, 20 (3):250-65.
Mengaud et al., "Expression in *Escherichia coli* and sequence analysis of the Listeriolysin O determinant of *Listeria monocytogenes*", Infect. Immun., vol. 56, No. 4, 766-772, 1988.
Miller et al., "Targeted vectors for gene therapy", The FASEB Journal, Feb. 1995, vol. 9, p. 190-199.
Muller, "Expression of activated oncogenes in the murine mammary gland: transgenic models for human breast cancer", Cancer and Metastasis Reviews, 10:217-227, 1991.

Murali et al., "Structural analysis of P185$^{C-neu}$ and epidermal growth factor receptor tyrosine kinases: oligomerization of kinase domains", Proc. Natl. Acad. Sci. USA, vol. 93, pp. 6252-6257, Jun. 1996, Biochemistry.
Naz et al., "Novel human prostate-specific cDNA: molecular cloning, expression, and immunobiology of the recombinant protein", Biochemical and Biophysical Research Communications 297, 2002, 1075-1084.
Neeson et al., "A DNA prime-oral listeria boost vaccine in rhesus macaques induces a SIV-specific CD8 T cell mucosal response characterized by high levels of α4β7 integrin and an effector memory phenotype", Virology, Oct. 2006, 354(2), 299-315.
Neeson et al., "Listeriolysin O is an improved protein carrier for lymphoma immunoglobulin idiotype and provides systemic protection against 38c/3 lymphoma", Cancer Immunol. Immunother., 2008, pp. 493-505.
Nielsen et al., "Peptide nucleic acids as therapeutic agents", Nucleic acids, p. 353-357, Curr Opinion Struc Biol 9(3): 353-7, Jun. 1997.
Pagano, J.S., "Epstein-Barr Virus: The First Human Tumor Virus and its Role in Cancer", Proc. Assoc. Am. Physicians 1999 111(6):573-80.
Pardoll, "Cancer Vaccines", Nature Medicine Vaccine Supplement, May 1998, vol. 4, No. 5, 525-531.
Paterson et al., "Recombinant *Listeria monocytogenes* cancer vaccines", Curr Opin Immunol. Oct. 1996;8(5) 664-669.
Paterson et al., Proceedings of the American Association for Cancer Research, Mar. 2000, 41:890, abstract # S25.
Paterson, "Rational approaches to immune regulation", Immunogenic Research, 27(2-3):451-462, Jun. 2003.
Piechocki et al., "Complementary Antitumor Immunity Induced by Plasmid DNA Encoding Secreted and Cytoplasmic Human ErbB-2", The Journal of Immunology, 2001, 167:3367-3374.
Pilgrim et al., "Bactofection of mammalian cells by *Listeria monocytogenes*: improvement and mechanism of DNA delivery", Gene Therapy, 2003, 10, 2036-2045.
Pilon et al., "Vaccination with Crytoplasmic ErbB-2 DNA Protects Mice from Mammary Tumor Growth Without Anti-ErbB-2 Antibody", The Journal of Immunology, 2001, 167:3201-3206.
Pricher et al., "Viral escape by selection of cytotoxic T cell-resistant virus variants in vivo", Nature, vol. 346, Aug. 1990, 629-633.
Pucci et al., "*Straphylococcus hameolyticus* contains two D-glutamic acid biosynthetic activities, a glutamate racemase and a D-amino acid transaminase", Journal of Bacteriology, Jan. 1995, vol. 177, No. 2, p. 336-342.
Punwaney et al., "Human Papillomavirus May be Common within Nasopharyngeal Carcinoma of Caucasian Americans: investigation of Epstein-Barr virus and human papillomavirus in Eastern and Western Nasopharyngeal Carcinoma using Ligation-Dependent polymerase chain reaction", Head Neck, 1999, 21(1):21-9.
Raffaghello et al., "Multiple defects of the antigen-processing machinery components in human neuroblastoma: immunotherapeutic implications", Oncogene, 2005, 24, 4634-4644.
Reilly et al., "HER-2/neu is a tumor rejection target in tolerized HER-2/neu transgenic mice", Cancer Research 60, 3569-3576, Jul. 2000.
Restifo et al., "Identification of Human Cancers Deficient in Antigen Processing", J. Exp. Med. 1993, 177, 265-272.
Restifo et al., "The promise of nucleic acid vaccines", Gene Ther., Jan. 2000, 7(2): 89-92.
Rogers et al., "Amino acid sequences common to rapidly degraded proteins: the PEST hypothesis", Science, Reports, Oct. 1986, vol. 234, 364-368.
Romero et al., "Coordinated downregulation of the anti gen presentation machinery and HLA class I/β2- microglobulin complex is responsible for HLA-ABC loss in bladder cancer", Int. J. Cancer, 2005, 113, 605-610.
Rovero et al., "DNA Vacciniation Against Rat Her-2/Neu p185 More Effectively Inhibits Carcinogenesis Than Transplantable Carcinomas in Transgenic BALB/c Mice", The Journal of Immunology, 2000, 165:5133-5142.
Scardino et al., "HER-2/neu and hTERT cryptic epitopes as Novel targets for broad spectrum tumor Immunotherapy", The Journal of Immunology, 2002, 168:5900-5906.

(56) References Cited

OTHER PUBLICATIONS

Schlom et al., "Cancer Vaccines:Moving Beyond Current Paradigms", Clin. Cancer Res. 2007; 13(13), Jul. 1, 2007, pp. 3776-82.
Schmidt et al., "Molecular Analysis of the Plasmid-Encoded Hemolysin of *Escherichia coli* O157:H7 Strain EDL 933", Infection and Immunity, 63(3):1055-1061, 1995.
Schneider et al., "Induction of pulmonary allergen-specific IgA responses or airway hyperresponsiveness in the absence of allergic lung disease following sensitization with limiting doses of ovalbumin-alum", Cellular Immunology, 212, 101-109, 2001.
Schnupf et al., "Phosphorylation, ubiquitination and degradation of listeriolysin O in mammalian cells: role of the PEST-like sequence", Cellular Microbiology 8(2):353-364, 2006.
Schwartz, "T cell anergy", Annu. Rev. Immunol., 2003, 21, 305-34.
Scortti et al., "The PrfA virulence regulon", Microbes Infect. Aug. 2007;9(10):1196-207. Epub May 7, 2007.
Seffernick et al., "Melamine deaminase and atrazine chlorohydrolase: 98 percent identical but functionally different", J. Bacteriol. 183(8):2405-10, Apr. 2001.
Serth et al., "Increased Levels of Human Papillomavirus Type 16 DNA in a Subset of Prostate Cancers", Cancer Res. 1999 15:59(4):823-5.
Sewell et al., "Regression of HPV-positive tumors treated with a new *Listeria monocytogenes* vaccine", Arch Otolaryngol Head Neck Surg, Jan. 2004, vol. 130, 92-97.
Shen et al., "Recombinant *Listeria monocytogenes* as a Live Vaccine Vehicle for the Induction of Protective Anti-Viral Cell-Mediated Immunity", Proc. Natl. Acad. Sci., USA, 92:3987-3991, Apr. 25, 1995.
Shrikant et al., "CTLA-4 blockade reverses CD8+ T cell tolerance to tumor by a CD4+ T cell- and IL-2-dependent mechanism", Immunity, Oct. 1999, vol. 11, 483-493.
Silverman et al., "Expression of c-myc, c-raf-1, and c-Ki-ras in azaserine-induced pancreatic carcinomas and growing pancreas in rats" Mol. Carcinog 3(6):379-86, 1990.
Singh et al., "Structure-Based design of a potent, selective and irreversible inhibitor of the catalytic domain of the erbb receptor subfamily of protein tyrosine kinases", J. Med. Chem., 1997, 40, 1130-1135.
Singh et al., "Vaccination strategy determines the emergence and dominance of CD8+ T-cell epitopes in a FVB/N Rat HER-2/neu mouse model of breast cancer", Cancer Res., 66, 15, Aug. 2006, 7748-7757.
Stover et al., "New Use of BCG for Recombinant Vaccines", Nature 1991, 351, 456-460.
Strych et al., "Mutant analysis shows that alanine racemases from *Pseudomonas aeruginosa* and *Escherichia coli* are dimeric", Journal of Bacteriology, Aug. 2002, p. 4321-4325.
Szalay et al., "Presentation of *Listeria monocytogenes* antigens by major histocompatibility complex class I molecules to CD8 cytotoxic T lymphocytes independent of listeriolysin secretion and virulence", Eur. J. Immunol., Jul. 1994; 24(7):1471-7.
Teitelbaum et al., "Mycobacterial infection of macrophages results in membrane-permeable phagosomes", Proc. Natl. Acad. Sci. USA, Dec. 1999; 96(26):15190-5.
Thompson et al., "Pathogenicity and Immunogenicity of a *Listeria monocytogenes* strain that requires D-alanine for growth", Infection and Immunity, Aug. 1998, vol. 66, No. 8, p. 3552-3561.
Thull et al., "Recognition and management of hereditary breast cancer syndromes", The Oncologist, 2004; 9:13-24.
Townsend et al., "Tumor Rejection after Direct Costimulation of CD8+ T Cells by B7-Transfected Melanoma Cells", Science 1993, 259, 368-370.
Travis, "A Stimulating New Approach to Cancer Treatment", Science 1993, 259, 310-311.
Ulmanen et al., "Transcription and Translation of Foreign genes in *Bacillus subtilis* by the aid of a secretion vector", Journal of Bacteriology, Apr. 1985, vol. 162, No. 1, p. 176-182.

Uyttenhove et al., "Escape of mouse mastocytoma P815 after Nearly complete rejection is due to antigen-loss variants rather than immunosuppression", J. Exp. Med., vol. 157, Mar. 1983, 1040-1052.
Vazquez et al., "Differerential regulation of Ia expression and antigen presentation by listeriolysin-producing versus non-producing strains of *Listeria monocytogenes*", J. Leukoc Biol., May 1996; 59(5):683-90.
Villanueva et al., "Listeriolysin is processed efficiently into an MHC class I-associated epitope in *Listeria monocytogenes*-infected cells", J. Immunol., Dec. 1, 1995; 155(11):5227-33.
Vines et al., "Identification and charcterization of nucleotide sequence difference in there virulence-associate genes of *Listeria monocytogenes* strains representing clinically important serotypes", Current Microbiology, May 1998, vol. 36, No. 5, pp. 309-318.
Vitiello et al., "Development of a Lipopeptide-based Therapeutic Vaccine to treat chronic HBV infection", J. Clin. Invest., vol. 95, Jan. 1995, 341-349.
Watson et al., "Immunosurveillance is active in colorectal cancer as downregulation but not complete loss of MHC class I expression correlates with a poor prognosis", Int. J. Cancer, 2006, 118, 6-10.
Wei et al., "Protection against mammary tumor growth by vaccination with full-length, modified human ErbB-2 DNA", Int. J. Cancer, 81, 748-754, 1999.
Wilson et al., "Transient expression of bacterial gene fragments in eukaryotic cells: implications for CD8(+) T cell epitope analysis", J. Immunol. Methods, Feb. 2000, 234(1-2):137-47.
Wingens et al., "Structural analysis of an epidermal growth factor / transforming growth factor-α chimera with uniqe ErbB binding specificity", The Journal of Biological Chemistry, vol. 278, No. 40, Issue of Oct. 3, pp. 39114-39123, 2003.
Witkowski et al., "Conversion of a beta-ketoacyl synthase to a malonyl decarboxylase by replacement of the active-site cysteine with glutamine", Biochemistry 38(36):11643-50, Sep. 7, 1999.
Wu et al., "Engineering an intracellular pathway for major histocompatibility complex class II presentation of antigens", Proc. Natl. Acad. Sci. USA, 1995, 92:11671-5.
Wunderlich et al., "Assays for T cell function: induction and measurement of cytotoxic T lymphocyte activity", Current Protocols in Immunology, 1997, vol. 3, p. 3.11.1-3.11.20.
Yaghmai et al., "Optimized regulation of gene expression using artificial transcription factors", Molecular Therapy, Jun. 2002, vol. 5, No. 6, 685-694.
Young et al., "Cloning and Expression of Influenza Virus Genes", The Origin of Pandemic Influenza Viruses, W.G. Laver, eds., Elsevier Science Publishing Co., Inc., NY, 1983, p. 129.
Zhang et al., "Selection of Tumor Antigens as Targets for Immune Attack Using Immunohistochemistry: Protein Antigens", Clin. Cancer Res. 1998 4:2669-2676.
Zubair et al., "Live recombinant vaccine vectors for HPV antigens associated with infection and malignancy", In: Vaccines for Human Papillomavirus Infection and Anogential Disease (ed. Robert W. Tindle), 1999, pp. 173-192.
Zwickey et al., "Peptide epitopes from noncytosolic *Listeria monocytogenes* can be presented by major histocompatibiity complex class I molecules", Infect. Immun., May 1996; 64(5):1870-2.
Zwickey et al.,"Antigen secreted from noncytosolic *Listeria monocytogenes* is processed by the classical MHC class I processing pathway", J. Immunol., Jun. 1999, 162(11):6341-50.
Einstein et al. "Heat shock fusion protein-based immunotherapy for treatment of cervical intraepithelial neoplasia III" Gynecologic Oncology 106 (2007) 453-460.
Hausen et al. "Papillomaviruses causing cancer: evasion from host-cell control in early events in carcinogenesis." J Natl Cancer Inst. May 3, 2000;92(9):690-8.
Borysiewicz et al. "A recombinant vaccinia virus encoding Human Papillomavirus Types 16 and 18, E6 and E7 proteins as immunotherapy for Cervical Cancer" Lancet, 0099-5355, Jun. 1, 1996, vol. 347, Issue 9014.
Jager et al. "Identification of NY-ESO-1 epitopes presented by human histocompatibility antigen (HLA)—DRB4*0101-0103 and recognized by CD4(+) T lymphocytes of patients with NY-ESO-1-expressing melanoma" J Exp Med. Feb. 21, 2000;191(4):625-30.

(56) References Cited

OTHER PUBLICATIONS

Mahdavi et al., "Vaccines against Human Papillomavirus and Cervical Cancer: Promises and Challenges" The Oncologist 2005; 10:528-538.
Peng et al. "Adjuvant properties of listeriolysin O protein in a DNA vaccination strategy" Cancer Immunol Immunother. Jun. 2007;56(6):797-806.
Adams et al. (1992) "Cre-lox recombination in *Escherichia coli* cells. Mechanistic differences from the in vitro reaction." J. Mol. Biol. 226:661-673.
Allison et al. (1997) "Cloning and characterization of a *Prevotella melaninogenica* hemolysin." Infect Immun. 65(7):2765-71.
An et al. (1996) "A recombinant minigene vaccine containing a nonameric cytoxic-T-Lymphocyte epitope confers limited protection against *Listeria monocytogenes* infection" Infect. Immun 64,(5):1685-1693.
Anderson (1998) "Human gene therapy." Nature. Apr. 30;392(6679 Suppl):25-30.
Angelakopoulos et al. (2002) "Safety and shedding of an attenuated strain of *Listeria monocytogenes* with a deletion of actA/plcB in adult volunteers: a dose escalation study of oral inoculation." Infect Immun. 70(7):3592-601.
Attwood et al. (2000) "The Babel of Bioinformatics" Science 290(5491):471-473.
Awwad (1989) "Cyclophosphamide-induced immunologically mediated regression of a cyclophosphamide-resistant murine tumor: a consequence of eliminating precursor L3T4+ suppressor T-cells." Cancer Res. 49(7): 1649-1654.
Barry et al. (1992) "Pathogenicity and immunogenicity of *Listeria monocytogenes* small-plaque mutants defective for intracellular growth and cell-to-cell spread." Infection and Immunity 60 (4): 1625-32.
Bast et al. (1975) "Antitumor activity of bacterial infection. II. Effect of *Listeria monocytogenes* on growth of a guinea pig hepatoma. "J Natl. Cancer Inst., 54(3): 757-761.
Bear (1986) "Tumor-specific suppressor T-cells which inhibit the in vitro generation of cytolytic T-cells from immune and early tumor-bearing host spleens." Cancer Res. Apr.; 46(4 Pt 1):1805-12.
Beatly, Dissertation Abstracts International, 2000, 61/10B:5224 Abstract Only.
Bernhard et al. (2002) "Vaccination against the HER-2/neu oncogenic protein." Endocrine-Related Cancer, 9:33-44.
Bielecki et al. (1990) "*Bacillus subtilis* expressing a haemolysin gene from *Listeria monocytogenes* can grow in mammalian cells" Nature 354:175-176.
Billington et al. (1997) "The Arcanobacterium (Actinomyces) pyogenes hemolysin, pyolysin, is a novel member of the thiol-activated cytolysin family." J Bacteriol. Oct.; 179(19):6100-6.
Bodmer et al. (1988) "Enhanced recognition of a modified peptide antigen by cytotoxic T cells specific for influenza nucleoprotein." Cell 52: 253-258.
Boon et al. (2006) "Human T cell responses against melanoma" *Annu Rev Immunol*. 24:175-208.
Bourquin et al. (2000) "Myelin oligodendrocyte glycoprotein-DNA vaccination induces antibody-mediated autoaggression in experimental autoimmune encephalomyelitis" Eur J Immunol 30:3663-3671.
Dietrich et al. (2001) "From evil to good: a cytolysin in vaccine development." Trends Microbiol. Jan.;9(1):23-8.
Dramsi et al. (1995) "Entry of *Listeria monocytogenes* into hepatocytes requires expression of inIB, a surface protein of the internalin multigene family." Mol Microbiol. 16(2):251-61.
Boyer et al. (2005) "DNA prime Listeria boost induces a cellular immune response to SIV antigens in the rhesus macaque model that is capable of limited suppression of SIV239 viral replication." Virology. Mar. 1;333(1):88-101.
Brasseur et al. (1992) "Human gene MAGE-1, which codes for a tumor-rejection antigen, is expressed by some breast tumors. " Int. J Cancer 52(5):839-841.

Brockstedt et al. (2004) "Listeria-based cancer vaccines that segregate immunogenicity from toxicity." Proc Natl Acad Sci USA. 101(38):13832-7.
Bron et al. (2004) "Identification of *Lactobacillus plantarum* genes that are induced in the gastrointestinal tract of mice." J Bacteriol. Sep.;186(17):5721-9.
Brown et al. (1988) "Site-specific integration in *Saccharopolyspora erythraea* and multisite integration in *Streptomyces lividans* of actinomycete plasmid pSE101." J. Bacteriology 170: 2287-2295.
Bruhn et al. (2005) "Characterization of anti-self CD8 T-cell responses stimulated by recombinant *Listeria monocytogenes* expressing the melanoma antigen TRP-2." Vaccine. Jul. 21;23(33):4263-72.
Brundage et al. (1993) "Expression and phosphorylation of the *Listeria monocytogenes* ActA protein in mammalian cells." Proc. Natl. Acad. Sci. USA 90: 11890-11894.
Bubert et al. (1997) "The *Listeria monocytogenes* iap gene as an indicator gene for the study of PrfA-dependent regulation." Mol Gen Genet. Sep.;256(1):54-62.
Burnham (2003) "Bad bugs: good for cancer therapy?" Drug Discovery Today 8(2):54-55.
Calendar et al. Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001&hl=en&ct=clnk&cd=3&gl=us.
Camilli et al. (1993) "Dual roles of plcA in *Listeria monocytogenes* pathogenesis." Mol. Microbiol. 8:143-157.
Carbone (1989) "Induction of ovalbumin-specific cytotoxic T cells by in vivo peptide immunization." J Exp Med 169:603-612.
Carbone (1990) "Class I-restricted processing and presentation of exogenous cell-associated antigen in vivo." J Exp Med 171:377-387.
Chamberlain et al. (2000) "Innovations and strategies for the development of anticancer vaccines." Expert Opinion on Pharmacotherapy 1(4):603-614.
Courvalin et al. (1995) "Gene transfer from bacteria to mammalian cells." C R Acad Sci III. Dec.;318(12):1207-12.
Cunto-Amesty et al. (2003) "Strategies in cancer vaccines development." Int J Parasitol. 33(5-6):597-613.
Dakappagari et al. (2000) "Prevention of mammary tumors with a chimeric HER-2 B-cell epitope peptide vaccine." Cancer Res. Jul. 15;60(14):3782-9.
Darji et al. (2003) "Induction of immune responses by attenuated isogenic mutant strains of *Listeria monocytogenes*." Vaccine 1;21 Suppl 2:S102-9.
Darji et al. (1997) "Oral somatic transgene vaccination using attenuated *S. typhimurium*" Cell 91:765-775.
Darji et al. (1995) "Hyperexpression of listeriolysin in the nonpathogenic species *Listeria innocua* and high yield purification." J Biotechnol. Dec. 15;43(3):205-12.
Darji et al. (1995) "Listeriolysin generates a route for the presentation of exogenous antigens by major histocompatibility complex class I." Eur J Immunol. Oct.;25(10):2967-71.
Darji et al. (1997) "TAP-dependent major histocompatibility complex class I presentation of soluble proteins using listeriolysin." Eur J Immunol. Jun.;27(6):1353-9.
Decatur et al. (2000) "A PEST-like sequence in Listeriolysin O essential for *Listeria monocytogenes* pathogenicity" Science 290(5493):992-995.
Dermime et al. (2004) "Vaccine and antibody-directed T cell tumour immunotherapy." Biochim Biophys Acta. 1704(1):11-35.
Deshpande et al. (1997) "Isolation of a contact-dependent haemolysin from *Mycobacterium tuberculosis*." J Med Microbiol. Mar.;46(3):233-8.
Dietrich et al. (1998) "Delivery of antigen-encoding plasmid DNA into the cytosol of macrophages by attenuated suicide *Listeria monocytogenes*" Nature Biotechnology 15:181-185.
Dunn et al. (1991) "Selective radiation resistance of immunologically induced T cells as the basis for irradiation-induced T-cell-mediated regression of immunogenic tumor." J Leukoc Biol. 49(4): 388-396.
Ebert et al. (1990) "Selective immunosuppressive action of a factor produced by colon cancer cells." Cancer Res. 50(19): 6158-6161.

(56) References Cited

OTHER PUBLICATIONS

Ezzel (1995) "Cancer Vaccines: An Idea Whose Time Has Come?" J. NIH Res., 7:46-49.
Falk et al. (1991) "Identification of naturally processed viral nonapeptides allows their quantification in infected cells and suggests an allele-specific T cell epitope forecast." J Exp Med. 174(2):425-434.
Finn et al. (2003) "Cancer vaccines: between the idea and the reality." Nature Reviews Immunology 3:630-641.
Frankel et al. (1995) "Induction of cell-mediated immune responses to human immunodeficiency virus type 1 Gag protein by using *Listeria monocytogenes* as a live vaccine vector." J. Immunol. 155:4775-4782.
Frey (1993) "Rat adenocarcinoma 13762 expresses tumor rejection antigens but tumor-bearing animals exhibit tumor-specific immunosuppression." Clin Immunol Immunopathol. 69(2):223-233.
Friedman et al. (2000) "Induction of human immunodeficiency virus (HIV)-specific CD8 T-cell responses by *Listeria monocytogenes* and a hyperattenuated *Listeria* strain engineered to express HIV antigens." J. Virology 74 9987-9993.
Fu et al. (1990) "Expansion of immunoregulatory macrophages by granulocyte-macrophage colony-stimulating factor derived from a murine mammary tumor." Cancer Res. 50(2):227-234.
Fujii (1987) "Significance of suppressor macrophages for immunosurveillance of tumor-bearing mice." J Natl Cancer Inst. 78(3):509-517.
Furukawa (1993) "Nude mouse metastatic models of human stomach cancer constructed using orthotopic implantation of histologically intact tissue." Cancer Res. 53(5):1204-1208.
Galen et al. (2001) "Can a 'flawless' live vector vaccine strain be engineered?" Trends Microbiol. 9(8):372-6.
Gentschev et al. (1995) "*Salmonella* strain secreting active Listeriolysin changes its intracellular localization" Infect. Immun. 63:4202-4205.
Gentschev et al. (1996) "Development of antigen-delivery systems, based on the *Escherichia coli* hemolysin secreatiohn pathway." Gene 179:133-140.
Gilmore et al. (1989) "A *Bacillus cereus* cytolytic determinant, cereolysin AB, which comprises the phospholipase C and sphingomyelinase genes: nucleotide sequence and genetic linkage." J Bacteriol. Feb.;171(2):744-53.
Glomski et al. (2002) "The *Listeria monocytogenes* hemolysin has an acidic pH optimum to compartmentalize activity and prevent damage to infected host cells." J Cell Biol. Mar. 18;156(6):1029-38.
Goebel et al. (1993) "*Listeria monocytogenes*—a model system for studying the pathomechanisms of an intracellular microorganism." Zbl. Bakt. 278:334-347.
Goossens et al. (1992) "Induction of protective CD8+ T lymphocytes by an attenuated *Listeria monocytogenes* actA mutant." Int Immunol. Dec.;4(12):1413-8.
Goossens et al. (1995) "Attenuated *Listeria monocytogenes* as a live vector for induction of CD8+ T cells in vivo: a study with the nucleoprotein of the lymphocytic choriomeningitis virus." Int Immunol. May;7(5):797-805.
Gregory et al. (1997) "Internalin B promotes the replication of Listeria monocytogenes in mouse hepatocytes". Infect Immun. 65(12):5137-41.
Gunn (2001) "Two Listeria monocytogenes vaccine vectors that express different molecular forms of human papilloma virus-16 (HPV-16) E7 induce qualitatively different T cell immunity that correlates with their ability to induce regression of established tumors immortalized by HPV-16." J Immunol. 167(11) 6471-6479.
Gunn et al. (2002) "Recombinant Intra-cellular Bacteria as Carriers for Tumor Antigens." In *Vaccine Delivery Strategies*, Chapter 14, Eds. Guido Dietrich and Werner Goebel, Horizon Scientific Press, UK.
Gunn, Dissertation Abstracts International, 2001, 62/5B:2244 Abstract Only.
Gunn et al. (2001) "Listeriolysin—a useful cytolysin." Trends Microbio1.9(4):161-162.

Guzman et al. (1998) "Attenuated *Listeria monocytogenes* carrier strains can deliver an HIV-1 gp120 T helper epitope to MHC class II-restricted human CD4+ T cells" European Journal of Immunology 28:1807-1814.
Harty et al. (1996) "Primary and secondary immune responses to *Listeria monocytogenes*." Curr Opin Immunol. 8:526-530.
Hassan et al. (2004) "Mesothelin: a new target for immunotherapy." Clin Cancer Res. 10(12 Pt 1):3937-42.
Hauf et al. (1997) "*Listeria monocytogenes* infection of P388D1 macrophages results in a biphasic NF-kappaB (RelA/p50) activation induced by lipoteichoic acid and bacterial phospholipases and mediated by IkappaBalpha and IkappaBbeta degradation." Proc Natl Acad Sci U S A. Aug. 19;94(17):9394-9.
Hess et al. (1995) "*Listeria monocytogenes* p60 supports host cell invasion by and in vivo survival of attenuated *Salmonella typhimurium*." Infect Immun. May;63(5):2047-53.
Hess et al. (1996) "*Salmonella typhimurium* aroA- infection in gene-targeted immunodeficient mice: major role of CD4+ TCR-alpha beta cells and IFN-gamma in bacterial clearance independent of intracellular location." J Immunol. May 1;156(9):3321-6.
Hess et al. (1996) "Superior efficacy of secreted over somatic antigen display in recombinant *Salmonella* vaccine induced protection against listeriosis" Proc. Nat. Acad. Sci. 93:1458-1463.
Hess et al. (1997) "Protection against murine listeriosis by an attenuated recombinant *Salmonella typhimurium* vaccine strain that secretes the naturally somatic antigen superoxide dismutase." Infect Immun. Apr.;65(4):1286-92.
Hess et al. (1998) "*Mycobacterium bovis* bacilli Calmette-Guerin strains secreting listeriolysin of *Listeria monocytogenes*" Proc. Natl. Acad. Sci. 95:5299-5304.
Higgins et al. (1998) "Bacterial delivery of DNA evolves." Nat Biotechnol. Feb.;16(2):138-9.
Hodgson (2000) "Generalized transduction of serotype ½and serotype 4b strains of *Listeria monocytogenes*." Mol Microbiol. 35(2):312-23.
Hu et al. (2004) "*Escherichia coli* expressing recombinant antigen and listeriolysin O stimulate class I-restricted CD8+ T cells following uptake by human APC." J. Immunology 172:1595-1601.
Huang et al. (1994) "Role of bone marrow-derived cells in presenting MHC class I-restricted tumor antigens." Science 264961-965.
Hussain et al. (2004) "CD4+CD25+ regulatory T cells that secrete TGFbeta and IL-10 are preferentially induced by a vaccine vector." J Immunother. Sep.-Oct. ;27(5):339-46.
Ikonomidis et al. (1994) Abstract E-90, Abstracts, 94th General Meeting of the American Society for Microbiology, May 23-27.
Ikonomidis et al. (1994) "Delivery of a viral antigen to the class I processing and presentation oathway by *Listeria monocytogenes*" *Journal of Experimental Medicine* 180(6):2209-2218.
Jensen (1997) "Recombinant *Listeria monocytogenes* vaccination eliminates papillomavirus-induced tumors and prevents papilloma formation from viral DNA." *J Virol.* 71(11):8467-8474.
Jensen et al. (1997) "Recombinant *Listeria monocytogenes* as a live vaccine vehicle and a probe for studying cell-mediated immunity" *Immunological Review* 158:147-157.
Jones et al. (1994) "Characterization of *Listeria monocytogenes* pathogenesis in a strain expressing perfringolysin O in place of listeriolysin O." *Infect. Immun.* 62:5608-5613.
Kaufman et al. (1999) "Impact of intracellular location of and antigen display by intracellular bacteria: implications for vaccine development" *J Immunol Lett*, 65(1-2):81-84.
Kerksiek (1999) "T cell responses to bacterial infection" *Curr Opin. Immunol.* 1(4):400-405.
Kocks et al. (1992) "*L. monocytogenes*-induced actin assembly requires the ActA gene product" *Cell* 68(3):521-531.
Kovacsovics-Bankowski et al. (1993) "Efficient major histocompatibility complex class I presentation of exogenous antigen upon phagocytosis by macrophages." *Proc. Natl. Acad. Sci. USA* 90:4942-4946.
Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site." *J. Virology* 75(20):9654-9664.

(56) References Cited

OTHER PUBLICATIONS

Lampson et al. (1993) "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ." *Cancer Research* 53:176-182.
Lara-Tejero et al. (2004) "T cell responses to *Listeria monocytogenes*." *Curr Opin Microbiol.* 7(1):45-50.
Lasa et al. (1997) "Identification of two regions in the N-terminal domain of ActA involved in the actin comet tail formation by *Listeria monocytogenes*" *EMBO* 16(7):1531-40.
Lauer et al. (2002) "Construction, characterization, and use of two *Listeria monocytogenes* site-specific phage integration vectors." *J. Bacteriology* 184: 4177-4186.
Lauer et al. ASM Meeting, Abstract 1999.
Lebrun et al. (1996) "Internalin must be on the bacterial surface to mediate entry of *Listeria monocytogenes* into epithelial cells" *Molecular Microbiology* 21(3):579-592.
Leão et al. (1995) "A species-specific nucleotide sequence of *Mycobacterium tuberculosis* encodes a protein that exhibits hemolytic activity when expressed in *Escherichia coli*." *Infect Immun.* Nov.;63(11):4301-6.
Lee et al. (1991) "Construction of single-copy integration vectors for *Staphylococcus aureus*." *Gene* 103:101-5.
Lehner et al. (1996) "Processing and delivery of peptides presented by MHC class I molecules." *Curr Opin Immunol.* 8(1):59-67.
Lejeune (1994) "Nitric oxide involvement in tumor-induced immunosuppression." *J Immunol.* 152(10):5077-5083.
Liau et al. (2002) "Tumor immunity within the central nervous system stimulated by recombinant *Listeria monocytogenes* vaccination." *Cancer Res.* 62(8):2287-93.
Lin et al. (1996) "Treatment of established tumors with a novel vaccine that enhances Major Histocompatibility Class II presentation of tumor antigen" *Cancer Res.* 56:21-26.
Lin et al. (2002) "Oral vaccination with recombinant *Listeria monocytogenes* expressing human papillomavirus type 16 E7 can cause tumor growth in mice to regress." *Int J Cancer.* Dec. 20;102(6):629-37.
Lingnau et al. (1995) "Expression of the *Listeria monocytogenes* EGD inlA and inlB genes, whose products mediate bacterial entry into tissue culture cell lines, by PrfA-dependent and -independent mechanisms." *Infect Immun.* Oct.;63(10):3896-903.
Loeffler et al. (2006) "Comparison of different live vaccine strategies in vivo for delivery of protein antigen or antigen-encoding DNA and mRNA by virulence-attenuated *Listeria monocytogenes*." *Infect Immun.* Jul.;74(7):3946-57.
Loessner et al. (1995) "Heterogeneous endolysins in *Listeria monocytogenes* bacteriophages: a new class of enzymes and evidence for conserved holin genes within the siphoviral lysis cassettes." *Mol Microbiol.* Jun.;16(6):1231-41.
Makela et al. (1987) Hand Book of Experimental Immunology, vol. 1, chapter 3, pp. 3.1-3.13.
Mandal et al. (2002) "Listeriolysin O-liposome-mediated cytosolic delivery of macromolecule antigen in vivo: enhancement of antigen-specific cytotoxic T lymphocyte frequency, activity, and tumor protection." *BBA* 1563 7-17.
Manjili et al. (2003) "HSP110-HER2/neu chaperone complex vaccine induces protective immunity against spontaneous mammary tumors in HER-2/neu transgenic mice." *J Immunol.* Oct. 15;171(8):4054-61.
Marquis et al. (1997) "Proteolytic pathways of activation and degradation of a bacterial phospholipase C during intracellular infection by *Listeria monocytogenes*." *J. Cell Biol.* 137:1381-1392.
Loessner et al. (2000) "Complete nucleotide sequence, molecular analysis and genome structure of bacteriophage A118 of *Listeria monocytogenes*: implications for phage evolution." *Molecular Microbiology* 35(2):324-40.
Martin et al. (1986) "Nucleotide sequence of the tetM tetracycline resistance determinant of the streptococcal conjugative shuttle transposon Tn1545." *Nucleic Acid Res.* 14:7047-7058.
Marx et al. (2002) "Broad-host-range cre-lox system for antibiotic marker recycling in gram-negative bacteria." *Biotechniques.* Nov.;33(5):1062-7.
McLaughlan et al. (1998) "Molecular characterization of an autolytic amidase of *Listeria monocytogenes* EGD." *Microbiology.* May;144(Pt 5):1359-67.
Mengaud et al. (1988) "Expression in *Escherichia coli* and sequence analysis of the Listeriolysin O determinant of *Listeria monocytogenes*" *Infection and Immunity* 56(4):766-772.
Mikayama et al. (1993) "Molecular cloning and functional expression of a CDNA encoding gycosylation-inhibiting factor" *Proc. Natl. Acad. Sci. USA* 90:10056-10060.
Mlynárová et al. (2002) "The promiscuity of heterospecific lox sites increases dramatically in the presence of palindromic DNA." *Gene.* Aug. 21 ;296(1-2):129-37.
Mollet et al. (1993) "Directed genomic integration, gene replacement, and integrative gene expression in *Streptococcus thermophilus*." *J. Bacteriology* 175:4315-4324.
Moriishi et al. (1998) "Sequence analysis of the actA gene of *Listeria monocytogenes* isolated from human" *Microbiol. Immunol.* 42(2):129-132.
Ngo et al. (1994) The Protein Folding Problem and Tertiary Structure Prediction 492-495.
Ochsenbein et al. (1999) "A comparison of T cell memory against the same antigen induced by virus versus intracellular bacteria." *Proc Natl Acad Sci U S A.* Aug. 3;96(16):9293-8.
Oscarsson et al. (1996) "Induction of haemolytic activity in *Escherichia coli* by the slyA gene product." *Mol Microbiol.* Apr.;20(1):191-9.
Paglia et al. (1997) "The defined attenuated *Listeria monocytogenes* delta mp12 mutant is an effective oral vaccine carrier to trigger a long-lasting immune response against a mouse fibrosarcoma" *Eur J Immunol* 27:1570-1575.
Palmeros et al. (2000) "A family of removable cassettes designed to obtain antibiotic-resistance-free genomic modifications of *Escherichia coli* and other bacteria." *Gene.* Apr. 18;247(1-2):255-64.
Pan (1999) "Regression of established B16F10 melanoma with a recombinant *Listeria monocytogenes* vaccine." *Cancer Res* 59(20):5264-5269.
Pan et al. (1995) "A recombinant *Listeria monocytogenes* vaccine expressing a model tumour antigen protects mice against lethal tumour cell challenge and causes regression of established tumours." *Nature Med.* 1:471-477.
Pan et al. (1995) "Regression of established tumors in mice mediated by the oral administration of a recombinant *Listeria monocytogenes* vaccine" *Cancer Res* 55:4776-4779.
Parida et al. (1998) "Internalin B is essential for adhesion and mediates the invasion of *Listeria monocytogenes* into human endothelial cells." *Mol Microbiol.* Apr.;28(1):81-93.
Paul et al. (1989) "Fundamental Immunology", Second Edition, Raven Press, 987-988.
Peng et al. (2004) "The ability of two Listeria monocytogenes vaccines targeting human papillomavirus-16 E7 to induce an antitumor response correlates with myeloid dendritic cell function." *J. Immunol.* 172:6030-6038.
Penichet et al. (2001) "Antibody-cytokine fusion proteins for the therapy of cancer." *J. Immunological Methods* 248:91-101.
Peters et al. (2003) "Tailoring host immune responses to Listeria by manipulation of virulence genes—the interface between innate and acquired immunity." *FEMS Immunol Med Microbiol.* Apr. 1;35(3):243-53.
Pfeifer et al. (1993) "Phagocytic processing of bacterial antigens for class I MHC presentation to T cells." *Nature.* Jan. 28;361(6410):359-62.
Pupa et al. (2001) "Prevention of spontaneous neu-expressing mammary tumor development in mice transgenic for rat proto-neu by DNA vaccination." *Gene Ther.* Jan.;8(1):75-9.
Quénée et al. (2005) "Combined sacB-based negative selection and cre-lox antibiotic marker recycling for efficient gene deletion in *Pseudomonas aeruginosa*." *Biotechniques.* Jan.;38(1):63-7.
Radford et al. (2002) "A recombinant *E. coli* vaccine to promote MHC class I-dependent antigen presentation: application to cancer immunotherapy." *Gene Therapy* 9:1455-1463.

(56) References Cited

OTHER PUBLICATIONS

Radford et al. (2003) "Recombinant *E. coli* efficiently delivers antigen and maturation signals to human dendritic cells: presentation of MART1 to CD8+ T cells." Int. J. Cancer 105:811-819.
Raveneau et al. (1992) "Reduced virulence of a *Listeria monocytogenes* phospholipase-deficient mutant obtained by transposon insertion into the zinc metalloprotease gene." Infect. Immun. 60: 916-921.
Realini et al. (1994) "KEKE motifs. Proposed roles in protein-protein association and presentation of peptides by MHC class I receptors" FEBS Letters 348:109-113.
Rechsteiner et al. (1996) "PEST sequences and regulation by proteolysis" TIBS 21:267-271.
Reiter et al. (1989) "Transfer RNA genes frequently serve as integration sites for prokaryotic genetic elements." Nucleic Acids Research 17(5)1907-14.
Renard et al. (2003) "HER-2 DNA and protein vaccines containing potent Th cell epitopes induce distinct protective and therapeutic antitumor responses in HER-2 transgenic mice." J Immunol. 171(3):1588-95.
Repique (1992) "Immunosuppression derived from human B-lymphoblastoid and melanoma cell lines." Cancer Invest. 10(3):201-208.
Roden et al. (2004) "Vaccination to prevent and treat cervical cancer." Hum Pathol 35(8):971-82.
Rüssmann et al. (1998) "Delivery of epitopes by the *Salmonella* type III secretion system for vaccine development." Science. Jul. 24;281(5376):565-8.
Safley et al. (1991) "Role of Listeriolysin-o (LLO) in the T Lymphocyte response to infection with *Listeria monocytogenes*" J Immunol. 146(10):3604-3616.
Schafer et al. (1992) "Induction of a cellular immune response to a foreign antigen by a recombinant *Listeria monocytogenes* vaccine." J. Immunol. 149(1):53-59.
Scheirlinck et al. (1989) "Integration and expression of alpha-amylase and endoglucanase genes in the *Lactobacillus plantarum* chromosome." Appl Environ Microbiol 55(9):2130-7.
Schmidt et al. (1995) "Molecular Analysis of the Plasmid-Encoded Hemolysin of *Escherichia coli* O157:H7 Strain EDL 933" Infection and Immunity, 63(3):1055-1061.
Scortti et al. (2007) "The PrfA virulence regulon." Microbes Infect. Aug.;9(10):1196-207.
Sewell et al. (2004) "Regression of HPV-positive tumors treated with a new *Listeria monocytogenes* vaccine." Arch Otolaryngol Head Neck Surg 130:92-97.
Sewell et al. (2004) "Recombinant Listeria vaccines containing PEST sequences are potent immune adjuvants for the tumor-associated antigen human papillomavirus-16 E7." Cancer Res. Dec. 15;64(24):8821-5.
Shen et al. (1995) "Recombinant *Listeria monocytogenes* as a live vaccine vehicle for the induction of protective anti-viral cell-mediated immunity." Proc Nat'l Acad Sci U S A. 92(9):3987-91.
Shen et al. (1998) "*Listeria monocytogenes* as a probe to study cell-mediated immunity" Curr. Opin. Immunol. 10(4):450-458.
Shen et al. (1998) "Compartmentalization of bacterial antigens: differential effects on priming of CD8 T cells and protective immunity." Cell. Feb. 20;92(4):535-45.
Shetron-Rama et al. (2002) "Intracellular induction of *Listeria monocytogenes* actA expression." Infect. Immun. 70:1087-1096.
Shimizu et al. (1994) "Effects of CD4+ and CD8+ T cells in tumor-bearing mice on antibody production." Cancer Immunol Immunother. 38(4):272-276.
Singh et al. (2005) "Fusion to Listeriolysin O and delivery by Listeria monocytogenes enhances the immunogenicity of HER-2/neu and reveals subdominant epitopes in the FVB/N mouse." J Immunol. Sep. 15;175(6):3663-73.
Sirard et al. (1997) "Intracytoplasmic delivery of Listeriolysin O by a vaccinal strain of *Bacillus anthracis* induces CD8-mediated protection against *Listeria monocytogenes*" J Immun. 159:4435-4443.
Skoble, J. et al. (2000). "Three regions within acta promote arp2/3 complex-mediated actin nucleation and *Listeria monocytogenes* motility" The Journal of Cell Biology 150(3):527-537.
Skolnick et al. (2000) "From genes to protein structure and function: novel applications of computational approached in the genomic era" Trends in Biotech. 18(1):34-39.
Slifka et al. (1996) "Antiviral cytotoxic T-cell memory by vaccination with recombinant *Listeria monocytogenes*." J. Virol. 70(5):2902-10.
Smith et al. (1995) "The two distinct phospholipases C of *Listeria monocytogenes* have overlapping roles in escape from a vacuole and cell-to-cell spread." Infect. Immun. 63, 4231-4237.
Smith et al. (1995) "Asymmetric Distribution of the *Listeria monocytogenes* ActA Protein is Required and Sufficient to Direct Actin-Based Motility" Molecular Microbiology 17:945-951.
Souders et al. (2006) "In vivo bactofection: listeria can function as a DNA-cancer vaccine." DNA Cell Biol. Mar.;25(3):142-51.
Stahl et al. (1984) "Replacement of the *Bacillus subtilis* subtilisin structural gene with an in vitro-derived deletion mutation." J. Bacteriol 158:411-418.
Starks et al. (2004) "*Listeria monocytogenes* as a vaccine vector: virulence attenuation or existing antivector immunity does not diminish therapeutic efficacy." J. Immunology 173:420-427.
Stitz et al. (1990) "Characterization and immunological properties of influenza A virus nucleoprotein (NP): cell-associated NP isolated from infected cells or viral NP expressed by vaccinia recombinant virus do not confer protection." J Gen Virol. 71(Pt 5):1169-1179.
Strugnell et al. (1990) "Stable expression of foreign antigens from the chromosome of *Salmonella typhimurium* vaccine strains." Gene 88:57-63.
Stryer et al. (1998) Biochemistry, Third Edition, WH Freeman Company, New York, 31-33.
Sun et al. (1990) "Isolation of *Listeria monocytogenes* small-plaque mutants defective for intracellular growth and cell-to-cell spread." Infect. Immun. 58, 3770-3778.
Tanabe et al. (1999) "Induction of Protective T Cells against *Listeria monocytogenes* in Mice by Immunization with a Listeriolysin O-Negative Avirulent Strain of Bacteria and Liposome-Encapsulated Listeriolysin O" Infect. Immun. 67(2):568-575.
Tilney et al. (1989) "Actin filaments and the growth, movement, and spread of the intracellular bacterial parasite, *Listeria monocytogenes*." J Cell Biol. Oct.;109(4 Pt 1):1597-608.
Vasil et al. (1982) "Cloning of a phosphate-regulated hemolysin gene (phospholipase C) from *Pseudomonas aeruginosa*." J Bacteriol. Oct.;152(1):431-40.
Vazquez-Boland et al. (1992) "Nucleotide sequence of the lecithinase operon of *Listeria monocytogenes* and possible role of lecithinase in cell-to-cell spread." Infect. Immun. 60:219-230.
Verch et al. (2004) "*Listeria monocytogenes*-based antibiotic resistance gene-free antigen delivery system applicable to other bacterial vectors and DNA vaccines." Infect Immun. Nov.;72(11):6418-25.
Verma et al. (1995) "Delivery of class I and class II MHC-restricted T-cell epitopes of listeriolysin of *Listeria monocytogenes* by attenuated *Salmonella*", Vaccine 13(2):142-150.
Zhang et al. (1993) "Functional replacement of the hemolysin A transport signal by a different primary sequence." Proc Natl Acad Sci USA. May 1;90(9):4211-5.
Young et al. (1995) "Holins: form and function in bacteriophage lysis." FEMS Microbiol Rev. Aug.;17(1-2):191-205.
Young et al. (1992) "Tumor-derived cytokines induce bone marrow suppressor cells that mediate immunosuppression through transforming growth factor beta." Cancer Immunol Immunother. 35(1): 14-18.
Wu et al. (1995) "Engineering an intracellular pathway for major histocompatibility complex class II presentation of antigens" Cancer Res. 56:21-26.
Wirth et al. (1986) "Highly efficient protoplast transformation system for *Streptococcus faecalis* and a new *Escherichia coli-S. faecalis* shuttle vector." J Bacteriol. 165(3):831-6.
Welch et al. (1998) "Interaction of Human Arp2/3 Complex and the *Listeria monocytogenes* ActA Protein in Actin Filament Nucleation" Science 281:105-108.

(56) References Cited

OTHER PUBLICATIONS

Weiskirch et al. (1997) "*Listeria monocytogenes*: a potent vaccine vector for neoplastic and infectious disease." Immunological Reviews 158:159-169.

Weidt et al. (1994) "CD8+ T lymphocyte-mediated antiviral immunity in mice as a result of injection of recombinant viral proteins." J Immunol. Sep. 15;153(6):2554-61.

Wei et al. (2005) "*Listeria monocytogenes* phosphatidylinositol-specific phospholipase C has evolved for virulence by greatly reduced activity on GPI anchors." Proc. Natl. Acad. Sci. USA 102: 12927-12931.

Walker et al. (1994) "Tumor growth alters T cell and macrophage production of and responsiveness to granulocyte-macrophage colony-stimulating factor: partial dysregulation through interleukin-10." Cell Immunol. 154(1):342-357.

Watson et al. (1991) "Splenic macrophages from tumor-bearing mice co-expressing MAC-1 and MAC-2 antigens exert immunoregulatory functions via two distinct mechanisms." J Leukoc Biol. 49(2): 126-138.

Sewell et al. "Are Potent Immune Adjuvants for the Tumor-Associated Recombinant Listeria Vaccines Containing PEST Sequences Antigen Human Papillomavirus-16 E7" Cancer Research, 2004, V64, pp. 8821-8825.

Hussain et al. "What is needed for effective antitumor immunotherapy? Lessons learned using *Listeria monocytogenes* as a live vector for HPV-associated tumors" Cancer Immunology Immunotherapy, 2005 V54 N6, pp. 577-586.

Meneguzzi et al., "Immunization against human papillomavirus type 16 tumor cells with recombinant vaccinia viruses expressing E6 and E7", Virology 181(1), 62-69 (1991).

Michel et al., Attenuated mutants of the intracellular bacterium *Listeria monocytogenes* obtained by single amino acid listeriolysin O, Molecular Microbiology (1990), 4(12), pp. 2167-2178.

Unger et al., "Molecular markers for early detection of cervical neoplasia" Disease Markers 20 (2004), pp. 103-116.

Paterson et al., "Listeria-based vaccines for cancer treatment", Curr Opin Mol Ther. Oct. 2005;7(5):454-60.

\* cited by examiner

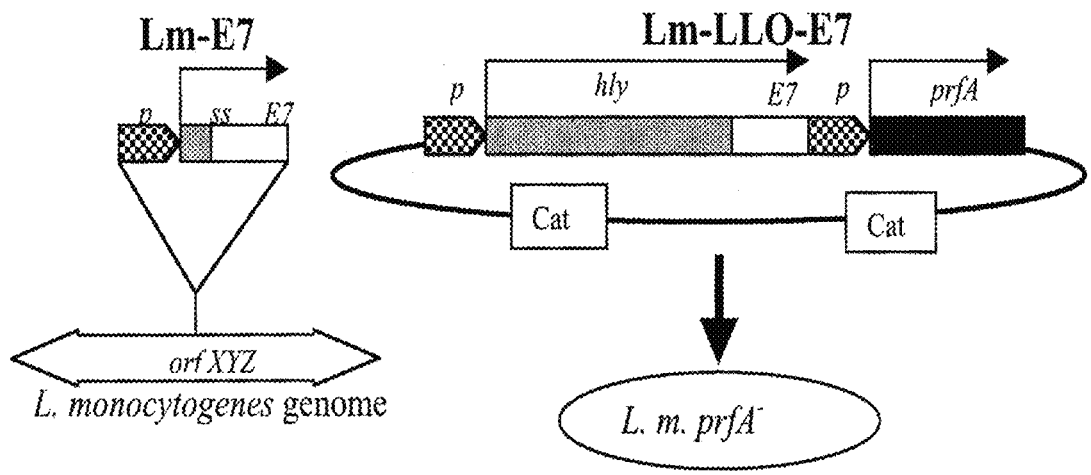
Figure 1A
Figure 1B
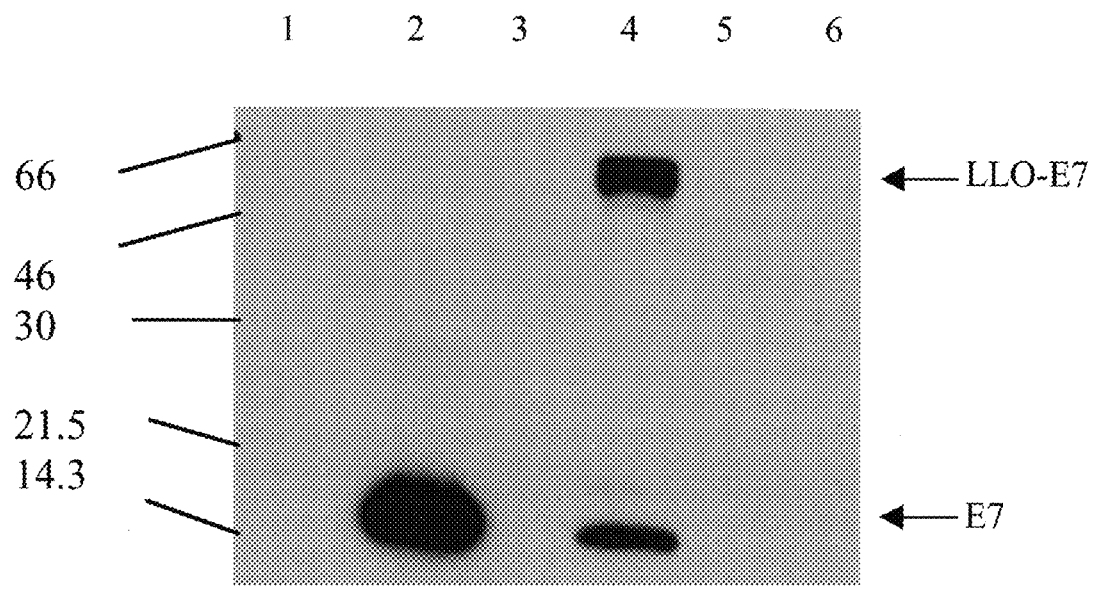
Figure 2

1: Liver
2: Spleen
3: Thyroid
4: Thymus

5. Cathepsin S
6. E7
7. Actin
8. Negative Control

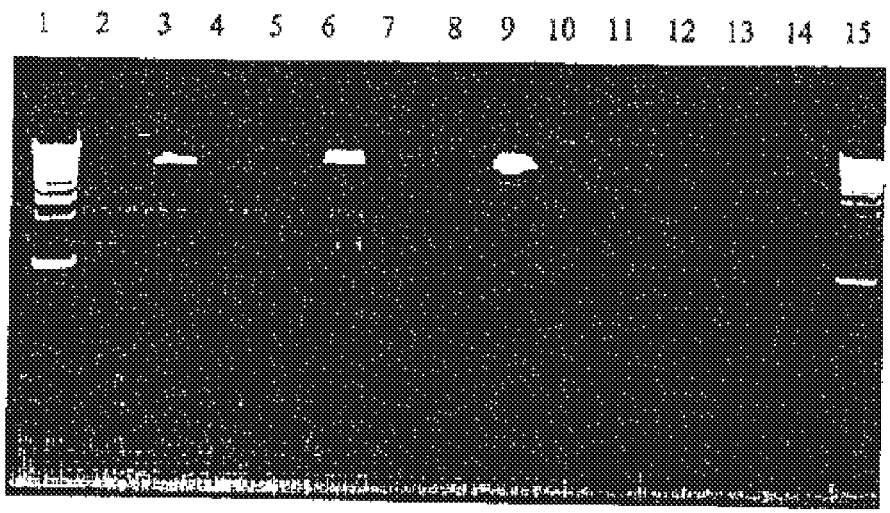

| Lane | Sample | Lane | Sample |
|---|---|---|---|
| 1 | 1Kb ladder | 9 | LB B, generation 5 |
| 2 | 100ng reference pGG55 | 10 | LB A, generation 9 |
| 3 | LB A, generation 5 | 11 | LB B, generation 14 |
| 4 | LB A, generation 9 | 12 | LB B, generation 19* |
| 5 | LB A, generation 14 | 13 | LB B, generation 24* |
| 6 | LB A, generation 19 | 14 | LB B, generation 29* |
| 7 | LB A, generation 24 | 15 | 1Kb ladder |
| 8 | LB A, generation 29 | | |

\* Residual ethanol remaining in sample, therefore the majority of the sample did not load into the well, resulting in a less intense plasmid band

Figure 13A

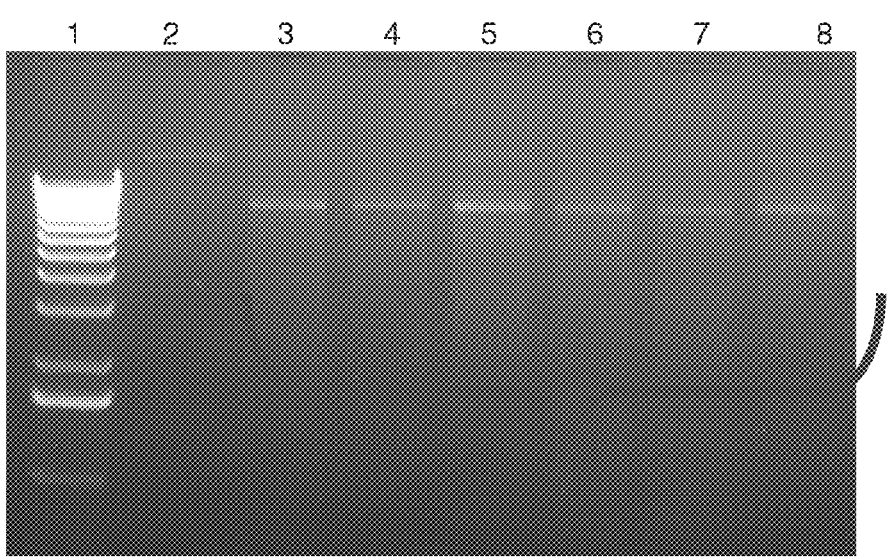

| Lane | Sample | | |
|---|---|---|---|
| 1 | 1Kb ladder | 5 | TB, generation 21 |
| 2 | 100ng reference pGG55 | 6 | TB, generation 28 |
| 3 | TB, generation 7 | 7 | TB, generation 35 |
| 4 | TB, generation 14 | 8 | TB, generation 42 |

Figure 13B

COMPOSITIONS AND METHODS FOR TREATMENT OF CERVICAL DYSPLASIA

CROSS REFERENCE TO RELATED APPLICATIONS

This application is a Continuation-in-Part of U.S. application Ser. No. 11/715,497, filed Mar. 8, 2007, now U.S. Pat. No. 8,114,414, which is a Continuation-in-Part of U.S. application Ser. No. 11/415,271, filed May 2, 2006, now U.S. Pat. No. 8,791,237; and is (1) a Continuation-in-Part of U.S. application Ser. No. 11/373,528, filed Mar. 13, 2006 now U.S. Pat. No. 7,662,396, which is a Continuation-in-Part of U.S. application Ser. No. 10/835,662, filed Apr. 30, 2004 now U.S. Pat. No. 7,588,930, which is a Continuation-in-Part of U.S. application Ser. No. 10/239,703, filed Aug. 7, 2003 now U.S. Pat. No. 7,635,479, which is a National Phase Application of PCT International Application No. PCT/US01/09736, International Filing Date Mar. 26, 2001, now expired; and is (2) a Continuation-in-Part of U.S. application Ser. No. 11/223,945, filed Sep. 13, 2005 now U.S. Pat. No. 7,820,180, which is a Continuation-in-Part of U.S. application Ser. No. 10/949,667, filed Sep. 24, 2004 now U.S. Pat. No. 7,794,729. These applications are hereby incorporated in their entirety by reference herein.

FIELD OF INVENTION

The present invention provides methods of treating, protecting against, and inducing an immune response against cervical pre-cancer or dysplasia, comprising the step of administering to a subject a recombinant *Listeria* strain, comprising a fusion peptide that comprises an LLO fragment and an E7 and/or E6 antigen. The present invention also provides methods for inducing an anti-E7 CTL response in a human subject and treating HPV-mediated diseases, disorders, and symptoms, comprising administration of the recombinant *Listeria* strain.

BACKGROUND OF THE INVENTION

Worldwide, approximately 500,000 cases of cervical cancer are diagnosed each year. Cancer of the cervix (cervical cancer) begins in the lining of the cervix and is the result of infection-induced mutations of cervical cells by the human papilloma virus (HPV). Early manifestations of persistent HPV infection are reflected when normal cervical cells gradually develop pre-cancerous changes that turn into cancer. Several terms are used to describe these pre-cancerous changes, including cervical intraepithelial neoplasia (CIN), squamous intraepithelial lesion (SIL), and neoplasia in situ, dysplasia.

There are 2 major types of cervical cancers: squamous cell carcinoma and adenocarcinoma. Cervical cancers and cervical precancers are classified by microscopic appearance. About 80%-90% of cervical cancers are squamous cell carcinomas, which are composed of cells that resemble the flat, thin cells called squamous cells that cover the surface of the endocervix. Squamous cell carcinomas most often begin where the ectocervix joins the endocervix.

The remaining 10%-20% of cervical cancers are adenocarcinomas. Adenocarcinomas are becoming more common in women born in the last 20 to 30 years. Cervical adenocarcinoma develops from the mucus-producing gland cells of the endocervix. Less commonly, cervical cancers have features of both squamous cell carcinomas and adenocarcinomas. These are called "adenosquamous carcinomas" or "mixed carcinomas."

Improved therapies for cervical pre-cancer or dysplasia are urgently needed in the art.

SUMMARY OF THE INVENTION

The present invention provides methods of treating, protecting against, and inducing an immune response against cervical pre-cancer or dysplasia, comprising the step of administering to a subject a recombinant *Listeria* strain, comprising a fusion peptide that comprises an LLO fragment and an E7 and/or E6 antigen. The present invention also provides methods for inducing an anti-E7 CTL response in a human subject and treating HPV-mediated diseases, disorders, and symptoms, comprising administration of the recombinant *Listeria* strain.

In one embodiment, the present invention provides a method of treating a cervical dysplasia in a human subject, comprising the step of administering to the subject a recombinant *Listeria* strain, the recombinant *Listeria* strain comprising a recombinant polypeptide comprising an N-terminal fragment of an LLO protein fused to an Human Papilloma Virus (HPV) E7 antigen, whereby the recombinant *Listeria* strain induces an immune response against the E7 antigen, thereby treating a cervical pre-cancer or dysplasia in a human subject.

In another embodiment, the present invention provides a method of protecting a human subject against a cervical cancer comprising the step of administering to the subject a recombinant *Listeria* strain, the recombinant *Listeria* strain comprising a recombinant polypeptide comprising an N-terminal fragment of an LLO protein fused to an HPV E7 antigen, whereby the recombinant *Listeria* strain induces an immune response against the E7 antigen, thereby protecting a human subject against a cervical cancer. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

In another embodiment, the present invention provides a method for inducing an immune response against a cervical dysplasia in a human subject, comprising the step of administering to the subject a recombinant *Listeria* strain, the recombinant *Listeria* strain comprising a recombinant polypeptide comprising an N-terminal fragment of an LLO protein fused to an HPV E7 antigen, whereby the recombinant *Listeria* strain induces an immune response against the E7 antigen, thereby inducing an immune response against a cervical pre-cancer or dysplasia in a human subject. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

In another embodiment, the present invention provides a method for inducing an anti-E7 cytotoxic T cell response against a cervical dysplasia in a human subject, comprising the step of administering to the subject a recombinant *Listeria* strain, the recombinant *Listeria* strain comprising a recombinant polypeptide comprising an N-terminal fragment of an LLO protein fused to an HPV E7 antigen, whereby the recombinant *Listeria* strain induces an immune response against the E7 antigen, thereby inducing an anti-E7 cytotoxic T cell response against a cervical dysplasia in a human subject. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

BRIEF DESCRIPTION OF THE DRAWINGS

FIGS. 1A-1B. Lm-E7 and Lm-LLO-E7 use different expression systems to express and secrete E7. Lm-E7 was generated by introducing a gene cassette into the orfZ domain of the *L. monocytogenes* genome (FIG. 1A). The hly promoter drives expression of the hly signal sequence and the first five amino acids (AA) of LLO followed by HPV-16 E7. (FIG. 1B), Lm-LLO-E7 was generated by transforming the prfA-strain XFL-7 with the plasmid pGG-55. pGG-55 has the hly promoter driving expression of a nonhemolytic fusion of LLO-E7. pGG-55 also contains the prfA gene to select for retention of the plasmid by XFL-7 in vivo.

FIG. 2. Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), then developed using ECL detection reagents.

FIG. 5A shows representative data from 1 experiment. FIG. 5B shows average and SE of data from all 3 experiments.

FIG. 7A: Tissue-specific expression of the E7 transgene is detected in the thyroid only but not the liver, spleen, or whole thymus. Lane 1: Liver; Lane 2: Spleen; Lane 3: Thyroid; Lane 4: Whole Thymus. FIG. 7B: Medullary thymic epithelial cells (mTECs) express E7. RT-PCR results are as shown for equivalent amounts of cDNA loaded for 40 cycles. Lane 5: Cathepsin S; Lane 6: E7; Lane 7: Actin; Lane 8: Negative Control.

FIG. 10A. IV immunization of LM-LLO-E7 is effective at inducing the regression of established tumors at doses as low as $1 \times 10^6$ CFU per mouse. FIG. 10B. Tumors loads for the 2 cohorts in the LM-LLO-E7 clinical trial.

FIG. 11A. Effect of passaging on bacterial load (virulence) of recombinant *Listeria* vaccine vectors. Top panel. Lm-Gag. Bottom panel. Lm-LLO-E7. FIG. 11B. Effect of passaging on bacterial load of recombinant Lm-E7 in the spleen. Average CFU of live bacteria per milliliter of spleen homogenate from four mice is depicted.

FIGS. 13A-13B. FIG. 13A. Plasmid isolation throughout LB stability study. FIG. 13B. Plasmid isolation throughout TB stability study. Quantitation of TB stability study.

FIG. 24A. Growth curves of Lm-LLO-E7 in 5 L fermenters in TB and defined media. FIG. 24B. Viability of Lm-LLO-E7 grown in 5 L fermenters in TB to different densities. FIG. 24C. Viability of Lm-LLO-E7 grown in 5 L fermenters in defined media to different densities.

DETAILED DESCRIPTION OF THE INVENTION

Figure 3:
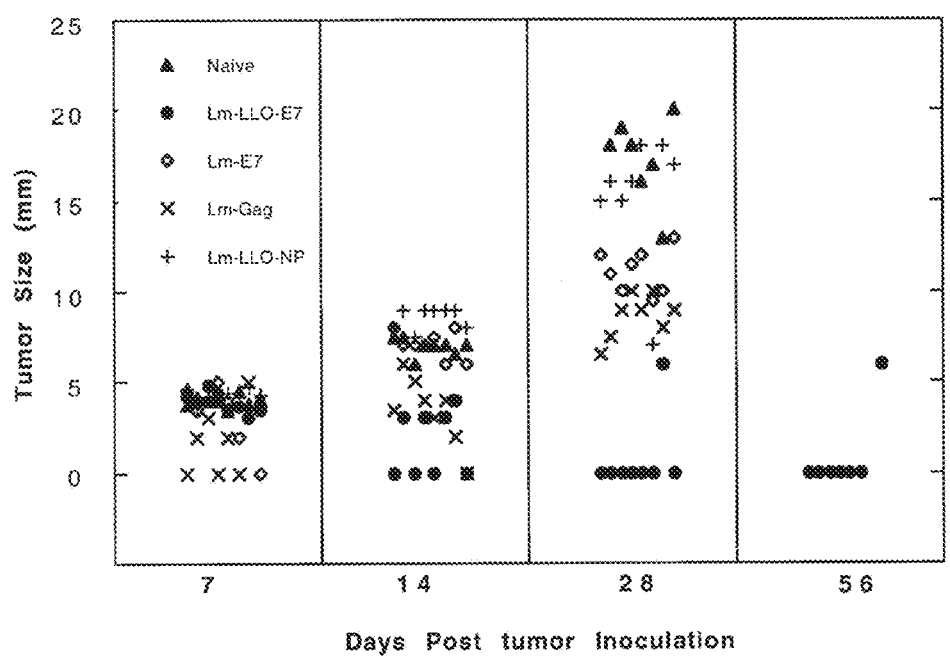
FIG. 3. Tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles.

The present invention provides methods of treating, protecting against, and inducing an immune response against cervical pre-cancer or dysplasia, comprising the step of administering to a subject a recombinant *Listeria* strain, comprising a fusion peptide that comprising a listeriolysin O (LLO) fragment and an E7 antigen. The present invention also provides methods for inducing an anti-E7 CTL response in a human subject and treating HPV-mediated diseases, disorders, and symptoms, comprising administration of the recombinant *Listeria* strain.

In one embodiment, the present invention provides a method of treating a cervical dysplasia in a human subject, comprising the step of administering to the subject a recombinant *Listeria* strain, the recombinant *Listeria* strain comprising a recombinant polypeptide comprising an N-terminal fragment of an LLO protein and an Human Papilloma Virus (HPV) E7 antigen, whereby the recombinant *Listeria* strain induces an immune response against the E7 antigen, thereby treating a cervical pre-cancer or dysplasia in a human subject. In another embodiment, the recombinant *Listeria* strain expresses the recombinant polypeptide. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

The N-terminal LLO protein fragment and HPV E7 antigen are, in another embodiment, fused directly to one another. In another embodiment, the genes encoding the N-terminal LLO protein fragment and HPV E7 antigen are fused directly to one another. In another embodiment, the N-terminal LLO protein fragment and HPV E7 antigen are attached via a linker peptide. In another embodiment, the N-terminal LLO protein fragment and HPV E7 antigen are attached via a heterologous peptide. In another embodiment, the N-terminal LLO protein fragment is N-terminal to the HPV E7 antigen. In another embodiment, the N-terminal LLO protein fragment is the N-terminal-most portion of the fusion protein. Each possibility represents a separate embodiment of the present invention.

In another embodiment, the present invention provides a method of protecting a human subject against a cervical cancer, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby protecting a human subject against a cervical cancer. In another embodiment, the recombinant *Listeria* strain expresses the recombinant polypeptide. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

In another embodiment, the present invention provides a method for inducing an immune response against a cervical dysplasia in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing an immune response against a cervical dysplasia in a human subject. In another embodiment, the recombinant *Listeria* strain expresses the recombinant polypeptide. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising an E7 antigen. In another embodiment, the method further comprises the step of boosting the human subject with an immunogenic composition that directs a cell of the subject to express an E7 antigen. Each possibility represents a separate embodiment of the present invention.

As provided herein, recombinant Listeria strains expressing LLO-antigen fusions induce anti-tumor immunity (Example 1), elicit antigen-specific T cell proliferation (Example 2), generate antigen-specific, tumor-infiltrating T cells (Example 3), and abrogate central and peripheral tolerance to antigens such as E6 and E7 (Examples 4-11). Thus, vaccines of the present invention are efficacious at inducing immune responses against E7 and E6. Further, the recombinant Listeria strains are safe and improve disease indicators in human subjects (Example 9).

In another embodiment, the present invention provides a method of treating a cervical dysplasia in a human subject, comprising the step of administering to the subject a recombinant Listeria strain, the recombinant Listeria strain comprising a recombinant polypeptide comprising an N-terminal fragment of an LLO protein and an HPV E7 antigen, whereby the recombinant Listeria strain induces an immune response against the E7 antigen, thereby treating a cervical pre-cancer or dysplasia in a human subject. In another embodiment, the recombinant Listeria strain expresses the recombinant polypeptide. In another embodiment, the recombinant Listeria strain comprises a plasmid that encodes the recombinant polypeptide. Each possibility represents a separate embodiment of the present invention.

In another embodiment, the present invention provides a method of protecting a human subject against a cervical cancer, comprising the step of administering to the subject a recombinant Listeria strain, the recombinant Listeria strain comprising a recombinant polypeptide comprising an N-terminal fragment of an LLO protein and an HPV E7 antigen, whereby the recombinant Listeria strain induces an immune response against the E7 antigen, thereby protecting a human subject against a cervical pre-cancer or dysplasia. In another embodiment, the recombinant Listeria strain expresses the recombinant polypeptide. In another embodiment, the recombinant Listeria strain comprises a plasmid that encodes the recombinant polypeptide. Each possibility represents a separate embodiment of the present invention.

In another embodiment, the present invention provides a method for inducing an immune response against a cervical dysplasia in a human subject, comprising the step of administering to the subject a recombinant Listeria strain, the recombinant Listeria strain comprising a recombinant polypeptide comprising an N-terminal fragment of an LLO protein and an HPV E7 antigen, thereby inducing an immune response against a cervical dysplasia in a human subject. In another embodiment, the recombinant Listeria strain expresses the recombinant polypeptide. In another embodiment, the recombinant Listeria strain comprises a plasmid that encodes the recombinant polypeptide. Each possibility represents a separate embodiment of the present invention.

As provided herein, recombinant Listeria strains expressing LLO-antigen fusions induce anti-tumor immunity (Example 3), generate antigen-specific, tumor-infiltrating T cells (Example 3), and abrogate central and peripheral tolerance to antigens such as E6 and E7 (Examples 4-11). Further, recombinant Listeria strains of the present invention are safe and improve disease indicators in human subjects (Example 9).

The N-terminal LLO protein fragment and HPV E7 antigen are, in another embodiment, fused directly to one another. In another embodiment, the genes encoding the N-terminal LLO protein fragment and HPV E7 antigen are fused directly to one another. In another embodiment, the N-terminal LLO protein fragment and HPV E7 antigen are attached via a linker peptide. In another embodiment, the N-terminal LLO protein fragment and HPV E7 antigen are attached via a heterologous peptide. In another embodiment, the N-terminal protein fragment is N-terminal to the HPV E7 antigen. In another embodiment, the N-terminal LLO protein fragment is the N-terminal-most portion of the fusion protein. Each possibility represents a separate embodiment of the present invention.

In another embodiment, the present invention provides a method for vaccinating a human subject against an HPV, comprising the step of administering to the subject a recombinant Listeria strain, the recombinant Listeria strain comprising a recombinant polypeptide comprising an N-terminal fragment of an LLO protein and an HPV E7 antigen, thereby vaccinating a human subject against an HPV. In another embodiment, the recombinant Listeria strain expresses the recombinant polypeptide. In another embodiment, the recombinant Listeria strain comprises a plasmid that encodes the recombinant polypeptide. Each possibility represents a separate embodiment of the present invention.

In another embodiment, the present invention provides a method for vaccinating a human subject against an HPV, comprising the step of administering to the subject a recombinant Listeria strain, the recombinant Listeria strain comprising a recombinant polypeptide comprising a PEST-like sequence-containing peptide and an HPV E7 antigen, thereby vaccinating a human subject against an HPV. In another embodiment, the recombinant Listeria strain expresses the recombinant polypeptide. In another embodiment, the recombinant Listeria strain comprises a plasmid that encodes the recombinant polypeptide. Each possibility represents a separate embodiment of the present invention.

In another embodiment, the present invention provides a method for vaccinating a human subject against an HPV, comprising the step of administering to the subject a recombinant Listeria strain, the recombinant Listeria strain comprising a recombinant polypeptide comprising an N-terminal fragment of an LLO protein and an HPV E7 antigen, thereby vaccinating a human subject against an HPV. In another embodiment, the recombinant Listeria strain expresses the recombinant polypeptide. In another embodiment, the recombinant Listeria strain comprises a plasmid that encodes the recombinant polypeptide. Each possibility represents a separate embodiment of the present invention.

As provided herein, recombinant Listeria strains expressing fusions of an antigen to LLO, -induce anti-E6 and E7 immunity (Example 3), and abrogate central and peripheral tolerance to antigens such as E6 and E7 (Examples 4-11). Further, recombinant Listeria strains of the present invention are safe and improve disease indicators in human subjects (Example 9). Thus, Listeria strains of the present invention can be used to vaccinate a subject against an HPV, thereby preventing or inhibiting HPV-mediated carcinogenesis.

In another embodiment, the subject is at risk for developing an HPV-mediated carcinogenesis (e.g. a cervical pre-cancer or dysplasia). In another embodiment, the subject is HPV-positive. In another embodiment, the subject's husband is HPV-positive. In another embodiment, the subject exhibits cervical intraepithelial neoplasia. In another embodiment, the subject exhibits a squamous intraepithelial lesion. In another embodiment, the subject exhibits a dysplasia in the cervix. Each possibility represents a separate embodiment of the present invention.

The HPV that is the target of methods of the present invention is, in another embodiment, an HPV 16. In another embodiment, the HPV is an HPV-18. In another embodiment, the HPV is selected from HPV-16 and HPV-18. In another embodiment, the HPV is an HPV-31. In another embodiment, the HPV is an HPV-35. In another embodiment, the HPV is an HPV-39. In another embodiment, the HPV is an HPV-45. In another embodiment, the HPV is an HPV-51. In another embodiment, the HPV is an HPV-52. In another embodiment, the HPV is an HPV-58. In another embodiment, the HPV is a high-risk HPV type. In another embodiment, the HPV is a mucosal HPV type. Each possibility represents a separate embodiment of the present invention.

In another embodiment, the present invention provides a method for inducing a regression of a cervical dysplasia in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing a regression of a cervical pre-cancer or dysplasia in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for reducing an incidence of relapse of a cervical pre-cancer or dysplasia in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby reducing an incidence of relapse of a cervical pre-cancer or dysplasia in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for suppressing a formation of a cervical dysplasia in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby suppressing a formation of a cervical dysplasia in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for inducing a remission of a cervical pre-cancer or dysplasia in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing a remission of a cervical pre-cancer or dysplasia in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for impeding a growth of a cervical tumor in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby impeding a growth of a cervical tumor in a human subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

The cervical tumor targeted by methods of the present invention is, in another embodiment, a squamous cell carcinoma. In another embodiment, the cervical tumor is an adenocarcinoma. In another embodiment, the cervical tumor is an adenosquamous carcinoma. In another embodiment, the cervical tumor is a small cell carcinoma. In another embodiment, the cervical tumor is any other type of cervical tumor known in the art. Each possibility represents a separate embodiment of the present invention.

In another embodiment, an HPV E6 antigen is utilized instead of or in addition to an E7 antigen in a method of the present invention for treating, protecting against, or inducing an immune response against a cervical pre-cancer or dysplasia.

In another embodiment, the present invention provides a method for inducing an anti-E7 cytotoxic T cell (CTL) response against a cervical dysplasia in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing an anti-E7 CTL response in a human subject. In another embodiment, the recombinant *Listeria* strain comprises a plasmid that encodes the recombinant polypeptide. In another embodiment, the method further comprises the step of boosting the subject with a recombinant *Listeria* strain of the present invention. In another embodiment, the method further comprises the step of boosting the subject with an immunogenic composition comprising an E7 antigen. In another embodiment, the method further comprises the step of boosting the subject with an immunogenic composition that directs a cell of the subject to express an E7 antigen. In another embodiment, the CTL response is capable of therapeutic efficacy against an HPV-mediated disease, disorder, or symptom. In another embodiment, the CTL response is capable of prophylactic efficacy against an HPV-mediated disease, disorder, or symptom. Each possibility represents a separate embodiment of the present invention.

In another embodiment, the present invention provides a method of treating or ameliorating an HPV-mediated disease, disorder, or symptom in a subject, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby treating or ameliorating an HPV-mediated disease, disorder, or symptom in a subject. In another embodiment, the subject is a human subject. In another embodiment, the subject is any other type of subject known in the art. Each possibility represents a separate embodiment of the present invention.

The HPV causing the disease, disorder, or symptom is, in another embodiment, an HPV 16. In another embodiment, the HPV is an HPV-18. In another embodiment, the HPV is an HPV-31. In another embodiment, the HPV is an HPV-35. In another embodiment, the HPV is an HPV-39. In another embodiment, the HPV is an HPV-45. In another embodiment, the HPV is an HPV-51. In another embodiment, the HPV is an HPV-52. In another embodiment, the HPV is an HPV-58. In another embodiment, the HPV is a high-risk HPV type. In another embodiment, the HPV is a mucosal HPV type. Each possibility represents a separate embodiment of the present invention.

In another embodiment, an HPV E6 antigen is utilized instead of or in addition to an E7 antigen in a method of the present invention for treating or ameliorating an HPV-mediated disease, disorder, or symptom.

In another embodiment, an HPV E6 antigen is utilized instead of or in addition to an E7 antigen in a method of the present invention for treating or ameliorating an HPV-mediated disease, disorder, or symptom.

The antigen of methods and compositions of the present invention is, in another embodiment, an HPV E7 protein. In another embodiment, the antigen is an HPV E6 protein. In another embodiment, the antigen is any other HPV protein known in the art. Each possibility represents a separate embodiment of the present invention.

"E7 antigen" refers, in another embodiment, to an E7 protein. In another embodiment, the term refers to an E7 fragment. In another embodiment, the term refers to an E7 peptide. In another embodiment, the term refers to any other type of E7 antigen known in the art. Each possibility represents a separate embodiment of the present invention.

The E7 protein of methods and compositions of the present invention is, in another embodiment, an HPV 16 E7 protein. In another embodiment, the E7 protein is an HPV-18 E7 protein. In another embodiment, the E7 protein is an HPV-31 E7 protein. In another embodiment, the E7 protein is an HPV-35 E7 protein. In another embodiment, the E7 protein is an HPV-39 E7 protein. In another embodiment, the E7 protein is an HPV-45 E7 protein. In another embodiment, the E7 protein is an HPV-51 E7 protein. In another embodiment, the E7 protein is an HPV-52 E7 protein. In another embodiment, the E7 protein is an HPV-58 E7 protein. In another embodiment, the E7 protein is an E7 protein of a high-risk HPV type. In another embodiment, the E7 protein is an E7 protein of a mucosal HPV type. Each possibility represents a separate embodiment of the present invention.

"E6 antigen" refers, in another embodiment, to an E6 protein. In another embodiment, the term refers to an E6 fragment. In another embodiment, the term refers to an E6 peptide. In another embodiment, the term refers to any other type of E6 antigen known in the art. Each possibility represents a separate embodiment of the present invention.

The E6 protein of methods and compositions of the present invention is, in another embodiment, an HPV 16 E6 protein. In another embodiment, the E6 protein is an HPV-18 E6 protein. In another embodiment, the E6 protein is an HPV-31 E6 protein. In another embodiment, the E6 protein is an HPV-35 E6 protein. In another embodiment, the E6 protein is an HPV-39 E6 protein. In another embodiment, the E6 protein is an HPV-45 E6 protein. In another embodiment, the E6 protein is an HPV-51 E6 protein. In another embodiment, the E6 protein is an HPV-52 E6 protein. In another embodiment, the E6 protein is an HPV-58 E6 protein. In another embodiment, the E6 protein is an E6 protein of a high-risk HPV type. In another embodiment, the E6 protein is an E6 protein of a mucosal HPV type. Each possibility represents a separate embodiment of the present invention.

In another embodiment, the present invention provides a method of vaccinating a human subject against an antigen of interest, the method comprising the step of administering intravenously to the human subject a recombinant *Listeria* strain comprising or expressing the antigen of interest, wherein the first peptide is selected from an N-terminal fragment of an LLO protein, thereby vaccinating a human subject against an antigen of interest.

In another embodiment, the present invention provides a method of vaccinating a human subject against an antigen of interest, the method comprising the step of administering intravenously to the human subject an immunogenic composition, comprising a fusion of a first peptide to the antigen of interest, wherein the first peptide is an N-terminal fragment of an LLO protein of interest.

In another embodiment, the present invention provides a method of vaccinating a human subject against an antigen of interest, the method comprising the step of administering intravenously to the human subject a recombinant *Listeria* strain comprising a recombinant polypeptide, the recombinant polypeptide comprising a first peptide fused to the antigen of interest, wherein the first peptide is an N-terminal fragment of an LLO protein.

In another embodiment, the present invention provides a method of inducing a CTL response in a human subject against an antigen of interest, the method comprising the step of administering to the human subject a recombinant *Listeria* strain comprising or expressing the antigen of interest, thereby inducing a CTL response in a human subject against an antigen of interest. In another embodiment, the step of administering is intravenous administration. Each possibility represents a separate embodiment of the present invention.

As provided herein, recombinant *Listeria* strains expressing LLO-antigen fusions induce anti-tumor immunity (Example 1), elicit antigen-specific T cell proliferation (Example 2), generate antigen-specific, tumor-infiltrating T cells (Example 3), and abrogate peripheral tolerance to antigens such as E6 and E7 (Examples 4-11). Thus, vaccines of the present invention are efficacious at inducing immune responses against E7 and E6. Further, the recombinant *Listeria* strains are safe and improve disease indicators in human subjects (Example 9).

In another embodiment, the antigen of interest is HPV-E7. In another embodiment, the antigen is HPV-E6. In another embodiment, the antigen is human papilloma virus antigens E1 and E2 from type HPV-16, -18, -31, -33, -35 or -45 human papilloma viruses Each antigen represents a separate embodiment of the present invention.

The immune response induced by methods and compositions of the present invention is, in another embodiment, a T cell response. In another embodiment, the immune response comprises a T cell response. In another embodiment, the response is a $CD8^+$ T cell response. In another embodiment, the response comprises a $CD8^+$ T cell response. Each possibility represents a separate embodiment of the present invention.

The N-terminal LLO protein fragment of methods and compositions of the present invention comprises, in another embodiment, SEQ ID No: 1. In another embodiment, the fragment comprises an LLO signal peptide. In another embodiment, the fragment comprises SEQ ID No: 15. In another embodiment, the fragment consists approximately of SEQ ID No: 15. In another embodiment, the fragment consists essentially of SEQ ID No: 15. In another embodiment, the fragment corresponds to SEQ ID No: 15. In another embodiment, the fragment is homologous to SEQ ID No: 15. In another embodiment, the fragment is homologous to a fragment of SEQ ID No: 15. The ΔLLO used in some of the Examples was 416 AA long (exclusive of the signal sequence), as 88 residues from the amino terminus which is inclusive of the activation domain containing cysteine 484 were truncated. It will be clear to those skilled in the art that any ΔLLO without the activation domain, and in particular without cysteine 484, are suitable for methods and compositions of the present invention. In another embodiment, fusion of an E7 or E6 antigen to any ΔLLO, including the PEST-like AA sequence, SEQ ID NO: 1, enhances cell mediated and anti-tumor immunity of the antigen. Each possibility represents a separate embodiment of the present invention.

The LLO protein utilized to construct vaccines of the present invention has, in another embodiment, the sequence:

```
MKKIMLVFITLILVSLPIAQQTEAKDASAFNKENSISSMAPPASPP

ASPKTPIEKKHADEIDKYIQGLDYNKNNVLVYHGDAVTNVPPRKGY

KDGNEYIVVEKKKKSINQNNADIQVVNAISSLTYPGALVKANSELV

ENQPDVLPVKRDSLTLSIDLPGMTNQDNKIVVKNATKSNVNNAVNT

LVERWNEKYAQAYPNVSAKIDYDDEMAYSESQLIAKFGTAFKAVNN

SLNVNFGAISEGKMQEEVISFKQIYYNVNVNEPTRPSRFFGKAVTK

EQLQALGVNAENPPAYISSVAYGRQVYLKLSTNSHSTKVKAAFDAA

VSGKSVSGDVELTNIIKNSSFKAVIYGGSAKDEVQIIDGNLGDLRD

ILKKGATFNRETPGVPIAYTTNFLKDNELAVIKNNSEYIETTSKAY

TDGKINIDHSGGYVAQFNISWDEVNYDPEGNEIVQHKNWSENNKSK

LAHFTSSIYLPGNARNINVYAKECTGLAWEWWRTVIDDRNLPLVKN

RNISIWGTTLYPKYSNKVDNPIE
(GenBank Accession No. P13128; SEQ ID NO: 17;
nucleic acid sequence is set forth in GenBank
Accession No. X15127).
```

The first 25 AA of the proprotein corresponding to this sequence are the signal sequence and are cleaved from LLO when it is secreted by the bacterium. Thus, in this embodiment, the full length active LLO protein is 504 residues long. In another embodiment, the above LLO fragment is used as the source of the LLO fragment incorporated in a vaccine of the present invention. Each possibility represents a separate embodiment of the present invention.

In another embodiment, the N-terminal fragment of an LLO protein utilized in compositions and methods of the present invention has the sequence:

```
                                    (SEQ ID NO: 15)
MKKIMLVFITLILVSLPIAQQTEAKDASAFNKENSISSVAPPASPP

ASPKTPIEKKHADEIDKYIQGLDYNKNNVLVYHGDAVTNVPPRKGY

KDGNEYIVVEKKKKSINQNNADIQVVNAISSLTYPGALVKANSELV

ENQPDVLPVKRDSLTLSIDLPGMTNQDNKIVVKNATKSNVNNAVNT

LVERWNEKYAQAYSNVSAKIDYDDEMAYSESQLIAKFGTAFKAVNN

SLNVNFGAISEGKMQEEVISFKQIYYNVNVNEPTRPSRFFGKAVTK

EQLQALGVNAENPPAYISSVAYGRQVYLKLSTNSHSTKVKAAFDAA

VSGKSVSGDVELTNIIKNSSFKAVIYGGSAKDEVQIIDGNLGDLRD

ILKKGATFNRETPGVPIAYTTNFLKDNELAVIKNNSEYIETTSKAY

TDGKINIDHSGGYVAQFNISWDEVNYD.
```

In another embodiment, the LLO fragment corresponds to about AA 20-442 of an LLO protein utilized herein.

In another embodiment, the LLO fragment has the sequence:

```
                                    (SEQ ID NO: 16)
MKKIMLVFITLILVSLPIAQQTEAKDASAFNKENSISSVAPPASPPA

SPKTPIEKKHADEIDKYIQGLDYNKNNVLVYHGDAVTNVPPRKGYKD

GNEYIVVEKKKKSINQNNADIQVVNAISSLTYPGALVKANSELVENQ

PDVLPVKRDSLTLSIDLPGMTNQDNKIVVKNATKSNVNNAVNTLVER

WNEKYAQAYSNVSAKIDYDDEMAYSESQLIAKFGTAFKAVNNSLNVN

FGAISEGKMQEEVISFKQIYYNVNVNEPTRPSRFFGKAVTKEQLQAL

GVNAENPPAYISSVAYGRQVYLKLSTNSHSTKVKAAFDAAVSGKSVS

GDVELTNIIKNSSFKAVIYGGSAKDEVQIIDGNLGDLRDILKKGATF

NRETPGVPIAYTTNFLKDNELAVIKNNSEYIETTSKAYTD.
```

In another embodiment, "truncated LLO" or "ΔLLO" refers to a fragment of LLO that comprises the PEST-like domain. In another embodiment, the terms refer to an LLO fragment that comprises a PEST sequence.

In another embodiment, the terms refer to an LLO fragment that does not contain the activation domain at the amino terminus and does not include cysteine 484. In another embodiment, the terms refer to an LLO fragment that is not hemolytic. In another embodiment, the LLO fragment is rendered non-hemolytic by deletion or mutation of the activation domain. In another embodiment, the LLO fragment is rendered non-hemolytic by deletion or mutation of cysteine 484. In another embodiment, the LLO fragment is rendered non-hemolytic by deletion or mutation at another location. Each possibility represents a separate embodiment of the present invention.

In another embodiment, the LLO fragment consists of about the first 441 AA of the LLO protein. In another embodiment, the LLO fragment consists of about the first 420 AA of LLO. In another embodiment, the LLO fragment is a non-hemolytic form of the LLO protein.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein, then the residue numbers can be adjusted accordingly.

In another embodiment, the LLO fragment is any other LLO fragment known in the art. Each possibility represents a separate embodiment of the present invention.

In another embodiment, the recombinant *Listeria* strain is administered to the human subject at a dose of $1 \times 10^9$-$3.31 \times 10^{10}$ CFU. In another embodiment, the dose is $5\text{-}500 \times 10^8$ CFU. In another embodiment, the dose is $7\text{-}500 \times 10^8$ CFU. In another embodiment, the dose is $10\text{-}500 \times 10^8$ CFU. In another embodiment, the dose is $20\text{-}500 \times 10^8$ CFU. In another embodiment, the dose is $30\text{--}500 \times 10^8$ CFU. In another embodiment, the dose is $50\text{--}500 \times 10^8$ CFU. In another embodiment, the dose is $70\text{--}500 \times 10^8$ CFU. In another embodiment, the dose is $100\text{-}500 \times 10^8$ CFU. In another embodiment, the dose is $150\text{-}500 \times 10^8$ CFU. In another embodiment, the dose is $5\text{-}300 \times 10^8$ CFU. In another embodiment, the dose is $5\text{-}200 \times 10^8$ CFU. In another embodiment, the dose is $5\text{-}150 \times 10^8$ CFU. In another embodiment, the dose is $5\text{-}100 \times 10^8$ CFU. In another embodiment, the dose is $5\text{-}70 \times 10^8$ CFU. In another embodiment, the dose is $5\text{-}50 \times 10^8$ CFU.

In another embodiment, the dose is $5\text{-}30\times10^8$ CFU. In another embodiment, the dose is $5\text{-}20\times10^8$ CFU. In another embodiment, the dose is $1\text{-}30\times10^9$ CFU. In another embodiment, the dose is $1\text{-}20\times10^9$ CFU. In another embodiment, the dose is $2\text{-}30\times10^9$ CFU. In another embodiment, the dose is $1\text{-}10\times10^9$ CFU. In another embodiment, the dose is $2\text{-}10\times10^9$ CFU. In another embodiment, the dose is $3\text{-}10\times10^9$ CFU. In another embodiment, the dose is $2\text{-}7\times10^9$ CFU. In another embodiment, the dose is $2\text{-}5\times10^9$ CFU. In another embodiment, the dose is $3\text{-}5\times10^9$ CFU.

In another embodiment, the dose is $1\times10^9$ organisms. In another embodiment, the dose is $1.5\times10^9$ organisms. In another embodiment, the dose is $2\times10^9$ organisms. In another embodiment, the dose is $3\times10^9$ organisms. In another embodiment, the dose is $4\times10^9$ organisms. In another embodiment, the dose is $5\times10^9$ organisms. In another embodiment, the dose is $6\times10^9$ organisms. In another embodiment, the dose is $7\times10^9$ organisms. In another embodiment, the dose is $8\times10^9$ organisms. In another embodiment, the dose is $10\times10^9$ organisms. In another embodiment, the dose is $1.5\times10^{10}$ organisms. In another embodiment, the dose is $2\times10^{10}$ organisms. In another embodiment, the dose is $2.5\times10^{10}$ organisms. In another embodiment, the dose is $3\times10^{10}$ organisms. In another embodiment, the dose is $3.3\times10^{10}$ organisms. In another embodiment, the dose is $4\times10^{10}$ organisms. In another embodiment, the dose is $5\times10^{10}$ organisms.

Each dose and range of doses represents a separate embodiment of the present invention.

In another embodiment, the recombinant polypeptide of methods of the present invention is expressed by the recombinant *Listeria* strain. In another embodiment, the expression is mediated by a nucleotide molecule carried by the recombinant *Listeria* strain. Each possibility represents a separate embodiment of the present invention.

In another embodiment, the recombinant *Listeria* strain expresses the recombinant polypeptide by means of a plasmid that encodes the recombinant polypeptide. In another embodiment, the plasmid comprises a gene encoding a bacterial transcription factor. In another embodiment, the plasmid encodes a *Listeria* transcription factor. In another embodiment, the transcription factor is prfA. In another embodiment, the transcription factor is any other transcription factor known in the art. Each possibility represents a separate embodiment of the present invention.

In another embodiment, the plasmid comprises a gene encoding a metabolic enzyme. In another embodiment, the metabolic enzyme is a bacterial metabolic enzyme. In another embodiment, the metabolic enzyme is a Listerial metabolic enzyme. In another embodiment, the metabolic enzyme is an amino acid metabolism enzyme. In another embodiment, the amino acid metabolism gene is involved in a cell wall synthesis pathway. In another embodiment, the metabolic enzyme is the product of a D-amino acid aminotransferase gene (dat). In another embodiment, the metabolic enzyme is the product of an alanine racemase gene (dal). In another embodiment, the metabolic enzyme is any other metabolic enzyme known in the art. Each possibility represents a separate embodiment of the present invention.

In another embodiment, a method of present invention further comprises the step of boosting the human subject with a recombinant *Listeria* strain of the present invention. In another embodiment, the recombinant *Listeria* strain used in the booster inoculation is the same as the strain used in the initial "priming" inoculation. In another embodiment, the booster strain is different from the priming strain. In another embodiment, the same doses are used in the priming and boosting inoculations. In another embodiment, a larger dose is used in the booster. In another embodiment, a smaller dose is used in the booster. Each possibility represents a separate embodiment of the present invention.

In another embodiment, a method of present invention further comprises the step of inoculating the human subject with an immunogenic composition comprising the E7 antigen. In another embodiment, the immunogenic composition comprises a recombinant E7 protein or fragment thereof. In another embodiment, the immunogenic composition comprises a nucleotide molecule expressing a recombinant E7 protein or fragment thereof. In another embodiment, the non-Listerial inoculation is administered after the Listerial inoculation. In another embodiment, the non-Listerial inoculation is administered before the Listerial inoculation. Each possibility represents a separate embodiment of the present invention.

"Boosting" refers, in another embodiment, to administration of an additional vaccine dose to a subject. In another embodiment of methods of the present invention, 2 boosts (or a total of 3 inoculations) are administered. In another embodiment, 3 boosts are administered. In another embodiment, 4 boosts are administered. In another embodiment, 5 boosts are administered. In another embodiment, 6 boosts are administered. In another embodiment, more than 6 boosts are administered. Each possibility represents a separate embodiment of the present invention.

The recombinant *Listeria* strain of methods and compositions of the present invention is, in another embodiment, a recombinant *Listeria monocytogenes* strain. In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art. Each possibility represents a separate embodiment of the present invention.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the antigen-containing recombinant peptide. In another embodiment, the *Listeria* strain carries a plasmid comprising the gene encoding the antigen-containing recombinant peptide. In another embodiment, the passaging is performed as described herein (e.g. in Example 12). In another embodiment, the passaging is performed by any other method known in the art. Each possibility represents a separate embodiment of the present invention.

In another embodiment, the recombinant *Listeria* strain utilized in methods of the present invention has been stored in a frozen cell bank. In another embodiment, the recombinant

*Listeria* strain has been stored in a lyophilized cell bank. Each possibility represents a separate embodiment of the present invention.

In another embodiment, the cell bank of methods and compositions of the present invention is a master cell bank. In another embodiment, the cell bank is a working cell bank. In another embodiment, the cell bank is Good Manufacturing Practice (GMP) cell bank. In another embodiment, the cell bank is intended for production of clinical-grade material. In another embodiment, the cell bank conforms to regulatory practices for human use. In another embodiment, the cell bank is any other type of cell bank known in the art. Each possibility represents a separate embodiment of the present invention.

"Good Manufacturing Practices" are defined, in another embodiment, by (21 CFR 210-211) of the United States Code of Federal Regulations. In another embodiment, "Good Manufacturing Practices" are defined by other standards for production of clinical-grade material or for human consumption; e.g. standards of a country other than the United States. Each possibility represents a separate embodiment of the present invention.

In another embodiment, a recombinant *Listeria* strain utilized in methods of the present invention is from a batch of vaccine doses.

In another embodiment, a recombinant *Listeria* strain utilized in methods of the present invention is from a frozen stock produced by a method disclosed herein.

In another embodiment, a recombinant *Listeria* strain utilized in methods of the present invention is from a lyophilized stock produced by a method disclosed herein.

In another embodiment, a cell bank, frozen stock, or batch of vaccine doses of the present invention exhibits viability upon thawing of greater than 90%. In another embodiment, the thawing follows storage for cryopreservation or frozen storage for 24 hours. In another embodiment, the storage is for 2 days. In another embodiment, the storage is for 3 days. In another embodiment, the storage is for 4 days. In another embodiment, the storage is for 1 week. In another embodiment, the storage is for 2 weeks. In another embodiment, the storage is for 3 weeks. In another embodiment, the storage is for 1 month. In another embodiment, the storage is for 2 months. In another embodiment, the storage is for 3 months. In another embodiment, the storage is for 5 months. In another embodiment, the storage is for 6 months. In another embodiment, the storage is for 9 months. In another embodiment, the storage is for 1 year. Each possibility represents a separate embodiment of the present invention.

In another embodiment, a cell bank, frozen stock, or batch of vaccine doses of the present invention is cryopreserved by a method that comprises growing a culture of the *Listeria* strain in a nutrient media, freezing the culture in a solution comprising glycerol, and storing the *Listeria* strain at below −20 degrees Celsius. In another embodiment, the temperature is about −70 degrees Celsius. In another embodiment, the temperature is about ⁻70-⁻80 degrees Celsius.

In another embodiment, a cell bank, frozen stock, or batch of vaccine doses of the present invention is cryopreserved by a method that comprises growing a culture of the *Listeria* strain in a defined media of the present invention (as described below), freezing the culture in a solution comprising glycerol, and storing the *Listeria* strain at below −20 degrees Celsius. In another embodiment, the temperature is about −70 degrees Celsius. In another embodiment, the temperature is about ⁻70-⁻80 degrees Celsius. In another embodiment, any defined microbiological media of the present invention may be used in this method. Each defined microbiological media represents a separate embodiment of the present invention.

In another embodiment of methods and compositions of the present invention, the culture (e.g. the culture of a *Listeria* vaccine strain that is used to produce a batch of *Listeria* vaccine doses) is inoculated from a cell bank. In another embodiment, the culture is inoculated from a frozen stock. In another embodiment, the culture is inoculated from a starter culture. In another embodiment, the culture is inoculated from a colony. In another embodiment, the culture is inoculated at mid-log growth phase. In another embodiment, the culture is inoculated at approximately mid-log growth phase. In another embodiment, the culture is inoculated at another growth phase. Each possibility represents a separate embodiment of the present invention.

In another embodiment of methods and compositions of the present invention, the solution used for freezing contains glycerol in an amount of 2-20%. In another embodiment, the amount is 2%. In another embodiment, the amount is 20%. In another embodiment, the amount is 1%. In another embodiment, the amount is 1.5%. In another embodiment, the amount is 3%. In another embodiment, the amount is 4%. In another embodiment, the amount is 5%. In another embodiment, the amount is 2%. In another embodiment, the amount is 2%. In another embodiment, the amount is 7%. In another embodiment, the amount is 9%. In another embodiment, the amount is 10%. In another embodiment, the amount is 12%. In another embodiment, the amount is 14%. In another embodiment, the amount is 16%. In another embodiment, the amount is 18%. In another embodiment, the amount is 222%. In another embodiment, the amount is 25%. In another embodiment, the amount is 30%. In another embodiment, the amount is 35%. In another embodiment, the amount is 40%. Each possibility represents a separate embodiment of the present invention.

In another embodiment, the solution used for freezing contains another colligative additive or additive with anti-freeze properties, in place of glycerol. In another embodiment, the solution used for freezing contains another colligative additive or additive with anti-freeze properties, in addition to glycerol. In another embodiment, the additive is mannitol. In another embodiment, the additive is DMSO. In another embodiment, the additive is sucrose. In another embodiment, the additive is any other colligative additive or additive with anti-freeze properties that is known in the art. Each possibility represents a separate embodiment of the present invention.

In another embodiment, the nutrient media utilized for growing a culture of a *Listeria* strain is LB. In another embodiment, the nutrient media is TB. In another embodiment, the nutrient media is a defined media. In another embodiment, the nutrient media is a defined media of the present invention. In another embodiment, the nutrient media is any other type of nutrient media known in the art. Each possibility represents a separate embodiment of the present invention.

In another embodiment of methods and compositions of the present invention, the step of growing is performed with a shake flask. In another embodiment, the flask is a baffled shake flask. In another embodiment, the growing is performed with a batch fermenter. In another embodiment, the growing is performed with a stirred tank or flask. In another embodiment, the growing is performed with an airflit fermenter. In another embodiment, the growing is performed with a fed batch. In another embodiment, the growing is performed with a continuous cell reactor. In another embodiment, the growing is performed with an immobilized cell reactor. In another embodiment, the growing is performed with any other means of growing bacteria that is known in the art. Each possibility represents a separate embodiment of the present invention.

In another embodiment, a constant pH is maintained during growth of the culture (e.g. in a batch fermenter). In another embodiment, the pH is maintained at about 7.0. In another embodiment, the pH is about 6. In another embodiment, the pH is about 6.5. In another embodiment, the pH is about 7.5. In another embodiment, the pH is about 8. In another embodiment, the pH is 6.5-7.5. In another embodiment, the pH is 6-8. In another embodiment, the pH is 6-7. In another embodiment, the pH is 7-8. Each possibility represents a separate embodiment of the present invention.

In another embodiment, a constant temperature is maintained during growth of the culture. In another embodiment, the temperature is maintained at about 37° C. In another embodiment, the temperature is 37° C. In another embodiment, the temperature is 25° C. In another embodiment, the temperature is 27° C. In another embodiment, the temperature is 28° C. In another embodiment, the temperature is 30° C. In another embodiment, the temperature is 32° C. In another embodiment, the temperature is 34° C. In another embodiment, the temperature is 35° C. In another embodiment, the temperature is 36° C. In another embodiment, the temperature is 38° C. In another embodiment, the temperature is 39° C. Each possibility represents a separate embodiment of the present invention.

In another embodiment, a constant dissolved oxygen concentration is maintained during growth of the culture. In another embodiment, the dissolved oxygen concentration is maintained at 20% of saturation. In another embodiment, the concentration is 15% of saturation. In another embodiment, the concentration is 16% of saturation. In another embodiment, the concentration is 18% of saturation. In another embodiment, the concentration is 22% of saturation. In another embodiment, the concentration is 25% of saturation. In another embodiment, the concentration is 30% of saturation. In another embodiment, the concentration is 35% of saturation. In another embodiment, the concentration is 40% of saturation. In another embodiment, the concentration is 45% of saturation. In another embodiment, the concentration is 50% of saturation. In another embodiment, the concentration is 55% of saturation. In another embodiment, the concentration is 60% of saturation. In another embodiment, the concentration is 65% of saturation. In another embodiment, the concentration is 70% of saturation. In another embodiment, the concentration is 75% of saturation. In another embodiment, the concentration is 80% of saturation. In another embodiment, the concentration is 85% of saturation. In another embodiment, the concentration is 90% of saturation. In another embodiment, the concentration is 95% of saturation. In another embodiment, the concentration is 100% of saturation. In another embodiment, the concentration is near 100% of saturation. Each possibility represents a separate embodiment of the present invention.

In another embodiment of methods and compositions of the present invention, the culture is grown in media having a maximum volume of 2 liters (L) per vessel. In another embodiment, the media has a maximum volume of 200 ml per vessel. In another embodiment, the media has a maximum volume of 300 ml per vessel. In another embodiment, the media has a maximum volume of 500 ml per vessel. In another embodiment, the media has a maximum volume of 750 ml per vessel. In another embodiment, the media has a maximum volume of 1 L per vessel. In another embodiment, the media has a maximum volume of 1.5 L per vessel. In another embodiment, the media has a maximum volume of 2.5 L per vessel. In another embodiment, the media has a maximum volume of 3 L per vessel.

In another embodiment, the media has a minimum volume of 2 L per vessel. In another embodiment, the media has a minimum volume of 500 ml per vessel. In another embodiment, the media has a minimum volume of 750 ml per vessel. In another embodiment, the media has a minimum volume of 1 L per vessel. In another embodiment, the media has a minimum volume of 1.5 L per vessel. In another embodiment, the media has a minimum volume of 2.5 L per vessel. In another embodiment, the media has a minimum volume of 3 L per vessel. In another embodiment, the media has a minimum volume of 4 L per vessel. In another embodiment, the media has a minimum volume of 5 L per vessel. In another embodiment, the media has a minimum volume of 6 L per vessel. In another embodiment, the media has a minimum volume of 8 L per vessel. In another embodiment, the media has a minimum volume of 10 L per vessel.

Each volume represents a separate embodiment of the present invention.

In another embodiment of methods and compositions of the present invention, the step of freezing or lyophilization is performed when the culture has an $OD_{600}$ of 0.7 units. In another embodiment, the culture has an $OD_{600}$ of 0.8 units. In another embodiment, the $OD_{600}$ is about 0.7 units. In another embodiment, the $OD_{600}$ is about 0.8 units. In another embodiment, the $OD_{600}$ is 0.6 units. In another embodiment, the $OD_{600}$ is 0.65 units. In another embodiment, the $OD_{600}$ is 0.75 units. In another embodiment, the $OD_{600}$ is 0.85 units. In another embodiment, the $OD_{600}$ is 0.9 units. In another embodiment, the $OD_{600}$ is 1 unit. In another embodiment, the $OD_{600}$ is 0.6-0.9 units. In another embodiment, the $OD_{600}$ is 0.65-0.9 units. In another embodiment, the $OD_{600}$ is 0.7-0.9 units. In another embodiment, the $OD_{600}$ is 0.75-0.9 units. In another embodiment, the $OD_{600}$ is 0.8-0.9 units. In another embodiment, the $OD_{600}$ is 0.75-1 units. In another embodiment, the $OD_{600}$ is 0.9-1 units. In another embodiment, the $OD_{600}$ is greater than 1 unit.

In another embodiment, the $OD_{600}$ is significantly greater than 1 unit (e.g. when the culture is produced in a batch fermenter). In another embodiment, the $OD_{600}$ is 7.5-8.5 units. In another embodiment, the $OD_{600}$ is 1.2 units. In another embodiment, the $OD_{600}$ is 1.5 units. In another embodiment, the $OD_{600}$ is 2 units. In another embodiment, the $OD_{600}$ is 2.5 units. In another embodiment, the $OD_{600}$ is 3 units. In another embodiment, the $OD_{600}$ is 3.5 units. In another embodiment, the $OD_{600}$ is 4 units. In another embodiment, the $OD_{600}$ is 4.5 units. In another embodiment, the $OD_{600}$ is 5 units. In another embodiment, the $OD_{600}$ is 5.5 units. In another embodiment, the $OD_{600}$ is 6 units. In another embodiment, the $OD_{600}$ is 6.5 units. In another embodiment, the $OD_{600}$ is 7 units. In another embodiment, the $OD_{600}$ is 7.5 units. In another embodiment, the $OD_{600}$ is 8 units. In another embodiment, the $OD_{600}$ is 8.5 units. In another embodiment, the $OD_{600}$ is 9 units. In another embodiment, the $OD_{600}$ is 9.5 units. In another embodiment, the $OD_{600}$ is 10 units. In another embodiment, the $OD_{600}$ is more than 10 units.

In another embodiment, the $OD_{600}$ is 1-2 units. In another embodiment, the $OD_{600}$ is 1.5-2.5 units. In another embodiment, the $OD_{600}$ is 2-3 units. In another embodiment, the $OD_{600}$ is 2.5-3.5 units. In another embodiment, the $OD_{600}$ is 3-4 units. In another embodiment, the $OD_{600}$ is 3.5-4.5 units. In another embodiment, the $OD_{600}$ is 4-5 units. In another embodiment, the $OD_{600}$ is 4.5-5.5 units. In another embodiment, the $OD_{600}$ is 5-6 units. In another embodiment, the $OD_{600}$ is 5.5-6.5 units. In another embodiment, the $OD_{600}$ is 1-3 units. In another embodiment, the $OD_{600}$ is 1.5-3.5 units.

In another embodiment, the $OD_{600}$ is 2-4 units. In another embodiment, the $OD_{600}$ is 2.5-4.5 units. In another embodiment, the $OD_{600}$ is 3-5 units. In another embodiment, the $OD_{600}$ is 4-6 units. In another embodiment, the $OD_{600}$ is 5-7 units. In another embodiment, the $OD_{600}$ is 2-5 units. In another embodiment, the $OD_{600}$ is 3-6 units. In another embodiment, the $OD_{600}$ is 4-7 units. In another embodiment, the $OD_{600}$ is 5-8 units. In another embodiment, the $OD_{600}$ is 1.2-7.5 units. In another embodiment, the $OD_{600}$ is 1.5-7.5 units. In another embodiment, the $OD_{600}$ is 2-7.5 units. In another embodiment, the $OD_{600}$ is 2.5-7.5 units. In another embodiment, the $OD_{600}$ is 3-7.5 units. In another embodiment, the $OD_{600}$ is 3.5-7.5 units. In another embodiment, the $OD_{600}$ is 4-7.5 units. In another embodiment, the $OD_{600}$ is 4.5-7.5 units. In another embodiment, the $OD_{600}$ is 5-7.5 units. In another embodiment, the $OD_{600}$ is 5.5-7.5 units. In another embodiment, the $OD_{600}$ is 6-7.5 units. In another embodiment, the $OD_{600}$ is 6.5-7.5 units. In another embodiment, the $OD_{600}$ is 7-7.5 units. In another embodiment, the $OD_{600}$ is more than 10 units. In another embodiment, the $OD_{600}$ is 1.2-8.5 units. In another embodiment, the $OD_{600}$ is 1.5-8.5 units. In another embodiment, the $OD_{600}$ is 2-8.5 units. In another embodiment, the $OD_{600}$ is 2.5-8.5 units. In another embodiment, the $OD_{600}$ is 3-8.5 units. In another embodiment, the $OD_{600}$ is 3.5-8.5 units. In another embodiment, the $OD_{600}$ is 4-8.5 units. In another embodiment, the $OD_{600}$ is 4.5-8.5 units. In another embodiment, the $OD_{600}$ is 5-8.5 units. In another embodiment, the $OD_{600}$ is 5.5-8.5 units. In another embodiment, the $OD_{600}$ is 6-8.5 units. In another embodiment, the $OD_{600}$ is 6.5-8.5 units. In another embodiment, the $OD_{600}$ is 7-8.5 units. In another embodiment, the $OD_{600}$ is 7.5-8.5 units. In another embodiment, the $OD_{600}$ is 8-8.5 units. In another embodiment, the $OD_{600}$ is 9.5-8.5 units. In another embodiment, the $OD_{600}$ is 10 units.

In another embodiment, the step of freezing or lyophilization is performed when the culture has a biomass of $1\times10^9$ colony-forming units (CFU)/ml. In another embodiment, the biomass is $1.5\times10^9$ CFR/ml. In another embodiment, the biomass is $1.5\times10^9$ CFR/ml. In another embodiment, the biomass is $2\times10^9$ CFR/ml. In another embodiment, the biomass is $3\times10^9$ CFR/ml. In another embodiment, the biomass is $4\times10^9$ CFR/ml. In another embodiment, the biomass is $5\times10^9$ CFR/ml. In another embodiment, the biomass is $7\times10^9$ CFR/ml. In another embodiment, the biomass is $9\times10^9$ CFR/ml. In another embodiment, the biomass is $10\times10^9$ CFR/ml. In another embodiment, the biomass is $12\times10^9$ CFR/ml. In another embodiment, the biomass is $15\times10^9$ CFR/ml. In another embodiment, the biomass is $20\times10^9$ CFR/ml. In another embodiment, the biomass is $25\times10^9$ CFR/ml. In another embodiment, the biomass is $30\times10^9$ CFR/ml. In another embodiment, the biomass is $33\times10^9$ CFR/ml. In another embodiment, the biomass is $40\times10^9$ CFR/ml. In another embodiment, the biomass is $50\times10^9$ CFR/ml. In another embodiment, the biomass is more than $50\times10^9$ CFR/ml.

Each number and range of $OD_{600}$ readings and culture biomass measurements represents a separate embodiment of the present invention.

In another embodiment of methods and compositions of the present invention, the *Listeria* culture is flash-frozen in liquid nitrogen, followed by storage at the final freezing temperature. In another embodiment, the culture is frozen in a more gradual manner; e.g. by placing in a vial of the culture in the final storage temperature. In another embodiment, the culture is frozen by any other method known in the art for freezing a bacterial culture. Each possibility represents a separate embodiment of the present invention.

In another embodiment of methods and compositions of the present invention, the storage temperature of the culture is between ⁻20 and ⁻80 degrees Celsius (° C.). In another embodiment, the temperature is significantly below ⁻20° C. In another embodiment, the temperature is not warmer than ⁻70° C. In another embodiment, the temperature is ⁻70° C. In another embodiment, the temperature is about ⁻70° C. In another embodiment, the temperature is ⁻20° C. In another embodiment, the temperature is about ⁻20° C. In another embodiment, the temperature is ⁻30° C. In another embodiment, the temperature is ⁻40° C. In another embodiment, the temperature is ⁻50° C. In another embodiment, the temperature is ⁻60° C. In another embodiment, the temperature is ⁻80° C. In another embodiment, the temperature is ⁻30-⁻70° C. In another embodiment, the temperature is ⁻40-⁻70° C. In another embodiment, the temperature is ⁻50-⁻70° C. In another embodiment, the temperature is ⁻60-⁻70° C. In another embodiment, the temperature is ⁻30-⁻80° C. In another embodiment, the temperature is ⁻40-⁻80° C. In another embodiment, the temperature is ⁻50-⁻80° C. In another embodiment, the temperature is ⁻60-⁻80° C. In another embodiment, the temperature is ⁻70-⁻80° C. In another embodiment, the temperature is colder than ⁻70° C. In another embodiment, the temperature is colder than ⁻80° C. Each possibility represents a separate embodiment of the present invention.

In another embodiment of methods and compositions of the present invention, the cryopreservation, frozen storage, or lyophilization is for a maximum of 24 hours. In another embodiment, the cryopreservation, frozen storage, or lyophilization is for maximum of 2 days. In another embodiment, the cryopreservation, frozen storage, or lyophilization is for maximum of 3 days. In another embodiment, the cryopreservation, frozen storage, or lyophilization is for maximum of 4 days. In another embodiment, the cryopreservation, frozen storage, or lyophilization is for maximum of 1 week. In another embodiment, the cryopreservation, frozen storage, or lyophilization is for maximum of 2 weeks. In another embodiment, the cryopreservation, frozen storage, or lyophilization is for maximum of 3 weeks. In another embodiment, the cryopreservation, frozen storage, or lyophilization is for maximum of 1 month. In another embodiment, the cryopreservation, frozen storage, or lyophilization is for maximum of 2 months. In another embodiment, the cryopreservation, frozen storage, or lyophilization is for maximum of 3 months. In another embodiment, the cryopreservation, frozen storage, or lyophilization is for maximum of 5 months. In another embodiment, the cryopreservation, frozen storage, or lyophilization is for maximum of 6 months. In another embodiment, the cryopreservation, frozen storage, or lyophilization is for maximum of 9 months. In another embodiment, the cryopreservation, frozen storage, or lyophilization is for maximum of 1 year.

In another embodiment, the cryopreservation, frozen storage, or lyophilization is for a minimum of 1 week. In another embodiment, the cryopreservation, frozen storage, or lyophilization is for minimum of 2 weeks. In another embodiment, the cryopreservation, frozen storage, or lyophilization is for minimum of 3 weeks. In another embodiment, the cryopreservation, frozen storage, or lyophilization is for minimum of 1 month. In another embodiment, the cryopreservation, frozen storage, or lyophilization is for minimum of 2 months. In another embodiment, the cryopreservation, frozen storage, or lyophilization is for minimum of 3 months. In another embodiment, the cryopreservation, frozen storage, or lyophilization is for minimum of 5 months. In another embodiment, the cryopreservation, frozen storage, or lyophilization is for minimum of 6 months. In another embodiment, the cryopreservation, frozen storage, or lyophilization is for minimum of 9 months. In another embodiment, the cryopreservation, frozen storage, or lyophilization is for minimum of 1 year. In another embodiment, the cryopreservation, frozen storage, or lyophilization is for minimum of 1.5 years. In another embodiment, the cryopreservation, frozen storage, or lyophilization is for minimum of 2 years. In another embodiment, the cryopreservation, frozen storage, or lyophilization is for minimum of 3 years. In another embodiment, the cryopreservation, frozen storage, or lyophilization is for minimum of 5 years. In another embodiment, the cryopreservation, frozen storage, or lyophilization is for minimum of 7 years. In another embodiment, the cryopreservation, frozen storage, or lyophilization is for minimum of 10 years. In another embodiment, the cryopreservation, frozen storage, or lyophilization is for longer than 10 years.

Each length of cryopreservation, frozen storage, or lyophilization represents a separate embodiment of the present invention.

In another embodiment of methods and compositions of the present invention, the *Listeria* bacteria exhibit exponential growth essentially immediately after thawing following an extended period of cryopreservation or frozen storage (Example 14). In another embodiment, the *Listeria* bacteria exhibit exponential growth essentially immediately after reconstitution following an extended period of lyophilization. In another embodiment, "essentially immediately" refers to within about 1 hour after inoculating fresh media with cells from the cell bank or starter culture. In another embodiment, the bacteria exhibit exponential growth shortly after (e.g. in various embodiments, after 10 minutes (min), 20 min, 30 min, 40 min, 50 min, 1 hour, 75 min, 90 min, 105 min, or 2 hours) thawing following the period of cryopreservation or storage. Each possibility represents a separate embodiment of the present invention.

The "extended period" of cryopreservation, frozen storage, or lyophilization is, in another embodiment, 1 month. In another embodiment, the period is 2 months. In another embodiment, the period is 3 months. In another embodiment, the period is 5 months. In another embodiment, the period is 6 months. In another embodiment, the period is 9 months. In another embodiment, the period is 1 year. In another embodiment, the period is 1.5 years. In another embodiment, the period is 2 years. Each possibility represents a separate embodiment of the present invention.

In another embodiment, "exponential growth" refers to a doubling time that is close to the maximum observed for the conditions (e.g. media type, temperature, etc.) in which the culture is growing. In another embodiment, "exponential growth" refers to a doubling time that is reasonable constant several hours (e.g. 1 hour, 1.5 hours, 2 hours, or 2.5 hours) after dilution of the culture; optionally following a brief recovery period. Each possibility represents a separate embodiment of the present invention.

In another embodiment, a *Listeria* vaccine strain of methods and compositions of the present invention retains a viability of over 90% after thawing following 14 days of cryopreservation (Example 14). In another embodiment, the viability upon thawing is close to 100% following the period of cryopreservation. In another embodiment, the viability upon thawing is about 90%. In another embodiment, the viability upon thawing is close to 90%. In another embodiment, the viability upon thawing is at least 90%. In another embodiment, the viability upon thawing is over 80%. Each possibility represents a separate embodiment of the present invention.

In another embodiment, a *Listeria* vaccine strain of methods and compositions of the present invention retains a viability of over 90% after reconstitution following lyophilization. In another embodiment, the viability upon thawing is close to 100% following the period of lyophilization. In another embodiment, the viability upon thawing is about 90%. In another embodiment, the viability upon thawing is close to 90%. In another embodiment, the viability upon thawing is at least 90%. In another embodiment, the viability upon thawing is over 80%. Each possibility represents a separate embodiment of the present invention.

In another embodiment, a cell bank, frozen stock, or batch of vaccine doses of the present invention is grown in a defined microbiological media, comprising: (1) between about 0.3 and about 0.6 g/L of methionine; and (2) effective amounts of: (a) cysteine; (b) a pH buffer; (c) a carbohydrate; (d) a divalent cation; (e) ferric or ferrous ions; (f) glutamine or another nitrogen source; (g) riboflavin; (h) thioctic acid (also known as lipoic acid); (i) another or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.3 and about 0.6 g/L of cysteine; and (2) effective amounts of: (a) methionine; (b) a pH buffer; (c) a carbohydrate; (d) a divalent cation; (e) ferric or ferrous ions; (f) glutamine or another nitrogen source; (g) riboflavin; (h) thioctic acid; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.00123-0.00246 moles of ferric or ferrous ions per liter; and (2) effective amounts of: (a) a pH buffer; (b) a carbohydrate; (c) a divalent cation; (d) methionine; (e) cysteine; (f) glutamine or another nitrogen source; (g) riboflavin; (h) thioctic acid; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 1.8-3.6 g/L of glutamine or another nitrogen source; and (2) effective amounts of: (a) a pH buffer; (b) a carbohydrate: (c) a divalent cation; (d) methionine (e) cysteine; (f) ferric or ferrous ions (g) riboflavin (h); thioctic acid; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 15 and about 30 mg/L of riboflavin; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) thioctic acid; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 0.3 and about 0.6 g/L of thioctic acid; and (2) effective amounts of: (a) a pH buffer; (b) a carbohydrate (c) a divalent cation; (d) methionine (e) cysteine; (f) ferric or ferrous ions; (g) glutamine or another nitrogen source; (h) riboflavin; (i) one or more components selected from leucine, isoleucine, valine, arginine, histidine, tryptophan, and phenylalanine; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; and (6) effective amounts of: (a) a pH buffer; (b) a carbohydrate; (c) a divalent cation; (d) one or more components selected from leucine, isoleucine, valine, arginine, histidine, tryptophan, and phenylalanine; (e) one or more components selected from adenine, biotin, thiamine, pyridoxal, para-aminobenzoic acid, pantothenate, and nicotinamide; and (f) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; and (6) effective amounts of: (a) a pH buffer; (b) a carbohydrate; (c) a divalent cation; (d) leucine; (e) isoleucine; (f) valine; (g) arginine; (h) histidine; (i) tryptophan; (j) phenylalanine; (k) one or more components selected from adenine, biotin, thiamine, pyridoxal, para-aminobenzoic acid, pantothenate, and nicotinamide; and (l) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 0.3 and about 0.6 g/L each of one or more components selected from leucine, isoleucine, valine, arginine, histidine, tryptophan, and phenylalanine; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 0.3 and about 0.6 g/L each of leucine, isoleucine, valine, arginine, histidine, tryptophan, and phenylalanine; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from adenine, biotin, thiamine, pyridoxal, para-aminobenzoic acid, pantothenate, and nicotinamide; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 0.2 and about 0.75 of one or more components selected from biotin and adenine; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; (k) one or more components selected from thiamine, pyridoxal, para-aminobenzoic acid, pantothenate, and nicotinamide; and (l) one or more components selected from cobalt, copper, boron, manganese, molybdenum, zinc, calcium, and citrate.

In another embodiment, the cell bank, frozen stock, or batch of vaccine doses is grown in a defined microbiological media, comprising (1) between about 3 and about 6 mg/L each of one or more components selected from thiamine, pyridoxal, para-aminobenzoic acid, pantothenate, and nicotinamide; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; (k) biotin; (l) adenine; and (l) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.2 and about 0.75 mg/L each of one or more components selected from biotin and adenine; (2) between about 3 and about 6 mg/L each of one or more components selected from thiamine, pyridoxal, para-aminobenzoic acid, pantothenate, and nicotinamide; and (3) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; and (k) one or more components selected from cobalt, copper, boron, manganese, molybdenum, zinc, calcium, and citrate.

In another embodiment, the cell bank, frozen stock, or batch of vaccine doses is grown in a defined microbiological media, comprising: (1) between about 0.005 and about 0.02 g/L each of one or more components selected from cobalt, copper, boron, manganese, molybdenum, zinc, and calcium; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; and (k) one or more components selected from adenine, biotin, thiamine, pyridoxal, para-aminobenzoic acid, pantothenate, and nicotinamide.

In another embodiment, the cell bank, frozen stock, or batch of vaccine doses is grown in a defined microbiological media, comprising: (1) between about 0.4 and about 1 g/L of citrate; and (2) effective amounts of: (a) a pH buffer; (b) a carbohydrate; (c) a divalent cation; (d) methionine; (e) cysteine; (f) ferric or ferrous ions; (g) glutamine or another nitrogen source; (h) riboflavin; (i) thioctic acid; (j) one or more components selected from leucine, isoleucine, valine, arginine, histidine, tryptophan, and phenylalanine; (k) one or more components selected from cobalt, copper, boron, manganese, molybdenum, zinc, and calcium; and (l) one or more components selected from adenine, biotin, thiamine, pyridoxal, para-aminobenzoic acid, pantothenate, and nicotinamide.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; (6) between about 0.3 and about 0.6 g/L each of one or more components selected from leucine, isoleucine, valine, arginine, histidine, tryptophan, and phenylalanine; (7) between about 0.2 and about 0.75 mg/L each of one or more components selected from biotin and adenine; (8) between about 3 and about 6 mg/L each of one or more components selected from thiamine, pyridoxal, para-aminobenzoic acid, pantothenate, and nicotinamide; (9) between about 0.005 and about 0.02 g/L each of one or more components selected from cobalt, copper, boron, manganese, molybdenum, zinc, and calcium; (10) between about 0.4 and about 1 g/L of citrate; and (11) effective amounts of: (a) a pH buffer; (b) a carbohydrate; and (c) a divalent cation.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; (6) between about 0.3 and about 0.6 g/L each of leucine, isoleucine, valine, arginine, histidine, tryptophan, and phenylalanine; (7) between about 0.2 and about 0.75 mg/L each of one or more components selected from biotin and adenine; (8) between about 3 and about 6 mg/L each of one or more components selected from thiamine, pyridoxal, para-aminobenzoic acid, pantothenate, and nicotinamide; (9) between about 0.005 and about 0.02 g/L each of one or more components selected from cobalt, copper, boron, manganese, molybdenum, zinc, and calcium; (10) between about 0.4 and about 1 g/L of citrate; and (11) effective amounts of: (a) a pH buffer; (b) a carbohydrate; and (c) a divalent cation.

In another embodiment, the cell bank, frozen stock, or batch of vaccine doses is grown in a defined microbiological media, comprising: (1) between about 0.3 and about 0.6 g/L each of methionine and cysteine; (2) between about 0.00123 and 0.00246 moles of ferric or ferrous ions per liter; (3) between about 1.8 and about 3.6 g/L of glutamine or another nitrogen source; (4) between about 0.3 and about 0.6 g/L of thioctic acid; (5) between about 15 and about 30 mg/L of riboflavin; (6) between about 0.3 and about 0.6 g/L each of leucine, isoleucine, valine, arginine, histidine, tryptophan, and phenylalanine; (7) between about 0.2 and about 0.75 mg/L each of biotin and adenine; (8) between about 3 and about 6 mg/L each of thiamine, pyridoxal, para-aminobenzoic acid, pantothenate, and nicotinamide; (9) between about 0.005 and about 0.02 g/L each of one or more components selected from cobalt, copper, boron, manganese, molybdenum, zinc, and calcium; (10) between about 0.4 and about 1 g/L of citrate; and (11) and effective amounts of: (a) a pH buffer; (b) a carbohydrate; and (c) a divalent cation.

In another embodiment, a defined microbiological media of the present invention further comprises an aqueous solvent. In another embodiment, the aqueous solvent is water. In another embodiment, the aqueous solvent is any other aqueous solvent known in the art. Each possibility represents a separate embodiment of the present invention.

The carbohydrate utilized in methods and compositions of the present invention is, in another embodiment, glucose. In another embodiment, the carbohydrate is lactose. In another embodiment, the carbohydrate is fructose. In another embodiment, the carbohydrate is mannose. In another embodiment, the carbohydrate is cellobiose. In another embodiment, the carbohydrate is trehalose. In another embodiment, the carbohydrate is maltose. In another embodiment, the carbohydrate is glycerol. In another embodiment, the carbohydrate is glucosamine. In another embodiment, the carbohydrate is N-acetylglucosamine. In another embodiment, the carbohydrate is N-acetylmuramic acid. In another embodiment, the carbohydrate is any other carbohydrate that can be utilized by *Listeria*. Each possibility represents a separate embodiment of the present invention.

In another embodiment, the amount of a carbohydrate present in a defined microbiological media of methods and compositions of the present invention is between about 12-18 grams/liter (g/L). In another embodiment, the amount is 15 g/L. In another embodiment, the amount is 10 g/L. In another embodiment, the amount is 9 g/L. In another embodiment, the amount is 11 g/L. In another embodiment, the amount is 12 g/L. In another embodiment, the amount is 13 g/L. In another embodiment, the amount is 14 g/L. In another embodiment, the amount is 16 g/L. In another embodiment, the amount is 17 g/L. In another embodiment, the amount is 18 g/L. In another embodiment, the amount is 19 g/L. In another embodiment, the amount is 20 g/L. In another embodiment, the amount is more than 20 g/L.

In another embodiment, the amount is 9-15 g/L. In another embodiment, the amount is 10-15 g/L. In another embodiment, the amount is 11-15 g/L. In another embodiment, the amount is 12-16 g/L. In another embodiment, the amount is 13-17 g/L. In another embodiment, the amount is 14-18 g/L. In another embodiment, the amount is 16-19 g/L. In another embodiment, the amount is 17-20 g/L. In another embodiment, the amount is 10-20 g/L. In another embodiment, the amount is 12-20 g/L. In another embodiment, the amount is 15-20 g/L.

In another embodiment, the total amount of carbohydrate in the media is one of the above amounts. In another embodiment, the amount of one of the carbohydrates in the media is one of the above amounts. In another embodiment, the amount of each of the carbohydrates in the media is one of the above amounts.

Each of the above amounts of carbohydrates represents a separate embodiment of the present invention.

The cobalt present in defined microbiological media of methods and compositions of the present invention is, in another embodiment, present as a cobalt ion. In another embodiment, the cobalt is present as a cobalt salt. In another embodiment, the salt is cobalt chloride. In another embodiment, the salt is any other cobalt salt known in the art. In another embodiment, the cobalt is present as any other form of cobalt known in the art.

In another embodiment, the cobalt salt is a hydrate (e.g. cobalt chloride hexahydrate). In another embodiment, the cobalt salt is anhydrous. In another embodiment, the cobalt salt is any other form of a cobalt salt known in the art. Each of the above forms of cobalt represents a separate embodiment of the present invention.

A hydrate of a component of a defined media of methods and compositions of the present invention is, in another embodiment, a monohydrate. In another embodiment, the hydrate is a dihydrate. In another embodiment, the hydrate is a trihydrate. In another embodiment, the hydrate is a tetrahydrate. In another embodiment, the hydrate is a pentahydrate. In another embodiment, the hydrate is a hexahydrate. In another embodiment, the hydrate is a heptahydrate. In another embodiment, the hydrate is any other hydrate known in the art. Each possibility represents a separate embodiment of the present invention.

The copper present in defined microbiological media of methods and compositions of the present invention is, in another embodiment, present as a copper ion. In another embodiment, the copper ion is a copper (I) ion. In another embodiment, the copper ion is a copper (II) ion. In another embodiment, the copper ion is a copper (III) ion.

In another embodiment, the copper is present as a copper salt. In another embodiment, the salt is copper chloride. In another embodiment, the salt is any other copper salt known in the art. In another embodiment, the copper is present as any other form of copper known in the art.

In another embodiment, the copper salt is a hydrate (e.g. copper chloride dihydrate). In another embodiment, the copper salt is anhydrous. In another embodiment, the copper salt is any other form of a copper salt known in the art. Each of the above forms of copper represents a separate embodiment of the present invention.

The boron present in defined microbiological media of methods and compositions of the present invention is, in another embodiment, present as a borate ion. In another embodiment, the boron is present as a borate acid (e.g. boric acid, $H_3BO_3$). In another embodiment, the boron is present as any other form of boron known in the art.

In another embodiment, the borate salt or borate acid is a hydrate. In another embodiment, the borate salt or borate acid is anhydrous. In another embodiment, the borate salt or borate acid is any other form of a borate salt or borate acid known in the art. Each of the above forms of boron represents a separate embodiment of the present invention.

The manganese present in defined microbiological media of methods and compositions of the present invention is, in another embodiment, present as a manganese ion. In another embodiment, the manganese is present as a manganese salt. In another embodiment, the salt is manganese sulfate. In another embodiment, the salt is any other manganese salt known in the art. In another embodiment, the manganese is present as any other form of manganese known in the art.

In another embodiment, the manganese salt is a hydrate (e.g. manganese sulfate monohydrate). In another embodiment, the manganese salt is anhydrous. In another embodiment, the manganese salt is any other form of a manganese salt known in the art. Each of the above forms of manganese represents a separate embodiment of the present invention.

The molybdenum present in defined microbiological media of methods and compositions of the present invention is, in another embodiment, present as a molybdate ion. In another embodiment, the molybdenum is present as a molybdate salt. In another embodiment, the salt is sodium molybdate. In another embodiment, the salt is any other molybdate salt known in the art. In another embodiment, the molybdenum is present as any other form of molybdenum known in the art.

In another embodiment, the molybdate salt is a hydrate (e.g. sodium molybdate dihydrate). In another embodiment, the molybdate salt is anhydrous. In another embodiment, the molybdate salt is any other form of a molybdate salt known in the art. Each of the above forms of molybdenum represents a separate embodiment of the present invention.

The zinc present in defined microbiological media of methods and compositions of the present invention is, in another embodiment, present as a zinc ion. In another embodiment, the zinc is present as a zinc salt. In another embodiment, the salt is zinc chloride. In another embodiment, the salt is any other zinc salt known in the art. In another embodiment, the zinc is present as any other form of zinc known in the art.

In another embodiment, the zinc salt is a hydrate (e.g. zinc chloride heptahydrate). In another embodiment, the zinc salt is anhydrous. In another embodiment, the zinc salt is any other form of a zinc salt known in the art. Each of the above forms of zinc represents a separate embodiment of the present invention.

The iron present in defined microbiological media of methods and compositions of the present invention is, in another embodiment, present as a ferric ion. In another embodiment, the iron is present as a ferrous ion. In another embodiment, the iron is present as a ferric salt. In another embodiment, the iron is present as a ferrous salt. In another embodiment, the salt is ferric sulfate. In another embodiment, the salt is ferric citrate. In another embodiment, the salt is any other ferric salt known in the art. In another embodiment, the salt is any other ferrous salt known in the art. In another embodiment, the iron is present as any other form of iron known in the art.

In another embodiment, the ferric or ferrous salt is a hydrate (e.g. ferric sulfate monohydrate). In another embodiment, the ferric or ferrous salt is anhydrous. In another embodiment, the ferric or ferrous salt is any other form of a ferric or ferrous salt known in the art. Each of the above forms of iron represents a separate embodiment of the present invention.

The calcium present in defined microbiological media of methods and compositions of the present invention is, in another embodiment, present as a calcium ion. In another embodiment, the calcium is present as a calcium salt. In another embodiment, the salt is calcium chloride. In another embodiment, the salt is any other calcium salt known in the art. In another embodiment, the calcium is present as any other form of calcium known in the art.

In another embodiment, the calcium salt is a hydrate (e.g. calcium chloride dihydrate). In another embodiment, the calcium salt is anhydrous. In another embodiment, the calcium salt is any other form of a calcium salt known in the art. Each of the above forms of calcium represents a separate embodiment of the present invention.

The citrate present in defined microbiological media of methods and compositions of the present invention is, in another embodiment, present as a citrate ion. In another embodiment, the citrate is present as a citrate salt. In another embodiment, the citrate is present as a citrate acid (e.g. citric acid). In another embodiment, the citrate is present as both ferric citrate and citric acid (Examples 15-16). In another embodiment, the citrate is present as any other form of citrate known in the art.

In another embodiment, the citrate salt or citrate acid is a hydrate. In another embodiment, the citrate salt or citrate acid is anhydrous. In another embodiment, the citrate salt or citrate acid is any other form of a citrate salt or citrate acid known in the art. Each of the above forms of citrate represents a separate embodiment of the present invention.

The cobalt present in defined microbiological media of methods and compositions of the present invention is, in another embodiment, present in an amount of 0.02 g/L (Examples 15-16). In another embodiment, the amount is about 0.02 g/L. In another embodiment, the amount is 0.003 g/L. In another embodiment, the amount is 0.005 g/L. In another embodiment, the amount is 0.007 g/L. In another embodiment, the amount is 0.01 g/L. In another embodiment, the amount is 0.015 g/L. In another embodiment, the amount is 0.025 g/L. In another embodiment, the amount is 0.03 g/L. In another embodiment, the amount is 0.003-0.006 g/L. In another embodiment, the amount is 0.005-0.01 g/L. In another embodiment, the amount is 0.01-0.02 g/L. In another embodiment, the amount is 0.02-0.04 g/L. In another embodiment, the amount is 0.03-0.06 g/L.

In another embodiment, the cobalt is present in an amount that is the molar equivalent of 0.02 g/L of cobalt chloride hexahydrate. In another embodiment, the amount of cobalt present is the molar equivalent of about 0.02 g/L of cobalt chloride hexahydrate. In another embodiment, the amount of cobalt present is the molar equivalent of another of the above amounts or ranges of cobalt chloride hexahydrate. Each of the above amounts or ranges of cobalt represents a separate embodiment of the present invention.

The copper present in defined microbiological media of methods and compositions of the present invention is, in another embodiment, present in an amount of 0.019 g/L (Examples 15-16). In another embodiment, the amount is about 0.019 g/L. In other embodiments, the amount is any of the amounts or ranges listed above for cobalt.

In another embodiment, the copper is present in an amount that is the molar equivalent of 0.019 g/L of copper chloride dihydrate. In another embodiment, the amount of copper present is the molar equivalent of about 0.019 g/L of copper chloride dihydrate. In another embodiment, the amount of copper present is the molar equivalent of copper chloride dihydrate in any of the amounts or ranges listed above for cobalt. Each of the above amounts or ranges of copper represents a separate embodiment of the present invention.

The borate present in defined microbiological media of methods and compositions of the present invention is, in another embodiment, present in an amount of 0.016 g/L (Examples 15-16). In another embodiment, the amount is about 0.016 g/L. In other embodiments, the amount is any of the amounts or ranges listed above for cobalt.

In another embodiment, the borate is present in an amount that is the molar equivalent of 0.016 g/L of boric acid. In another embodiment, the amount of borate present is the molar equivalent of about 0.016 g/L of boric acid. In another embodiment, the amount of borate present is the molar equivalent of boric acid in any of the amounts or ranges listed above for cobalt. Each of the above amounts or ranges of borate represents a separate embodiment of the present invention.

The manganese present in defined microbiological media of methods and compositions of the present invention is, in another embodiment, present in an amount of 0.016 g/L (Examples 15-16). In another embodiment, the amount is about 0.016 g/L. In other embodiments, the amount is any of the amounts or ranges listed above for cobalt.

In another embodiment, the manganese is present in an amount that is the molar equivalent of 0.016 g/L of manganese sulfate monohydrate. In another embodiment, the amount of manganese present is the molar equivalent of about 0.016 g/L of manganese sulfate monohydrate. In another embodiment, the amount of manganese present is the molar equivalent of manganese sulfate monohydrate in any of the amounts or ranges listed above for cobalt. Each of the above amounts or ranges of manganese represents a separate embodiment of the present invention.

The molybdenum present in defined microbiological media of methods and compositions of the present invention is, in another embodiment, present in an amount of 0.02 g/L (Examples 15-16). In another embodiment, the amount is about 0.02 g/L. In other embodiments, the amount is any of the amounts or ranges listed above for cobalt.

In another embodiment, the molybdenum is present in an amount that is the molar equivalent of 0.2 g/L of sodium molybdate dihydrate. In another embodiment, the amount of molybdenum present is the molar equivalent of about 0.02 g/L of sodium molybdate dihydrate. In another embodiment, the amount of molybdenum present is the molar equivalent of sodium molybdate dihydrate in any of the amounts or ranges listed above for cobalt. Each of the above amounts or ranges of molybdenum represents a separate embodiment of the present invention.

The zinc present in defined microbiological media of methods and compositions of the present invention is, in another embodiment, present in an amount of 0.02 g/L (Examples 15-16). In another embodiment, the amount is about 0.02 g/L. In other embodiments, the amount is any of the amounts or ranges listed above for cobalt.

In another embodiment, the zinc is present in an amount that is the molar equivalent of 0.02 g/L of zinc chloride heptahydrate. In another embodiment, the amount of zinc present is the molar equivalent of about 0.02 g/L of zinc chloride heptahydrate. In another embodiment, the amount of zinc present is the molar equivalent of zinc chloride heptahydrate in any of the amounts or ranges listed above for cobalt. Each of the above amounts or ranges of zinc represents a separate embodiment of the present invention.

In another embodiment, ferric sulfate or a related compound is present in defined microbiological media of methods and compositions of the present invention. In another embodiment, the ferric sulfate or related compound is present in an amount of 0.01 g/L (Examples 15-16). In another embodiment, the amount is about 0.01 g/L. In other embodiments, the amount is any of the amounts or ranges listed above for cobalt.

In another embodiment, the iron is present in an amount that is the molar equivalent of 0.01 g/L of ferric sulfate. In another embodiment, the amount of iron present is the molar equivalent of about 0.01 g/L of ferric sulfate. In another embodiment, the amount of iron present is the molar equivalent of ferric sulfate in any of the amounts or ranges listed above for cobalt. Each of the above amounts or ranges of iron represents a separate embodiment of the present invention.

The calcium present in defined microbiological media of methods and compositions of the present invention is, in another embodiment, present in an amount of 0.01 g/L (Examples 15-16). In another embodiment, the amount is about 0.01 g/L. In other embodiments, the amount is any of the amounts or ranges listed above for cobalt.

In another embodiment, the calcium is present in an amount that is the molar equivalent of 0.01 g/L of calcium chloride dihydrate. In another embodiment, the amount of calcium present is the molar equivalent of about 0.01 g/L of calcium chloride dihydrate. In another embodiment, the amount of calcium present is the molar equivalent of calcium chloride dihydrate in any of the amounts or ranges listed above for cobalt. Each of the above amounts or ranges of calcium represents a separate embodiment of the present invention.

The citrate present in defined microbiological media of methods and compositions of the present invention is, in another embodiment, present in an amount of 0.9 g/L (Examples 15-16). In another embodiment, the amount is 0.6 g/L in the form of citric acid (Examples 15-16). In another embodiment, the amount is 0.4 g/L in the form of ferric citrate (Examples 15-16). In another embodiment, the amount is 0.6 g/L in the form of citric acid and 0.4 g/L in the form of ferric citrate (Examples 15-16). In another embodiment, the amount is about 0.6 g/L. In another embodiment, the amount is 0.1 g/L. In another embodiment, the amount is 0.2 g/L. In another embodiment, the amount is 0.3 g/L. In another embodiment, the amount is 0.4 g/L. In another embodiment, the amount is 0.5 g/L. In another embodiment, the amount is 0.7 g/L. In another embodiment, the amount is 0.8 g/L. In another embodiment, the amount is 1 g/L. In another embodiment, the amount is more than 1 g/L.

In another embodiment, the citrate is present in an amount that is the molar equivalent of 0.6 g/L of citric acid. In another embodiment, the amount of citrate present is the molar equivalent of about 0.6 g/L of citric acid. In another embodiment, the amount of citrate present is the molar equivalent of about 0.4 g/L of ferric citrate. In another embodiment, the amount of citrate present is the molar equivalent of 0.4 g/L of ferric citrate. In another embodiment, the amount of citrate present is the molar equivalent of 0.6 g/L of citric acid and 0.4 g/L of ferric citrate. In another embodiment, the amount of citrate present is the about molar equivalent of 0.6 g/L of citric acid and 0.4 g/L of ferric citrate. In another embodiment, the amount of citrate present is the molar equivalent of citric acid in any of the amounts or ranges listed above for citrate. Each of the above amounts or ranges of citrate represents a separate embodiment of the present invention.

One or more of the adenine, biotin, thiamine, pyridoxal, para-aminobenzoic acid, pantothenate, and nicotinamide present in defined microbiological media of methods and compositions of the present invention are, in another embodiment, present as the free compound. In another embodiment, one of the above compounds is present as a salt thereof. In another embodiment, one of the above compounds is present as a derivative thereof. In another embodiment, one of the above compounds is present as a hydrate thereof. In other embodiments, the salt, derivative, or hydrate can be any salt, derivative, or hydrate known in the art. Each of the above forms of adenine, biotin, thiamine, pyridoxal, para-aminobenzoic acid, pantothenate, and nicotinamide represents a separate embodiment of the present invention.

The thiamine (vitamin B1) present in defined microbiological media of methods and compositions of the present invention is, in another embodiment, present in the form of thiamine HCl. In another embodiment, the thiamine is present as any other salt, derivative, or hydrate of thiamine known in the art. In another embodiment, another form of vitamin B1 is substituted for thiamine. Each possibility represents a separate embodiment of the present invention.

In another embodiment, the thiamine is present in an amount of 4 mg/L (Examples 15-16). In another embodiment, the amount is about 0.5 mg/L. In another embodiment, the amount is 0.7 mg/L. In another embodiment, the amount is 1 mg/L. In another embodiment, the amount is 1.5 mg/L. In another embodiment, the amount is 2 mg/L. In another embodiment, the amount is 3 mg/L. In another embodiment, the amount is 5 mg/L. In another embodiment, the amount is 6 mg/L. In another embodiment, the amount is 8 mg/L. In another embodiment, the amount is more than 8 mg/L. In another embodiment, the thiamine is present in an amount that is the molar equivalent of 4 mg/L of thiamine HCl. In another embodiment, the thiamine is present in an amount that is the molar equivalent of thiamine HCl in one of the above amounts. Each possibility represents a separate embodiment of the present invention.

The pyridoxal (vitamin B6) present in defined microbiological media of methods and compositions of the present invention is, in another embodiment, present in the form of pyridoxal HCl. In another embodiment, the pyridoxal is present as any other salt, derivative, or hydrate of pyridoxal known in the art. In another embodiment, another form of vitamin B6 is substituted for pyridoxal. Each possibility represents a separate embodiment of the present invention.

In another embodiment, the pyridoxal is present in an amount of 4 mg/L (Examples 15-16). In another embodiment, the amount is any of the amounts or ranges listed above for thiamine. In another embodiment, the amount of pyridoxal present is the molar equivalent of about 4 mg/L of pyridoxal HCl. In another embodiment, the amount of pyridoxal present is the molar equivalent of pyridoxal HCl in any of the amounts or ranges listed above for thiamine. Each possibility represents a separate embodiment of the present invention.

The adenine (vitamin B4) present in defined microbiological media of methods and compositions of the present invention is, in another embodiment, present in the form of free adenine. In another embodiment, the adenine is present as any other salt, derivative, or hydrate of adenine known in the art. In another embodiment, another form of vitamin B4 is substituted for adenine. Each possibility represents a separate embodiment of the present invention.

In another embodiment, the adenine is present in an amount of 0.25 mg/L (Examples 15-16). In another embodiment, the amount is any of the amounts or ranges listed above for cobalt. In another embodiment, the amount of adenine present is the molar equivalent of about 0.25 mg/L of free adenine. In another embodiment, the amount of adenine present is the molar equivalent of free adenine in any of the amounts or ranges listed above for cobalt. Each possibility represents a separate embodiment of the present invention.

The biotin (vitamin B7) present in defined microbiological media of methods and compositions of the present invention is, in another embodiment, present in the form of free biotin. In another embodiment, the biotin is present as any other salt, derivative, or hydrate of biotin known in the art. In another embodiment, another form of vitamin B7 is substituted for biotin. Each possibility represents a separate embodiment of the present invention.

In another embodiment, the biotin is present in an amount of 2 mg/L (Examples 15-16). In another embodiment, the amount is any of the amounts or ranges listed above for thiamine. In another embodiment, the amount of biotin present is the molar equivalent of about 2 mg/L of free biotin.

In another embodiment, the amount of biotin present is the molar equivalent of free biotin in any of the amounts or ranges listed above for thiamine. Each possibility represents a separate embodiment of the present invention.

The para-aminobenzoic acid (vitamin B-x) present in defined microbiological media of methods and compositions of the present invention is, in another embodiment, present in the form of free para-aminobenzoic acid. In another embodiment, the para-aminobenzoic acid is present as any other salt, derivative, or hydrate of para-aminobenzoic acid known in the art. In another embodiment, another form of vitamin B-x is substituted for para-aminobenzoic acid. Each possibility represents a separate embodiment of the present invention.

In another embodiment, the para-aminobenzoic acid is present in an amount of 4 mg/L (Examples 15-16). In another embodiment, the amount is any of the amounts or ranges listed above for thiamine. In another embodiment, the amount of para-aminobenzoic acid present is the molar equivalent of about 4 mg/L of free para-aminobenzoic acid. In another embodiment, the amount of para-aminobenzoic acid present is the molar equivalent of free para-aminobenzoic acid in any of the amounts or ranges listed above for thiamine. Each possibility represents a separate embodiment of the present invention.

The pantothenate (vitamin B5) present in defined microbiological media of methods and compositions of the present invention is, in another embodiment, present in the form of calcium pantothenate. In another embodiment, the pantothenate is present as any other salt, derivative, or hydrate of pantothenate known in the art. In another embodiment, another form of vitamin B5 is substituted for pantothenate. Each possibility represents a separate embodiment of the present invention.

In another embodiment, the pantothenate is present in an amount of 4 mg/L (Examples 15-16). In another embodiment, the amount is any of the amounts or ranges listed above for thiamine. In another embodiment, the amount of pantothenate present is the molar equivalent of about 4 mg/L of calcium pantothenate. In another embodiment, the amount of pantothenate present is the molar equivalent of calcium pantothenate in any of the amounts or ranges listed above for thiamine. Each possibility represents a separate embodiment of the present invention.

The nicotinamide (vitamin B3) present in defined microbiological media of methods and compositions of the present invention is, in another embodiment, present in the form of free nicotinamide. In another embodiment, the nicotinamide is present as any other salt, derivative, or hydrate of nicotinamide known in the art. In another embodiment, another form of vitamin B3 is substituted for nicotinamide. Each possibility represents a separate embodiment of the present invention.

In another embodiment, the nicotinamide is present in an amount of 4 mg/L (Examples 15-16). In another embodiment, the amount is any of the amounts or ranges listed above for thiamine. In another embodiment, the amount of nicotinamide present is the molar equivalent of about 4 mg/L of free nicotinamide. In another embodiment, the amount of nicotinamide present is the molar equivalent of free nicotinamide in any of the amounts or ranges listed above for thiamine. Each possibility represents a separate embodiment of the present invention.

One or more of the leucine, isoleucine, valine, arginine, histidine, tryptophan, and phenylalanine present in defined microbiological media of methods and compositions of the present invention are, in another embodiment, present as free amino acids. In another embodiment, one of the above compounds is present as a salt thereof. In another embodiment, one of the above compounds is present as a derivative thereof. In another embodiment, one of the above compounds is present as a hydrate thereof. In other embodiments, the salt, derivative, or hydrate can be any salt, derivative, or hydrate known in the art. Each of the above forms of adenine, biotin, thiamine, pyridoxal, para-aminobenzoic acid, pantothenate, and nicotinamide represents a separate embodiment of the present invention.

In another embodiment, one or more of the leucine, isoleucine, valine, arginine, histidine, tryptophan, and phenylalanine is present in an amount of 0.4 g/L (Examples 15-16). In another embodiment, the amount is about 0.05 g/L. In another embodiment, the amount is 0.07 g/L. In another embodiment, the amount is 0.1 g/L. In another embodiment, the amount is 0.15 g/L. In another embodiment, the amount is 0.2 g/L. In another embodiment, the amount is 0.3 g/L. In another embodiment, the amount is 0.5 g/L. In another embodiment, the amount is 0.6 g/L. In another embodiment, the amount is 0.8 g/L. In another embodiment, the amount is more than 0.8 g/L. In another embodiment, one or more of these AA is present in an amount that is the molar equivalent of 0.4 g/L of the free AA. In another embodiment, the amount is the molar equivalent of thiamine the free AA in one of the above amounts. Each possibility represents a separate embodiment of the present invention.

In another embodiment, a defined media of methods and compositions of the present invention contains two of the amino acids (AA) listed in the second section of Table 3B, e.g. leucine, isoleucine, valine, arginine, histidine, tryptophan, and phenylalanine. In another embodiment, the defined media contains 3 of these AA. In another embodiment, the media contains 4 of these AA. In another embodiment, the media contains 3 of these AA. In another embodiment, the media contains 5 of these AA. In another embodiment, the media contains 6 of these AA. In another embodiment, the media contains all of these AA. In another embodiment, the media contains at least 2 of these AA. In another embodiment, the media contains at least 3 of these AA. In another embodiment, the media contains at least 4 of these AA. In another embodiment, the media contains at least 5 of these AA. In another embodiment, the media contains at least 6 of these AA. Each possibility represents a separate embodiment of the present invention.

In another embodiment, a defined media of methods and compositions of the present invention contains 2 of the vitamins listed in the third section of Table 3B, e.g. adenine, biotin, thiamine, pyridoxal, para-aminobenzoic acid, pantothenate, and nicotinamide. In another embodiment, the defined media contains 3 of these vitamins. In another embodiment, the media contains 4 of these vitamins. In another embodiment, the media contains 3 of these vitamins. In another embodiment, the media contains 5 of these vitamins. In another embodiment, the media contains 6 of these vitamins. In another embodiment, the media contains all of these vitamins. In another embodiment, the media contains at least 2 of these vitamins. In another embodiment, the media contains at least 3 of these vitamins. In another embodiment, the media contains at least 4 of these vitamins. In another embodiment, the media contains at least 5 of these vitamins. In another embodiment, the media contains at least 6 of these vitamins. Each possibility represents a separate embodiment of the present invention.

In another embodiment, a defined media of methods and compositions of the present invention contains 2 of the trace elements listed in the fourth section of Table 3B, e.g. cobalt, copper, boron, manganese, molybdenum, zinc, iron, calcium, and citrate. In another embodiment, the defined media contains 3 of these trace elements. In another embodiment, the media contains 4 of these trace elements. In another embodiment, the media contains 3 of these trace elements. In another embodiment, the media contains 5 of these trace elements. In another embodiment, the media contains 6 of these trace elements. In another embodiment, the media contains 7 of these trace elements. In another embodiment, the media contains 7 of these trace elements. In another embodiment, the media contains all of these trace elements. In another embodiment, the media contains at least 2 of these trace elements. In another embodiment, the media contains at least 3 of these trace elements. In another embodiment, the media contains at least 4 of these trace elements. In another embodiment, the media contains at least 5 of these trace elements. In another embodiment, the media contains at least 6 of these trace elements. In another embodiment, the media contains at least 7 of these trace elements. In another embodiment, the media contains at least 8 of these trace elements. Each possibility represents a separate embodiment of the present invention.

In another embodiment, a defined media of methods and compositions of the present invention contains more than 1 component from 2 of the above classes of components; e.g more than one of the AA listed in the second section of Table 3B, and more than one of the vitamins listed in the third section. In another embodiment, the media contains more than 2 components from 2 of the above classes of components; e.g more than 2 of the AA listed in the second section of Table 3B, and more than 2 of the trace elements listed in the fourth section. In another embodiment, the media contains more than 3 components from 2 of the above classes. In another embodiment, the media contains more than 4 components from 2 of the above classes. In another embodiment, the media contains more than 5 components from 2 of the above classes. In another embodiment, the media contains more than 6 components from 2 of the above classes. In another embodiment, the media contains all of the components from 2 of the above classes.

In another embodiment, a defined media of methods and compositions of the present invention contains more than 1 component from all of the above classes of components (e.g. more than 1 component each from AA, vitamins and trace elements). In another embodiment, the media contains more than 2 components from all of the above classes of components. In another embodiment, the media contains more than 3 components from all of the above classes. In another embodiment, the media contains more than 4 components from all of the above classes. In another embodiment, the media contains more than all components from 2 of the above classes. In another embodiment, the media contains more than 6 components from all of the above classes. In another embodiment, the media contains all of the components from all of the above classes.

In another embodiment, the media contains any other combination of numbers of components from each of the above classes; e.g. 2 AA, 2 vitamins, and 3 trace elements; 3 AA, 3 vitamins, and 2 trace elements; 2 AA, 3 vitamins, and all of the trace elements, etc.

Each of the above combinations of numbers of components from each of the above classes represents a separate embodiment of the present invention.

In another embodiment, a defined media of methods and compositions of the present invention consists of one of the above recipes, mixtures of components, lists of components in specified amounts, or combinations of numbers of components from each of the above classes. Each possibility represents a separate embodiment of the present invention.

The divalent cation present in defined microbiological media of methods and compositions of the present invention is, in another embodiment, Mg. In another embodiment, the divalent cation is Ca. In another embodiment, the divalent cation is any other divalent cation known in the art. Mg can, in other embodiments, be present in any form of Mg known in the art, e.g. $MgSO_4$ (Examples 15-16). In another embodiment, the divalent cation is present in an amount that is the molar equivalent of about 0.41 g/mL. In other embodiments, the divalent cation is present in another effective amount, as known to those skilled in the art.

In another embodiment, a nitrogen source other than glutamine is utilized in defined media of the present invention. In another embodiment, the nitrogen source is another AA. In another embodiment, the nitrogen source is another source of peptides or proteins (e.g. casitone or casamino acids). In another embodiment, the nitrogen source is ammonium chloride. In another embodiment, the nitrogen source is ammonium nitrate. In another embodiment, the nitrogen source is ammonium sulfate. In another embodiment, the nitrogen source is another ammonium salt. In another embodiment, the nitrogen source is any other nitrogen source known in the art. Each possibility represents a separate embodiment of the present invention.

In another embodiment, a defined microbiological media of methods and compositions of the present invention does not contain a component derived from an animal source. In another embodiment, the defined microbiological media does not contain an animal-derived component of incompletely defined composition (e.g. yeast extract, bacto-tryptone, etc.). Each possibility represents a separate embodiment of the present invention.

In another embodiment, "defined microbiological media" refers to a media whose components are known. In another embodiment, the term refers to a media that does not contain a component derived from an animal source. In another embodiment, the term refers to a media whose components have been chemically characterized. Each possibility represents a separate embodiment of the present invention.

In another embodiment, a defined media of methods and compositions of the present invention supports growth of the *Listeria* strain to about $1.1 \times 10^{10}$ CFU/mL (e.g. when grown in flasks; Examples 13-16). In another embodiment, the defined media supports growth to about $1.1 \times 10^{10}$ CFU/mL (e.g. when grown in fermenters; Examples 13-16). In another embodiment, the defined media supports growth to about $5 \times 10^9$ CFU/mL (e.g. when grown in fermenters; Examples 13-16). In another embodiment, the defined media supports growth of viable bacteria (e.g. bacteria that can be cryopreserved without significant loss of viability) to about $3 \times 10^{10}$ CFU/mL (e.g. when grown in fermenters; Examples 13-16). In another embodiment, the defined media supports growth to an $OD_{600}$ of about 4.5 (Examples 13-16). In other embodiments, the defined media supports growth to another $OD_{600}$ value enumerated herein. In other embodiments, the defined media supports growth to another CFU/mL value enumerated herein. In another embodiment, the defined media supports growth to a density approximately equivalent to that obtained with TB. In another embodiment, the defined media supports growth to a density approximately equivalent to that obtained with LB. Each possibility represents a separate embodiment of the present invention.

In another embodiment, a defined media of methods and compositions of the present invention supports a growth rate of the *Listeria* strain of about 0.25 $h^{-1}$ (Examples). In another embodiment, the growth rate is about 0.15 $h^{-1}$. In another embodiment, the growth rate is about 0.2 $h^{-1}$. In another embodiment, the growth rate is about 0.3 h⁻¹. In another embodiment, the growth rate is about 0.4 h⁻¹. In another embodiment, the growth rate is about 0.5 h⁻¹. In another embodiment, the growth rate is about 0.6 h⁻¹. In another embodiment, the defined media supports a growth rate approximately equivalent to that obtained with TB. In another embodiment, the defined media supports a growth rate approximately equivalent to that obtained with LB. Each possibility represents a separate embodiment of the present invention.

As provided herein, vaccines of the present invention were completely well tolerated in 5/6 patients, even though the patients were very sick with metastatic cancer. It should be noted that halting of therapy in the case of the other patient, Patient 5, was done purely as a precaution. At no point was the patient's life considered to be even remotely in danger. The safety results in such patients, at least some of which were likely to be immunosuppressed, shows that the Listeria vaccines can be safely administered to a wide variety of patients.

In another embodiment, a peptide of the present invention is a fusion peptide. In another embodiment, "fusion peptide" refers to a peptide or polypeptide comprising 2 or more proteins linked together by peptide bonds or other chemical bonds. In another embodiment, the proteins are linked together directly by a peptide or other chemical bond. In another embodiment, the proteins are linked together with 1 or more AA (e.g. a "spacer") between the 2 or more proteins. Each possibility represents a separate embodiment of the present invention.

In another embodiment, a vaccine of the present invention further comprises an adjuvant. The adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

In another embodiment, a nucleotide of the present invention is operably linked to a promoter/regulatory sequence that drives expression of the encoded peptide in the Listeria strain. Promoter/regulatory sequences useful for driving constitutive expression of a gene are well known in the art and include, but are not limited to, for example, the $P_{hlyA}$, $P_{ActA}$, and p60 promoters of Listeria, the Streptococcus bac promoter, the Streptomyces griseus sgiA promoter, and the B. thuringiensis phaZ promoter. In another embodiment, inducible and tissue specific expression of the nucleic acid encoding a peptide of the present invention is accomplished by placing the nucleic acid encoding the peptide under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the invention includes the use of any promoter/regulatory sequence, which is either known or unknown, and which is capable of driving expression of the desired protein operably linked thereto.

In another embodiment of methods and compositions of the present invention, a PEST-like AA sequence is fused to the E7 or E6 antigen. As provided herein, recombinant Listeria strains expressing PEST-like sequence-antigen fusions induce anti-tumor immunity (Example 3) and generate antigen-specific, tumor-infiltrating T cells (Example 4). Further, enhanced cell mediated immunity was demonstrated for fusion proteins comprising an antigen and LLO containing the PEST-like AA sequence KENSISSMAPPASPPASPKT-PIEKKHADEIDK (SEQ ID NO: 1).

Thus, fusion of an antigen to other LM PEST-like sequences and PEST-like sequences derived from other prokaryotic organisms will also enhance immunogenicity of the antigen. The PEST-like AA sequence has, in another embodiment, a sequence selected from SEQ ID NO: 2-7. In another embodiment, the PEST-like sequence is KTE-EQPSEVNTGPR (SEQ ID NO: 2), KASVTDTSEG-DLDSSMQSADESTPQPLK (SEQ ID NO: 3), KNEEVNASDFPPPPTDEELR (SEQ ID NO: 4), or RGGIPTSEEFSSLNSGDFTDDENSETTEEEIDR (SEQ ID NO: 5). In another embodiment, the PEST-like sequence is from Streptolysin O protein of Streptococcus sp. In another embodiment, the PEST-like sequence is from Streptococcus pyogenes Streptolysin O, e.g. KQNTASTETTTTNEQPK (SEQ ID NO: 6) at AA 35-51. In another embodiment, the PEST-like sequence is from Streptococcus equisimilis Streptolysin 0, e.g. KQNTANTETTTTNEQPK (SEQ ID NO: 7) at AA 38-54. In another embodiment, the PEST-like sequence is another PEST-like AA sequence derived from a prokaryotic organism. In another embodiment, the PEST-like sequence is any other PEST-like sequence known in the art. Each possibility represents a separate embodiment of the present invention.

PEST-like sequences of other prokaryotic organism can be identified in accordance with methods such as described by, for example Rechsteiner and Rogers (1996, Trends Biochem. Sci. 21:267-271) for LM. Alternatively, PEST-like AA sequences from other prokaryotic organisms can also be identified based by this method. Other prokaryotic organisms wherein PEST-like AA sequences would be expected to include, but are not limited to, other Listeria species. In another embodiment, the PEST-like sequence is embedded within the antigenic protein. Thus, in another embodiment, "fusion" refers to an antigenic protein comprising both the antigen and the PEST-like amino acid sequence either linked at one end of the antigen or embedded within the antigen.

In another embodiment, the PEST-like sequence is identified using any other method or algorithm known in the art, e.g the CaSPredictor (Garay-Malpartida H M, Occhiucci J M, Alves J, Belizario J E. Bioinformatics. 2005 June; 21 Suppl 1:1169-76). In another embodiment, the following method is used:

A PEST index is calculated for each 30-35 AA stretch by assigning a value of 1 to the amino acids Ser, Thr, Pro, Glu, Asp, Asn, or Gln. The coefficient value (CV) for each of the PEST residue is 1 and for each of the other AA (non-PEST) is 0.

Each method for identifying a PEST-like sequence represents a separate embodiment of the present invention.

In another embodiment, the LLO protein, or fragment thereof of the present invention need not be that which is set forth exactly in the sequences set forth herein, but rather other alterations, modifications, or changes can be made that retain the functional characteristics of an LLO protein fused to an antigen as set forth elsewhere herein. In another embodiment, the present invention utilizes an analog of an LLO protein, or fragment thereof. Analogs differ, in another embodiment, from naturally occurring proteins or peptides by conservative AA sequence differences or by modifications which do not affect sequence, or by both.

In another embodiment, either a whole E7 protein or a fragment thereof is fused to a LLO protein, to generate a recombinant peptide of methods of the present invention. The E7 protein that is utilized (either whole or as the source of the fragments) has, in another embodiment, the sequence
MHGDTPTLHEYMLDLQPETTDLY-CYEQLNDSSEEEDEIDGPAGQAEPDRAHY NIVTFC-CKCDSTLRLCVQSTHVDIRTLEDLL-MGTLGIVCPICSQKP (SEQ ID No: 20). In another embodiment, the E7 protein is a homologue of SEQ ID No: 20. In another embodiment, the E7 protein is a variant of SEQ ID No: 20. In another embodiment, the E7 protein is an isomer of SEQ ID No: 20. In another embodiment, the E7 protein is a fragment of SEQ ID No: 20. In another embodiment, the E7 protein is a fragment of a homologue of SEQ ID No: 20. In another embodiment, the E7 protein is a fragment of a variant of SEQ ID No: 20. In another embodiment, the E7 protein is a fragment of an isomer of SEQ ID No: 20. Each possibility represents a separate embodiment of the present invention.

In another embodiment, the sequence of the E7 protein is:
MHGPKATLQDIVLHLEPQ-NEIPVDLLCHEQLSDSEEENDEIDGVNHQHLPARR AEPQRHTMLCMCCKCEARIELVVESSAD-DLRAFQQLFLNTLSFVCPWCASQQ (SEQ ID No: 21). In another embodiment, the E6 protein is a homologue of SEQ ID No: 21. In another embodiment, the E6 protein is a variant of SEQ ID No: 21. In another embodiment, the E6 protein is an isomer of SEQ ID No: 21. In another embodiment, the E6 protein is a fragment of SEQ ID No: 21. In another embodiment, the E6 protein is a fragment of a homologue of SEQ ID No: 21. In another embodiment, the E6 protein is a fragment of a variant of SEQ ID No: 21. In another embodiment, the E6 protein is a fragment of an isomer of SEQ ID No: 21. Each possibility represents a separate embodiment of the present invention.

In another embodiment, the E7 protein has a sequence set forth in one of the following GenBank entries: M24215, NC_004500, V01116, X62843, or M14119. In another embodiment, the E7 protein is a homologue of a sequence from one of the above GenBank entries. In another embodiment, the E7 protein is a variant of a sequence from one of the above GenBank entries. In another embodiment, the E7 protein is an isomer of a sequence from one of the above GenBank entries. In another embodiment, the E7 protein is a fragment of a sequence from one of the above GenBank entries. In another embodiment, the E7 protein is a fragment of a homologue of a sequence from one of the above GenBank entries. In another embodiment, the E7 protein is a fragment of a variant of a sequence from one of the above GenBank entries. In another embodiment, the E7 protein is a fragment of an isomer of a sequence from one of the above GenBank entries. Each possibility represents a separate embodiment of the present invention.

In another embodiment, either a whole E6 protein or a fragment thereof is fused to a LLO protein, to generate a recombinant peptide of methods of the present invention. The E6 protein that is utilized (either whole or as the source of the fragments) has, in another embodiment, the sequence
MHQKRTAMFQDPQERPRKLPQLCTELQT-TIHDIILECVYCKQQLLRREVYDFA FRDL-CIVYRDGNPYAVCDKCLKFYSKISEY-RHYCYSLYGTTLEQQYNKPLCDLLIRCI NCQKPLCPEEKQRHLDKKQRFHNIRGR-WTGRCMSCCRSSRTRRETQL (SEQ ID No: 22). In another embodiment, the E6 protein is a homologue of SEQ ID No: 22. In another embodiment, the E6 protein is a variant of SEQ ID No: 22. In another embodiment, the E6 protein is an isomer of SEQ ID No: 22. In another embodiment, the E6 protein is a fragment of SEQ ID No: 22. In another embodiment, the E6 protein is a fragment of a homologue of SEQ ID No: 22. In another embodiment, the E6 protein is a fragment of a variant of SEQ ID No: 22. In another embodiment, the E6 protein is a fragment of an isomer of SEQ ID No: 22. Each possibility represents a separate embodiment of the present invention.

In another embodiment, the sequence of the E6 protein is:
MARFEDPTRRPYKLP-DLCTELNTSLQDIEITCVYCKTV-LELTEVFEFAFKDLFV VYRDSIPHAACHKCIDFYSR-IRELRHYSDSVYGDTLEKLTNTGLYNLLIRCLRCQKPL NPAEKLRHLNEKRRFHNIAGHYRGQCH-SCCNRARQERLQRRRETQV (SEQ ID No: 23). In another embodiment, In another embodiment, the E6 protein is a homologue of SEQ ID No: 23. In another embodiment, the E6 protein is a variant of SEQ ID No: 23. In another embodiment, the E6 protein is an isomer of SEQ ID No: 23. In another embodiment, the E6 protein is a fragment of SEQ ID No: 23. In another embodiment, the E6 protein is a fragment of a homologue of SEQ ID No: 23. In another embodiment, the E6 protein is a fragment of a variant of SEQ ID No: 23. In another embodiment, the E6 protein is a fragment of an isomer of SEQ ID No: 23. Each possibility represents a separate embodiment of the present invention.

In another embodiment, the E6 protein has a sequence set forth in one of the following GenBank entries: M24215, M14119, NC_004500, V01116, X62843, or M14119. In another embodiment, the E6 protein is a homologue of a sequence from one of the above GenBank entries. In another embodiment, the E6 protein is a variant of a sequence from one of the above GenBank entries. In another embodiment, the E6 protein is an isomer of a sequence from one of the above GenBank entries. In another embodiment, the E6 protein is a fragment of a sequence from one of the above GenBank entries. In another embodiment, the E6 protein is a fragment of a homologue of a sequence from one of the above GenBank entries. In another embodiment, the E6 protein is a fragment of a variant of a sequence from one of the above GenBank entries. In another embodiment, the E6 protein is a fragment of an isomer of a sequence from one of the above GenBank entries. Each possibility represents a separate embodiment of the present invention.

In another embodiment, "homology" refers to identity to an LLO sequence (e.g. to one of SEQ ID No: 15-17) of greater than 70%. In another embodiment, "homology" refers to identity to one of SEQ ID No: 15-17 of greater than 72%. In another embodiment, "homology" refers to identity to one of SEQ ID No: 15-17 of greater than 75%. In another embodiment, "homology" refers to identity to one of SEQ ID No: 15-17 of greater than 78%. In another embodiment, "homology" refers to identity to one of SEQ ID No: 15-17 of greater than 80%. In another embodiment, "homology" refers to identity to one of SEQ ID No: 15-17 of greater than 82%. In another embodiment, "homology" refers to identity to one of SEQ ID No: 15-17 of greater than 83%. In another embodiment, "homology" refers to identity to one of SEQ ID No: 15-17 of greater than 85%. In another embodiment, "homology" refers to identity to one of SEQ ID No: 15-17 of greater than 87%. In another embodiment, "homology" refers to identity to one of SEQ ID No: 15-17 of greater than 88%. In another embodiment, "homology" refers to identity to one of SEQ ID No: 15-17 of greater than 90%. In another embodiment, "homology" refers to identity to one of SEQ ID No: 15-17 of greater than 92%. In another embodiment, "homology" refers to identity to one of SEQ ID No: 15-17 of greater than 93%. In another embodiment, "homology" refers to identity to one of SEQ ID No: 15-17 of greater than 95%. In another embodiment, "homology" refers to identity to one of SEQ ID No: 15-17 of greater than 96%. In another embodiment, "homology" refers to identity to one of SEQ ID No: 15-17 of greater than 97%. In another embodiment, "homology" refers to identity to one of SEQ ID No: 15-17 of greater than 98%. In another embodiment, "homology" refers to identity to one of SEQ ID No: 15-17 of greater than 99%. In another embodiment, "homology" refers to identity to one of SEQ ID No: 15-17 of 100%. Each possibility represents a separate embodiment of the present invention.

In another embodiment, "homology" refers to identity to an E7 sequence (e.g. to one of SEQ ID No: 20-21) of greater than 70%. In another embodiment, "homology" refers to identity to one of SEQ ID No: 20-21 of greater than 72%. In another embodiment, "homology" refers to identity to one of SEQ ID No: 20-21 of greater than 75%. In another embodiment, "homology" refers to identity to one of SEQ ID No: 20-21 of greater than 78%. In another embodiment, "homology" refers to identity to one of SEQ ID No: 20-21 of greater than 80%. In another embodiment, "homology" refers to identity to one of SEQ ID No: 20-21 of greater than 82%. In another embodiment, "homology" refers to identity to one of SEQ ID No: 20-21 of greater than 83%. In another embodiment, "homology" refers to identity to one of SEQ ID No: 20-21 of greater than 85%. In another embodiment, "homology" refers to identity to one of SEQ ID No: 20-21 of greater than 87%. In another embodiment, "homology" refers to identity to one of SEQ ID No: 20-21 of greater than 88%. In another embodiment, "homology" refers to identity to one of SEQ ID No: 20-21 of greater than 90%. In another embodiment, "homology" refers to identity to one of SEQ ID No: 20-21 of greater than 92%. In another embodiment, "homology" refers to identity to one of SEQ ID No: 20-21 of greater than 93%. In another embodiment, "homology" refers to identity to one of SEQ ID No: 20-21 of greater than 95%. In another embodiment, "homology" refers to identity to one of SEQ ID No: 20-21 of greater than 96%. In another embodiment, "homology" refers to identity to one of SEQ ID No: 20-21 of greater than 97%. In another embodiment, "homology" refers to identity to one of SEQ ID No: 20-21 of greater than 98%. In another embodiment, "homology" refers to identity to one of SEQ ID No: 20-21 of greater than 99%. In another embodiment, "homology" refers to identity to one of SEQ ID No: 20-21 of 100%. Each possibility represents a separate embodiment of the present invention.

In another embodiment, "homology" refers to identity to an E6 sequence (e.g. to one of SEQ ID No: 22-23) of greater than 70%. In another embodiment, "homology" refers to identity to one of SEQ ID No: 22-23 of greater than 72%. In another embodiment, "homology" refers to identity to one of SEQ ID No: 22-23 of greater than 75%. In another embodiment, "homology" refers to identity to one of SEQ ID No: 22-23 of greater than 78%. In another embodiment, "homology" refers to identity to one of SEQ ID No: 22-23 of greater than 80%. In another embodiment, "homology" refers to identity to one of SEQ ID No: 22-23 of greater than 82%. In another embodiment, "homology" refers to identity to one of SEQ ID No: 22-23 of greater than 83%. In another embodiment, "homology" refers to identity to one of SEQ ID No: 22-23 of greater than 85%. In another embodiment, "homology" refers to identity to one of SEQ ID No: 22-23 of greater than 87%. In another embodiment, "homology" refers to identity to one of SEQ ID No: 22-23 of greater than 88%. In another embodiment, "homology" refers to identity to one of SEQ ID No: 22-23 of greater than 90%. In another embodiment, "homology" refers to identity to one of SEQ ID No: 22-23 of greater than 92%. In another embodiment, "homology" refers to identity to one of SEQ ID No: 22-23 of greater than 93%. In another embodiment, "homology" refers to identity to one of SEQ ID No: 22-23 of greater than 95%. In another embodiment, "homology" refers to identity to one of SEQ ID No: 22-23 of greater than 96%. In another embodiment, "homology" refers to identity to one of SEQ ID No: 22-23 of greater than 97%. In another embodiment, "homology" refers to identity to one of SEQ ID No: 22-23 of greater than 98%. In another embodiment, "homology" refers to identity to one of SEQ ID No: 22-23 of greater than 99%. In another embodiment, "homology" refers to identity to one of SEQ ID No: 22-23 of 100%. Each possibility represents a separate embodiment of the present invention.

Protein and/or peptide homology for any AA sequence listed herein is determined, in one embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and employ, in other embodiments, the use of the Smith and Waterman algorithms, and/or global/local or BLOCKS alignments for analysis, for example. Each method of determining homology represents a separate embodiment of the present invention.

In another embodiment, the LLO protein is attached to the E7 or E6 antigen by chemical conjugation. In another embodiment, glutaraldehyde is used for the conjugation. In another embodiment, the conjugation is performed using any suitable method known in the art. Each possibility represents another embodiment of the present invention.

In another embodiment, the present invention provides a kit comprising vaccine of the present invention, an applicator, and instructional material that describes use of the methods of the invention. Although model kits are described below, the contents of other useful kits will be apparent to the skilled artisan in light of the present disclosure. Each of these kits represents a separate embodiment of the present invention.

EXPERIMENTAL DETAILS SECTION

Example 1

LLO-Antigen Fusions Induce Anti-Tumor Immunity

Materials and Experimental Methods (Examples 1-2)

Cell Lines

The C57BL/6 syngeneic TC-1 tumor was immortalized with HPV-16 E6 and E7 and transformed with the c-Ha-ras oncogene. TC-1, provided by T. C. Wu (Johns Hopkins University School of Medicine, Baltimore, Md.) is a highly tumorigenic lung epithelial cell expressing low levels of with HPV-16 E6 and E7 and transformed with the c-Ha-ras oncogene. TC-1 was grown in RPMI 1640, 10% FCS, 2 mM L-glutamine, 100 U/ml penicillin, 100 µg/ml streptomycin, 100 µM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

L. monocytogenes Strains and Propagation

Listeria strains used were Lm-LLO-E7 (hly-E7 fusion gene in an episomal expression system; FIG. 1A), Lm-E7 (single-copy E7 gene cassette integrated into Listeria genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GG<u>CTCGAG</u>CATGGAGATACACC-3' (SEQ ID No: 8; XhoI site is underlined) and 5'-GGGG<u>ACTAGT</u>TTATGGTTTCTGAGAACA-3' (SEQ ID No: 9; SpeI site is underlined) and ligated into pCR2.1 (Invitrogen, San Diego, Calif.). E7 was excised from pCR2.1 by XhoI/SpeI digestion and ligated into pGG-55. The hly-E7 fusion gene and the pluripotential transcription factor prfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO," and having the sequence set forth in SEQ ID No: 15), which is joined by the XhoI site to the E7 gene, yielding a hly-E7 fusion gene that is transcribed and secreted as LLO-E7. Transformation of a prfA negative strain of Listeria, XFL-7 (provided by Dr. Hao Shen, University of Pennsylvania), with pGG-55 selected for the retention of the plasmid in vivo (FIGS. 1A-B). The hly promoter and gene fragment were generated using primers 5'-GGGG<u>GCTAGC</u>CCTCCTTTGATTAGTATATTC-3' (SEQ ID No: 10; NheI site is underlined) and 5'-CTCC<u>CTCGAG</u>ATCATAATTTACTTCATC-3' (SEQ ID No: 11; XhoI site is underlined). The prfA gene was PCR amplified using primers 5'-GACTACAAGGACGATGACCGA-CAAGTGATAA<u>CCCGGG</u>ATCTAAATAAATCCGTT T-3' (SEQ ID No: 12; XbaI site is underlined) and 5'-CCC<u>GTCGAC</u>CAGCTCTTCTTGGTGAAG-3' (SEQ ID No: 13; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GC<u>GGATCCC</u>ATGGAGATACACCTAC-3' (SEQ ID No: 18; BamHI site is underlined) and 5'-GC<u>TCTAGA</u>TTATGGTTTCTGAG-3' (SEQ ID No: 19; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 µg/ml). Bacteria were frozen in aliquots at −80° C. Expression was verified by Western blotting (FIG. 2).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm Tumor measurements for each time point are shown only for surviving mice.

Effects of Listeria Recombinants on Established Tumor Growth

Six- to 8-wk-old C57BL/6 mice (Charles River) received $2\times10^5$ TC-1 cells s.c. on the left flank. One week following tumor inoculation, the tumors had reached a palpable size of 4-5 mm in diameter. Groups of eight mice were then treated with 0.1 $LD_{50}$ i.p. Lm-LLO-E7 ($10^7$ CFU), Lm-E7 ($10^6$ CFU), Lm-LLO-NP ($10^7$ CFU), or Lm-Gag ($5\times10^5$ CFU) on days 7 and 14.

$^{51}$Cr Release Assay

C57BL/6 mice, 6-8 wk old, were immunized i.p. with 0.1 $LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7 H-2b peptide (RAHYNIVTF). E:T cell ratios, performed in triplicate, were 80:1, 40:1, 20:1, 10:1, 5:1, and 2.5:1. Following a 4-h incubation at 37° C., cells were pelleted, and 50 µl supernatant was removed from each well. Samples were assayed with a Wallac 1450 scintillation counter (Gaithersburg, Md.). The percent specific lysis was determined as [(experimental counts per minute (cpm)-spontaneous cpm)/(total cpm−spontaneous cpm)]×100.

TC-1-Specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5\times10^5$/well in flat-bottom 96-well plates with $2.5\times10^4$, $1.25\times10^4$, $6\times10^3$, or $3\times10^3$ irradiated TC-1 cells/well as a source of E7 Ag, or without TC-1 cells or with 10 µg/ml Con A. Cells were pulsed 45 h later with 0.5 µCi [$^3$H]thymidine/well. Plates were harvested 18 h later using a Tomtec harvester 96 (Orange, Conn.), and proliferation was assessed with a Wallac 1450 scintillation counter. The change in cpm was calculated as experimental cpm—no Ag cpm.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7 H-2 Db tetramer was performed using a FACSCalibur® flow cytometer with CellQuest® software (Becton Dickinson, Mountain View, Calif.). Splenocytes harvested 5 days after the boost were stained at room temperature (rt) with H-2 Db tetramers loaded with the E7 peptide (RAHYNIVTF) or a control (HIV-Gag) peptide. Tetramers were used at a 1/200 dilution and were provided by Dr. Larry R. Pease (Mayo Clinic, Rochester, Minn.) and by the NIAID Tetramer Core Facility and the NIH AIDS Research and Reference Reagent Program. Tetramer$^+$, CD8$^+$, CD62L$^{low}$ cells were analyzed.

B16F0-Ova Experiment

24 C57BL/6 mice were inoculated with 5×10$^5$ B 16F0-Ova cells. On days 3, 10 and 17, groups of 8 mice were immunized with 0.1 LD$_{50}$ Lm-OVA (10$^6$ cfu), Lm-LLO-OVA (10$^8$ cfu) and eight animals were left untreated.

Statistics

For comparisons of tumor diameters, mean and SD of tumor size for each group were determined, and statistical significance was determined by Student's t test. p≤0.05 was considered significant.

Results

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 LD$_{50}$ Lm-E7, Lm-LLO-E7, or, as controls, Lm-Gag and Lm-LLO-NP. Lm-LLO-E7 induced complete regression of 75% of established TC-1 tumors, while tumor growth was controlled in the other 2 mice in the group (FIG. 3). By contrast, immunization with Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively Animals immunized with Lm-LLO-E7 remained tumor free until termination of the experiment (day 124 in the case of TC-1 and day 54 for EL-4/E7).

Thus, expression of an antigen as a fusion protein with ΔLLO enhances the immunogenicity of the antigen.

Example 2

LM-LLO-E7 Treatment Elicits TC-1 Specific Splenocyte Proliferation

Figure 4:
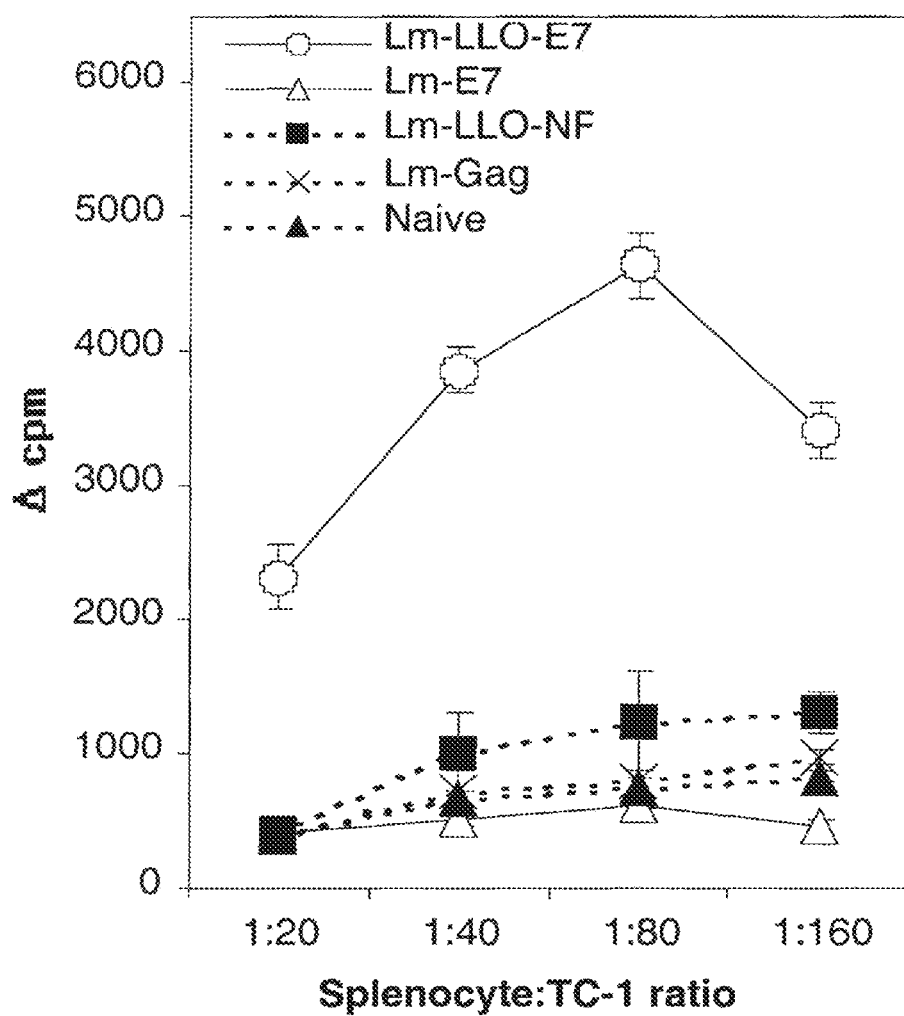
FIG. 4. Splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)−(no-TC-1 control).

To measure induction of T cells by Lm-E7 with Lm-LLO-E7, TC-1-specific proliferative responses, a measure of antigen-specific immunocompetence, were measured in immunized mice. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control-immunized mice exhibited only background levels of proliferation.

Example 3

Fusion of E7 to LLO Enhances E7-Specific Immunity and Generates Tumor-Infiltrating E7-Specific CD8$^+$ Cells Materials and Experimental Methods 500 mcl (microliter) of MATRIGEL®, comprising 100 mcl of 2×10$^5$ TC-1 tumor cells in phosphate buffered saline (PBS) plus 400 mcl of MATRIGEL® (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGELs were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of NaN$_3$ in PBS for tetramer and IFN-gamma staining.

Splenocytes and tumor cells were incubated with 1 micromole (mcm) E7 peptide for 5 hours in the presence of brefeldin A at 10$^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit Golgi-stop® or Golgi-Plug® (Pharmingen, San Diego, Calif.), and stained for IFN-gamma. 500,000 events were acquired using two-laser flow cytometer FACSCalibur and analyzed using Cellquest Software (Becton Dickinson, Franklin Lakes, N.J.). Percentages of IFN-gamma secreting cells within the activated (CD62L$^{low}$) CD8$^+$ T cells were calculated.

For tetramer staining, H-2D$^b$ tetramer was loaded with phycoerythrin (PE)-conjugated E7 peptide (RAHYNIVTF, SEQ ID NO: 14), stained at rt for 1 hour, and stained with anti-allophycocyanin (APC) conjugated MEL-14 (CD62L) and FITC-conjugated CD813 at 4° C. for 30 min Cells were analyzed comparing tetramer$^+$ CD8$^+$ CD62L$^{low}$ cells in the spleen and in the tumor.

Results

Figure 5A:
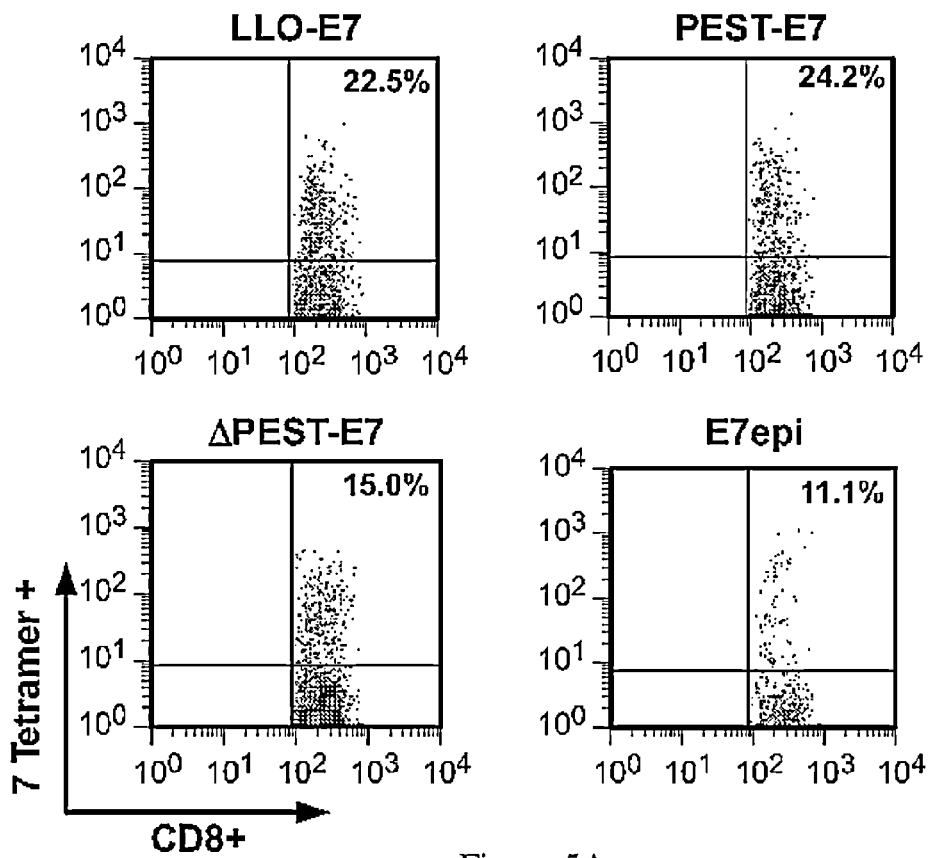
FIGS. 5A-5B. *Listeria* constructs containing PEST regions induce a higher percentage of E7-specific lymphocytes within the tumor.
Figure 5B:
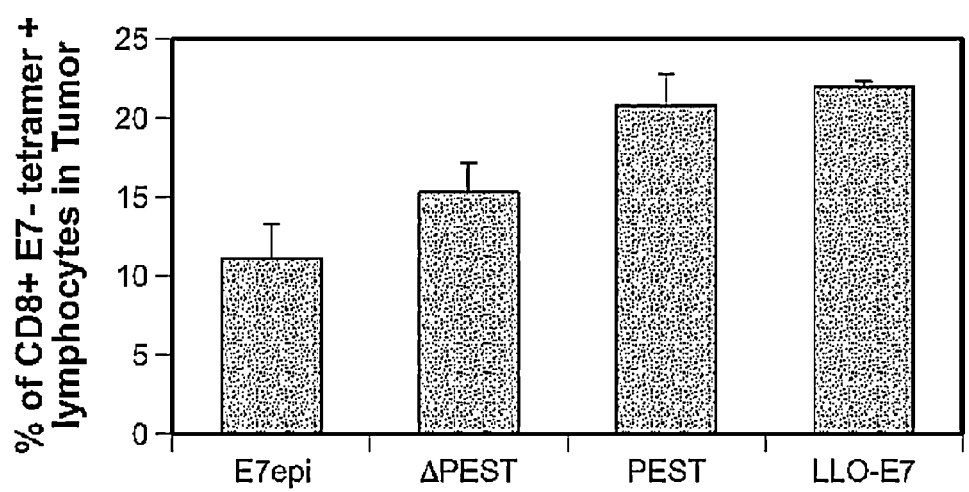

In another experiment, tumor-bearing mice were administered Lm-LLO-E7, or Lm-E7epi, and levels of E7-specific lymphocytes within the tumor were measured. Mice were treated on days 7 and 14 with 0.1 LD$_{50}$ of the 4 vaccines. Tumors were harvested on day 21 and stained with antibodies to CD62L, CD8, and with the E7/Db tetramer. An increased percentage of tetramer-positive lymphocytes within the tumor were seen in mice vaccinated with Lm-LLO-E7 and Lm-PEST-E7 (FIG. 5A). This result was reproducible over three experiments (FIG. 8B).

Thus, Lm-LLO-E7, are each efficacious at induction of tumor-infiltrating CD8$^+$ T cells and tumor regression.

Example 4

E6/E7 Transgenic Mouse Phenotype: A Model for Spontaneous Tumor Growth and Tolerance to a Tumor Antigen Materials and Experimental Methods Several C57BL/6 mouse zygotes were injected with plasmids containing the HPV-16 E6/E7 gene under the control of the thyroglobulin promoter (provided by M Parmentier, Brussels). Tail clippings of several litters were screened via PCR for the E6/E7 gene. The E7 gene and the thyroglobulin promoter were integrated into the majority of the progeny. Positive mosaic E7 transgenic mice were then selected for F0× wild type breeding. Subsequent F1 generations were screened, via PCR, for the presence of the E7 gene. E7 positive pups generated from F0× wt breeding pairs were selected for F1×F1 breeding. The zygosity of F1 breeding pair derived generations was determined by Taqman real-time PCR and the ΔΔCt method (Charles River, 2001). Homozygous E7 transgenic mice were selected for F2×F2 breeding. The subsequent F3 generation was screened via Taqman real-time PCR and backcrossing to confirm fidelity of homozygosity. The levels of gene copy number and transgene expression of the E7 gene was assessed for every homozygous line using Taqman real-time PCR. After 6 back-crossings, these lines were used as the parents of the colony. Transgene expression was further confirmed by appearance of thyroid hyperplasia, as described in the Results section.

Results

Figure 6:
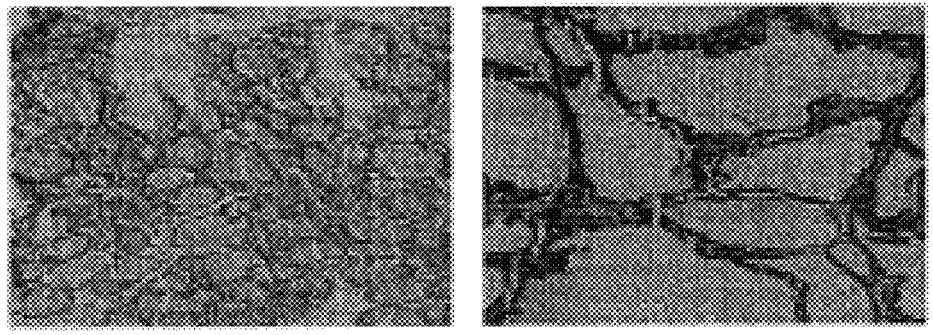
FIG. 6. E6/E7 transgenic mice develop tumors in their thyroid, where the E7 gene is expressed. Mice were sacrificed at 3 months and had their thyroids removed, sectioned, and stained by hematoxylin and eosin. A. Left panel: normal thyroid at 20× magnification. Follicles are of normal size and lined with cuboidal cells with abundant pink cytoplasm (arrow). Right panel: E6/E7 transgenic mouse thyroid. Note the greatly enlarged follicles because of the increased production of colloid. The cuboidal cells lining the follicles are smaller with very little cytoplasm.

E6/E7 transgenic mice were generated, and their phenotype assessed. The mice began to develop thyroid hyperplasia at 8 weeks and palpable goiters at 6 months. By 6 to 8 months, most mice exhibited thyroid cancer. Transgenic mice sacrificed at 3 months of age exhibited de-differentiation of the normal thyroid architecture, indicative of an early stage of cancer. The enlarged, de-differentiated cells were filled with colloid, where thyroid hormones accumulate (FIG. 6).

Example 5

E7 is Expressed In Medullary Thymic Epithelial Cells of E6/E7 Transgenic Mice

Figure 7A:
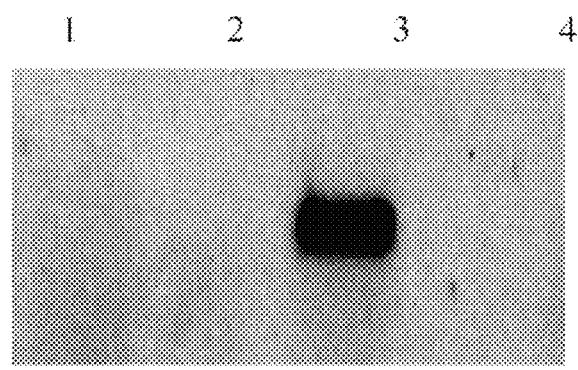
FIGS. 7A-7B. E7 message is expressed in the thyroid and medullary thymic epithelial cells of the E6/E7 transgenic mouse.

To determine whether or not E7 was expressed in the thymus, liver, spleen, thymus and thyroid were examined for the expression of the transgene in 6 to 8 week old mice. Abundant E7 message was found in the thyroid but not in other tissues (FIG. 7A). The absence of E7 message in whole thymus preparations was not indicative of lack of expression in the thymus, since the level of message of a peripherally expressed, organ-specific antigen, including thyroglobulin, has been shown to be too low to detect in whole thymocyte preparations (Derbinski, J., A. Schulte, B. Kyewski, and L. Klein. 2001. Promiscuous gene expression in medullary thymic epithelial cells mirrors the peripheral self. Nat Immunol 2:1032).

Tolerance to peripheral antigens in the thymus, including thyroglobulin, is mediated by the transient expression of these genes by the autoimmune regulator (AIRE) in thymic medullary epithelial cells (mTECs), with peak expression occurring prior to birth. AIRE is a transcription factor that maintains tolerance to self. To determine whether E7 expression in the transgenic mice followed the same pattern, mTECs from E6/E7 thymi of young mice (3-5 weeks) were examined for E7 expression.

Figure 7B:
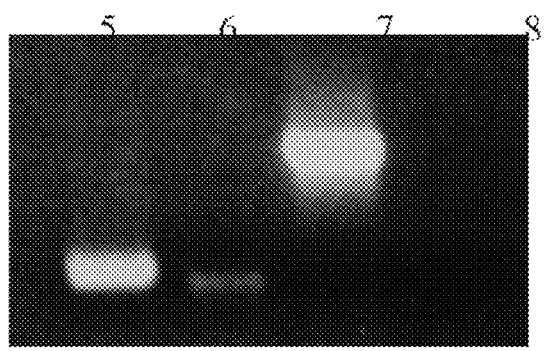

The mTECs expressed E7 message, and also expressed Cathepsin S, which is known to be expressed in mTECs (FIG. 7B). Thus, E7 is expressed in the thymus of the transgenic mice, showing that these mice exhibit tolerance to the E7 antigen.

Example 6

Figure 8:
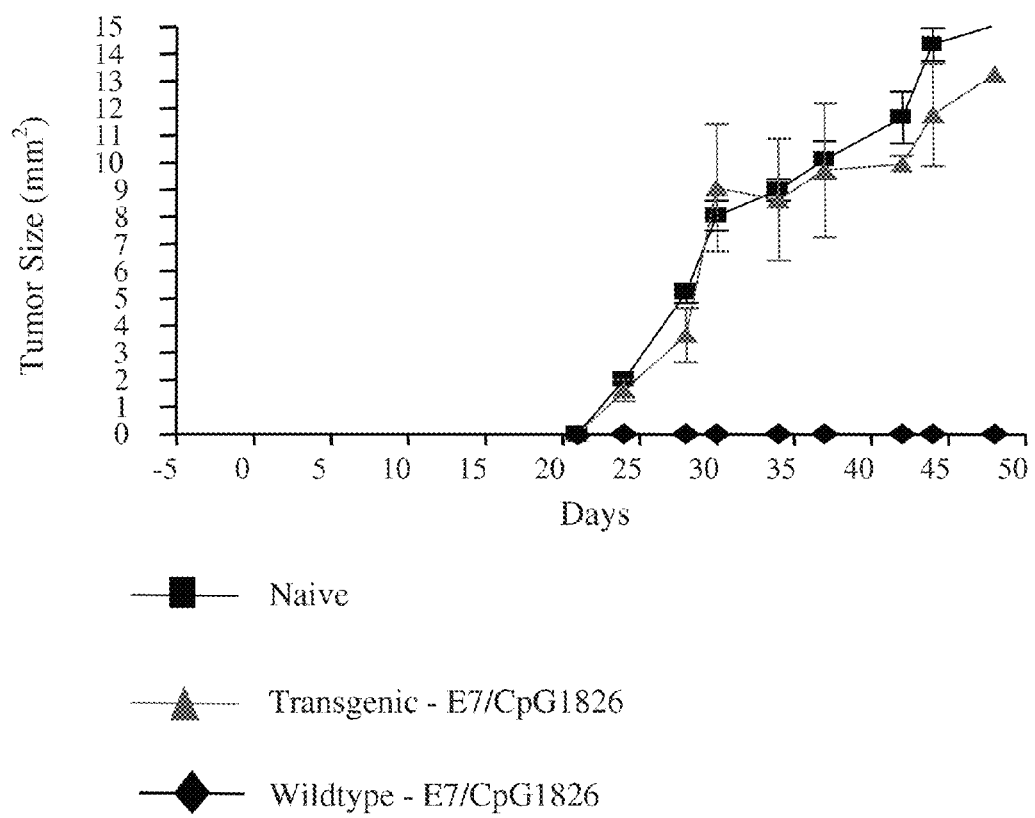
FIG. 8. RAHYNIVTF peptide plus CpG adjuvant does not protect against TC-1 challenge in E6/E7 transgenic mice. Two groups of transgenic mice received either E7 peptide plus adjuvant or PBS. A third group of wild type C57B1/6 control mice received E7 peptide plus adjuvant. The mice were vaccinated twice intraperitoneally (i.p.), 7 days apart and challenged with $5 \times 10^4$ TC-1 cells 7 days later. Tumors were measured every 5 days until unimmunized mice needed to be sacrificed. Error bars: standard deviations from the mean value.

Peptide-Based Vaccines do not Protect Against Tumor Challenge in E6/E7 Transgenic Mice As a measure of the impact of the self-expression of E7 on vaccine efficacy, E6/E7 transgenic mice were tested in a tumor protection experiment using an E7 peptide (RAHYNIVTF)-based vaccine, along with the immunostimulatory CpG sequence 1826 (Krieg A M, Yi A K, Matson S, Waldschmidt T J, Bishop G A, Teasdale R, Koretzky G A, Klinman D M. Nature 374:546). While the peptide-based vaccine protected all the wild type mice from tumor challenge, it had no impact on tumor challenge in the transgenic mouse (FIG. 8). Thus, the E6/E7 mice exhibit reduced ability to reject tumor challenge, providing further evidence that they are tolerant to E7.

Example 7

Figure 9A:
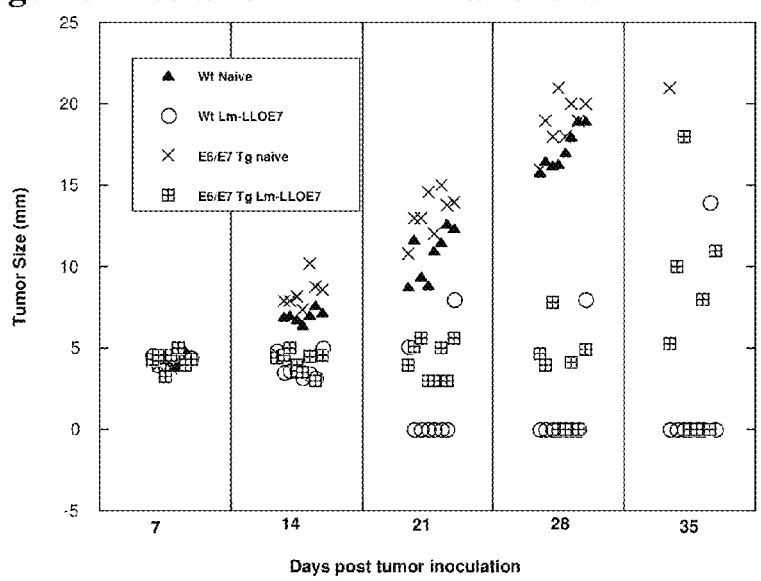
FIGS. 9A-9B. Vaccines of the present invention induce regression of solid tumors in the E6/E7 transgenic mice in wild-type mice and transgenic mice immunized with LM-LLO-E7 (FIG. 9A), or LM-ActA-E7 (FIG. 9B), left naïve, or treated with LM-NP (control).
Figure 9B:
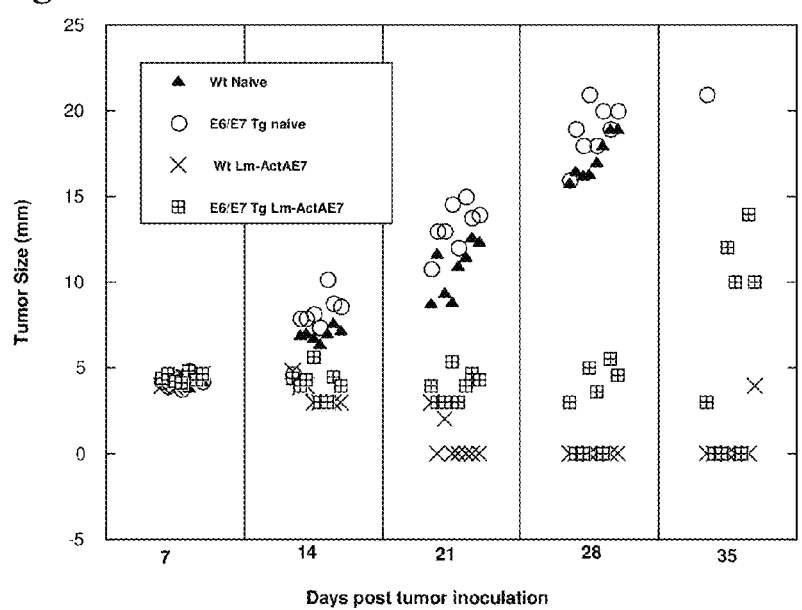

LLO Fusions Overcome Immune Tolerance of E6/E7 Transgenic Mice to E7-Expressing Tumors To test the ability of vaccines of the present invention to overcome the immune tolerance of E6/E7 transgenic mice to E7-expressing tumors, $10^5$ TC-1 cells were implanted subcutaneously (s.c.) and allowed to form solid tumors in 6-8 week old wild-type and transgenic mice 7 and 14 days later, mice were left unimmunized or were immunized i.p. with LM-NP (control), $1 \times 10^8$ cfu LM-LLO-E7 (FIG. 9A) or $2.5 \times 10^8$ cfu LM-ActA-E7 (FIG. 9B). The naïve mice had a large tumor burden, as anticipated, and were sacrificed by day 28 or 35 due to tumors of over 2 cm. By contrast, by day 35, administration of either LM-LLO-E7 resulted in complete tumor regression in 7/8 or 6/8, respectively, of the wild-type mice and 3/8 of the transgenic mice. In the transgenic mice that did not exhibit complete tumor regression, a marked slowing of tumor growth was observed in the LM-LLO-E7-vaccinated mice.

The effectiveness of vaccines of the present invention in inducing complete tumor regression and/or slowing of tumor growth in transgenic mice was in marked contrast to the inefficacy of the peptide-based vaccine. Thus, vaccines of the present invention were able to overcome immune tolerance of E6/E7 transgenic mice to E7-expressing tumors.

Example 8

LLO Fusions Reduce Autochthonous (Spontaneous) Tumors in E6/E7 Transgenic Mice

To determine the impact of the Lm-LLO-E7 vaccines on autochthonous tumors in the E6/E7 transgenic mouse, 6 to 8 week old mice were immunized with $1 \times 10^8$ Lm-LLO-E7 once per month for 8 months. Mice were sacrificed 20 days after the last immunization and their thyroids removed and weighed. This experiment was performed twice (Table 1).

TABLE 1

Thyroid weight (mg) in unvaccinated and vaccinated transgenic mice at 8 months of age (mg)*.

| Untreated | ±S.D. | Lm-LLO-NP | ±S.D. | Lm-LLO-E7 | ±S.D. |
|---|---|---|---|---|---|
| Expt. 1 408 | 123 | 385 | 130 | 225 | 54 |
| Expt. 2 588 | 94 | 503 | 86 | 239 | 68 |

*Statistical analyses performed using Student's t test showed that the difference in thyroid weight between Lm-LLO-NP treated mice and untreated mice was not significant but that the difference between Lm-LLO-E7 treated mice was highly significant (p < 0.001)

The difference in thyroid weight between Lm-LLO-E7 treated mice and untreated mice was significant (p<0.001 and p<0.05, respectively) for both experiments, while the difference between Lm-LLO-NP treated mice (irrelevant antigen control) and untreated mice was not significant (Student's t test), showing that Lm-LLO-E7 controlled spontaneous tumor growth. Thus, vaccines of the present invention prevent formation of new E7-expressing tumors.

To summarize the findings in the above Examples, LLO-antigen fusions (a) induce tumor-specific immune response that include tumor-infiltrating antigen-specific T cells; and are capable of inducing tumor regression and controlling tumor growth of both normal and particularly aggressive tumors; (b) overcome tolerance to self antigens; and (c) prevent spontaneous tumor growth. These findings are generalizable to a large number of antigens, PEST-like sequences, and tumor types, as evidenced by their successful implementation with a variety of different antigens, PEST-like sequences, and tumor types.

Example 9

LM-LLO-E7 Vaccines are Safe and Improve Clinical Indicators in Cervical Cancer Patients Materials and Experimental Methods Inclusion criteria. All patients in the trial were diagnosed with "advanced, progressive or recurrent cervical cancer," and an assessment at the time of entry indicated that all were staged as having IVB disease. All patients manifested a positive immune response to an anergy panel containing 3 memory antigens selected from candidin, mumps, tetanus, or Tuberculin Purified Protein Derivative (PPD); were not pregnant or HIV positive, had taken no investigational drugs within 4 weeks, and were not receiving steroids.

Protocol: Patients were administered 2 vaccinations at a 3-week interval as a 30-minute intravenous (IV) infusion in 250 ml of normal saline to inpatients. After 5 days, patients received a single course of IV ampicillin and were released with an additional 10 days of oral ampicillin Karnofsky Performance Index, which is a measurement of overall vitality and quality of life such as appetite, ability to complete daily tasks, restful sleep, etc, was used to determine overall well-being. In addition, the following indicators of safety and general well being were determined: alkaline phosphatase; bilirubin, both direct and total; gamma glutamyl transpeptidase (ggt); cholesterol; systole, diastole, and heart rate; Eastern Collaborative Oncology Group's (ECOG)'s criteria for assessing disease progression—a Karnofsky like—quality of life indicator; hematocrit; hemoglobin; platelet levels; lymphocytes levels; AST (aspartate aminotransferase); ALT (alanine aminotransferase); and LDH (lactate dehydrogenase). Patients were followed at 3 weeks and 3 months subsequent to the second dosing, at which time Response Evaluation Criteria in Solid Tumors (RECIST) scores of the patients were determined, scans were performed to determine tumor size, and blood samples were collected for immunological analysis at the end of the trial, which includes the evaluation of IFN-γ, IL-4, CD4+ and CD8+ cell populations.

Listeria strains: The creation of LM-LLO-E7 is described in Example 1. Bacteria were passaged twice through mice prior to preparation of the working cell bank, as described in Example 12. The cell bank exhibited viability upon thawing of greater than 90%.

Results

Prior to the clinical trial, a preclinical experiment was performed to determine the anti-tumor efficacy of intravenous (i.v.) vs. i.p. administration of LM-LLO-E7. A tumor containing $1 \times 10^4$ TC-1 cells was established sub-cutaneously. On days 7 and 14, mice were immunized with either $10^8$ LM-LLO-E7 i.p. or LM-LLO-E7 i.v. at doses of $10^8$, $10^7$, $10^6$, or $10^5$. At day 35, 5/8 of the mice that received $10^8$ LM-LLO-E7 by either route or $10^7$ LM-LLO-E7 i.v, and 4/8 of the mice that received $10^6$ LM-LLO-E7 i.v, were cured. By contrast, doses of less than $10^7$ or in some cases even $10^8$ LM-LLO-E7 administered i.p. were ineffective at controlling tumor growth. Thus, i.v. administration of LM-LLO-E7 is more effective than i.p. administration.

Clinical Trial

A phase I/II clinical trial was conducted to assess safety and efficacy of LM-LLO-E7 vaccines in patients with advanced, progressive, or recurrent cervical cancer. 5 patients each were assigned to cohorts 1-2, which received $1 \times 10^9$ or $3.3 \times 10^9$ CFU, respectfully. An additional 5 patients each will be assigned to cohorts 3-4, which will receive $1 \times 10^{10}$ or $3.31 \times 10^{10}$ CFU, respectfully.

Safety data

First Cohort

All patients in the first cohort reported onset of mild-to-moderate fever and chills within 1-2 hours after onset of the infusion. Some patients exhibited vomiting, with or without nausea. With 1 exception (described below), a single dose of a non-steroidal agent such as paracetamol was sufficient to resolve these symptoms. Modest, transient cardiovascular effects were observed, consistent with, and sharing the time course of, the fever. No other adverse effects were reported.

At this late stage of cervical cancer, 1 year survival is typically 10-15% of patients and no tumor therapy has ever been effective. Indeed, Patient 2 was a young patient with very aggressive disease who passed away shortly after completing the trial.

Quantitative blood cultures were assessed on days 2, 3, and 5 post-administration. Of the 5 evaluable patients in this cohort, 4 exhibited no serum Listeria at any time and 1 had a very small amount (35 cfu) of circulating Listeria on day 2, with no detectable Listeria on day 3 or 5.

Patient 5 responded to initial vaccination with mild fever over the 48 hours subsequent to administration, and was treated with anti-inflammatory agents. On 1 occasion, the fever rose to moderate severity (at no time above 38.4° C.), after which she was given a course of ampicillin, which resolved the fever. During the antibiotic administration she experienced mild urticaria, which ended after antibiotic administration. Blood cultures were all sterile, cardiovascular data were within the range observed for other patients, and serum chemistry values were normal, showing that this patient had no listerial disease. Further, the anergy panel indicated a robust response to 1/3 memory antigens, indicating the presence of functional immunity (similar to the other patients). Patient 5 subsequently evidenced a response similar to all other patients upon receiving the boost.

Second Cohort and Overall Safety Observations

In both cohorts, minor and transient changes in liver function tests were observed following infusion. These changes were determined by the attending physician monitoring the trial to have no clinical significance, and were expected for a short-lived infection of bacteria that are rapidly removed from the systemic circulation to the liver and spleen. In general, all the safety indicators described in the Methods section above displayed little or no net change, indicative of an excellent safety profile. The side effect profile in this cohort was virtually identical to that seen in the in the initial cohort and appeared to be a dose independent series of symptoms related to the consequences of cytokines and similar agents that occur consequent to the induction of an iatrogenic infection. No serum *Listeria* was observed at any time and no dose limiting toxicity was observed in either cohort.

Efficacy—First Cohort

The following indications of efficacy were observed in the 3 patients in the first cohort that finished the trial: (Table 2).

Patient 1 entered the trial with 2 tumors of 20 mm each, which shrunk to 18 and 14 mm over the course of the trial, indicating therapeutic efficacy of the vaccine. In addition, patient 1 entered the trial with a Karnofsky Performance Index of 70, which rose to 90 after dosing. In the Safety Review Panel meeting, Siniša Radulovic, the chairman of the Department of Oncology, Institute for Oncology and Radiology, Belgrade, Serbia presented the results to a representative of the entity conducting the trials; Michael Kurman, an independent oncologist who works as a consultant for the entity; Kevin Ault, an academic gynecologic oncologist at Emory University who conducted the phase III Gardasil trials for Merck and the Cervarix trials for Glaxo SmithKline; and Tate Thigpen, a founder of the Gynecologic Oncology Group at NCI and professor of gynecologic oncology at the University of Mississippi. In the opinion of Dr. Radulovic, patient 1 exhibited a clinical benefit from treatment with the vaccine.

Before passing away, Patient 2 exhibited a mixed response, with ½ tumors shrinking.

Patient 3 enrolled with paraneoplastic disease, (an epiphenomenon of cancer wherein the overall debilitated state of the patient has other sequelae that are secondary to the cancer), including an elevation of platelet count to $936\times10^9$/ml. The count decreased to $465\times10^9$/ml, approximately a normal level, following the first dose.

Patient 4 entered the trial with 2 tumors of 20 mm each, which shrunk to 18 and 14 mm over the course of the trial, indicating therapeutic efficacy of the vaccine. Patient 4 exhibited a weight gain of 1.6 Kg and an increased hemoglobin count of approximately 10% between the first and second doses.

Efficacy—Second Cohort and General Observations

In the lowest dose cohort, 2 patients demonstrated the shrinkage of tumors. The timing of this effect was consistent with that observed in immunological responses, in that it followed chronologically development of the immune response. One of the 2 patients in the second cohort evaluated so far for tumor burden exhibited a dramatic tumor load reduction at a post-vaccination time point. At the start of the trial, this patient had 3 tumors of 13, 13, and 14 mm. After the 2 doses of the vaccine, 2 of the tumor had shrunk to 9.4 and 12 mm, and the third was no longer detectable.

Figure 10A:
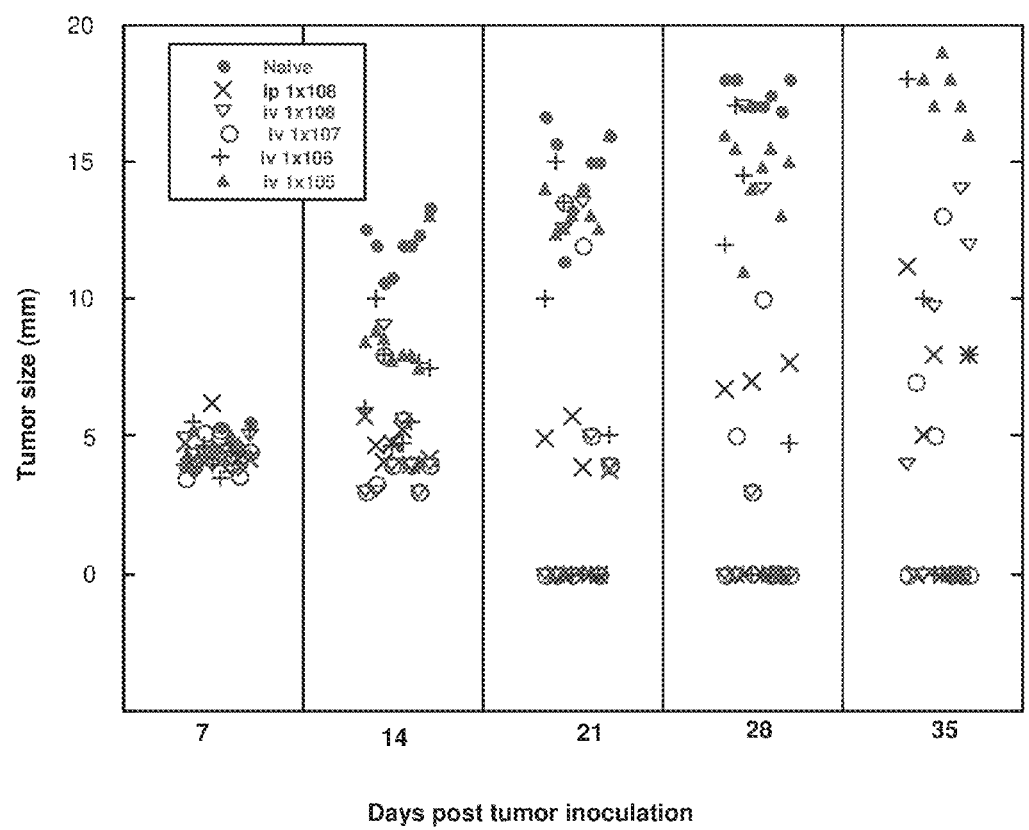
FIGS. 10A-10B.
Figure 10B:
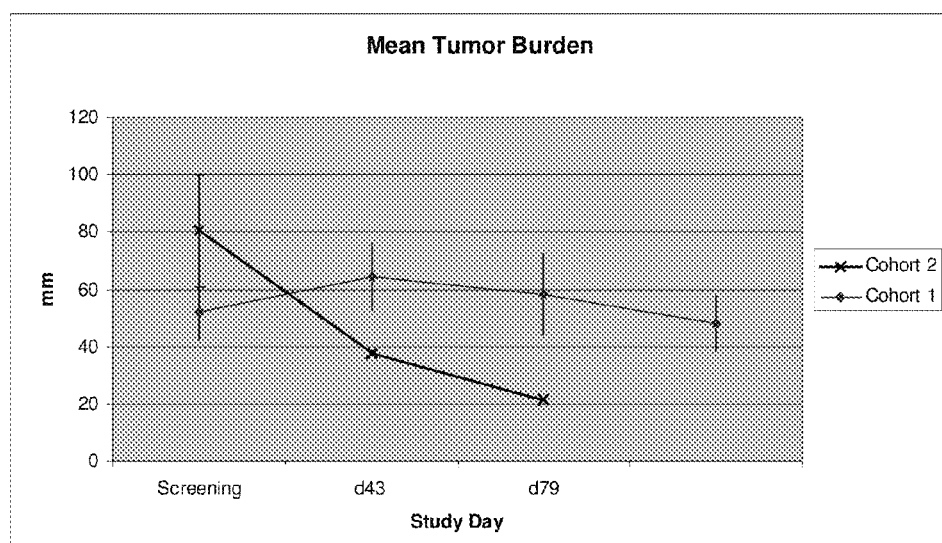

Tumors loads for the 2 cohorts are depicted in FIG. 10B. In summary, even relatively low doses of LM-LLO-E7, administered in a therapeutic regimen containing a priming injection and a single boost, achieved 3 objective responses out of 6 patients for whom data has been collected.

Discussion

At this late stage of cervical cancer, 1 year survival is typically 10-15% of patients and no tumor therapy has ever been effective. No treatment has shown to be effective in reversing stage IVB cervical cancer. Despite the difficulty of treating cervical cancer at this stage, an anti-tumor effect was observed in 2/6 patients. In addition, other indications of efficacy were observed in patients that finished the trial, as described hereinabove.

Thus, LM-LLO-E7 is safe in human subjects and improves clinical indicators of cervical cancer patients, even when administered at relatively low doses. Additional positive results are likely to be observed when the dose and number of booster vaccinations is increased; and/or when antibiotics are administered in smaller doses or at a later time point after infusion. Pre-clinical studies have shown that a dose increase of a single order of magnitude can cause dramatic changes in response rate (e.g. a change from 0% response rate to 50-100% complete remission rate. Additional booster doses are also very likely to further enhance the immune responses obtained. Moreover, the positive effects of the therapeutic immune response observed are likely to continue with the passage of additional time, as the immune system continues to attack the cancer.

Example 10

Safety and Efficacy of LM-LLO-E7 for the Treatment of Cervical Intraepithelial Neoplasia Advaxis has treated 45 patients with grade 2 or 3 Cervical Intraepithelial Neoplasia (cervical dysplasia) thus far in a trial designed to treat 120 patents. Three treatment groups of 40 patients each are comprised of 10 patients who get placebo on a randomized basis and 30 patients who get active drug at $5.10^7$, $3.3\times10^8$ or $1\times10^9$ cfu. A safety run in of 3 patients is conducted for each dosage group and these patients receive the active drug. The remaining 37 patients are randomized to either placebo or active drug at a ratio of 3 active patients for each placebo patient. The trial involves the administration of Advaxis agent ADXS11-001 directed against HPV 16-E7 3 times at 28 day intervals followed by a surgical LEEP procedure 6 months after the initial dose. Pretreatment biopsy samples are compared with post treatment LEEP surgery specimens for an assessment of histologic response.

The objective of this study was to see whether a vaccine regimen can replace surgery. Aside from the pain, bleeding, and other aspects of surgery, the removal of a portion of the cervix often leads to an inability to come to a full term pregnancy ("incompetent cervix"). A pharmaceutical treatment would thus be preferential to surgery. Especially one that induces immunologic memory against the etiologic agent that causes cervix cancer, HPV, in a manner that protects against recurrence.

At the present time the random code has not been broken, however of the 18 treated patients 3-4 patients have receive placebo and 14-15 patients have received active drug. The average spontaneous remission rate in this population is approximately 25%, and 4-5 patients spontaneously remit assuming the experimental agent was ineffective, but in the 18 patients treated to date, irrespective of treatment, 14 have remitted. Thus, a therapeutic effect of the agent on the precancerous condition of CIN is being observed.

Example 11

Safety and Efficacy of LM-LLO-E7 for the Treatment of Cervical Intraepithelial Neoplasia Stages II and III Materials and Experimental Methods Inclusion Criteria Age 18 or older and capable of providing informed consent according to federal, state and institutional guidelines.

Patients must have either Stage II or Stage III Cervical Intraepithelial Neoplasia for which surgical intervention is indicated, and for whom the disease is sufficiently indolent to allow for a 6-month treatment and observation period to occur prior to surgery.

HPV-16 E7 positive.

Cytological evidence consistent with a diagnosis of CIN II/III.

All patients eligible for this study must be discussed with the principal investigators and be approved by the principal investigators before study entry.

Patients must respond positively to at least 1 of the test agents used in the anergy panel described for the previous Example. A positive reaction defined by the formation of a local tissue response of at least 5 mm in sum of the orthogonal measures in reaction to the administration of a delayed hypersensitivity stimulus is required.

Exclusion Criteria

Patients who have had chemotherapy, radiotherapy, or steroids within 4 weeks prior to the initial study dose or those who have not recovered from adverse events due to agents administered more than 4 weeks earlier.

Patients who have received any other investigational agents for 28 days prior to dosing.

A history of Listeriosis.

A history of prior cancer or concomitant cancer.

Patients who are immunocompromised as demonstrated by a negative result from an anergy panel screening.

Uncontrolled intercurrent illness including, but not limited to ongoing or active infection, symptomatic congestive heart failure, unstable angina pectoris, cardiac arrhythmia, or psychiatric illness/social situations that would limit compliance with study requirements.

Hepatitis, cirrhosis, or any other impaired hepatic function as determined by serum enzymes.

Pregnant women and women actively trying to become pregnant.

Known HIV-positive patients.

Penicillin allergy.

Primary Safety Endpoints:
 Incidence and severity of observations of the administration site including swelling, irritation, immune reaction or other abnormalities.
 Incidence and severity of adverse events assessed throughout the duration of the study.
 Changes in clinical hematology and serum chemistry test results at each time point from dosing through week 16.
 Rate of clearance of LM-LLO-E7 from the blood, as determined by quantitative blood cultures during the inpatient portion of the study following the initial administration.

Primary Efficacy Endpoints:
 Regression of CIN to normal upon colposcopic examination
 Regression of CIN toward normal sufficient to cancel or delay surgery
 Improved cytology subsequent to surgery Primary Immunogenicity Endpoints:
 HLA typing of patients for Class I and II,
 Quantification of a serum cytokine profile subsequent to dosing that corresponds with observed side effects,
 Quantification of macrophage activation parameters that assess macrophage activation subsequent to dosing,
 Identification of tumor-associated antigen (TAA)-specific activated T cells and quantification of T cell responses subsequent to dosing,
 Quantification of T cell subsets migrating to TAA DTH.

Immunogenicity Criteria:

Serum Cytokines

IFN-γ, TNF-α, IL-2 & IL-12 are assessed in serum of patients, collected at the following times:
 Screening, Day 1.
 Day 1, pre-dose, Day 1, 3 h post-dose, Day 1, 12 h post-dose, Day 2, 24 h post-dose, and Day 5.
 Day 22 pre-dose, Day 22, 3 h post-dose, Day 22, 12 h post-dose, Day 23, 24 h post-dose, and Day 26
 Day 43 pre-dose, Day 43, 3 h post-dose, Day 43, 12 h post-dose, Day 44, 24 h post-dose, and Day 47

T Cell Responses

The following cytokine release profiles are assessed HPV-16 E7 stimulated T cells of patients: IFN-γ, TNF-α, IL-2 & IL-4

Assays are performed on cells sampled from patients at the following times: Screening, Day 1 pre-dosing, day 22 pre-dosing, day 43 pre-dosing, day 126, and day 180

Delayed Type Hypersensitivity Testing

DTH testing is conducted on the following study days: Screening, Day 5, Day 26, Day 47, Day 126 and Day 180.

Macrophage Activation

Samples for the assessment of macrophage activation are collected on the following study days and times:
 Day 1 pre-dose, Day 1, 3 h post-dose, Day 1, 12 h post-dose, Day 2, 24 h post-dose, and Day 5.
 Day 22 pre-dose, Day 22, 3 h post-dose, Day 22, 12 h post-dose, Day 23, 24 h post-dose, and Day 26.
 Day 43 pre-dose, Day 43, 3 h post-dose, Day 43, 12 h post-dose, Day 44, 24 h post-dose, and Day 47.

Vaccine Administration

LM-LLO-E7 is administered as a 30 min. i.v. infusion with each dose freshly thawed and diluted in 250 ml normal saline.

Safety Review

Adverse Events are graded based on the National Cancer Institute (NCI) Common Toxicity Criteria. Dose limiting toxicity is defined as any of the following:

Non-Hematologic Toxicity:
1. Presumptive bacterial meningitis as determined by symptoms.
2. Persistent listeremia at day 5 and 15 after a 10-day course of antibiotics.
3. Clinical sepsis requiring ICU admission.
4. A drop in blood pressure sufficient to warrant therapeutic intervention,
5. Hepatitis as evidenced by grade 3-4 elevation in transaminases for a minimum of 7 days.
6. Gastrointestinal toxicity of grade 3-4 despite adequate medical intervention.
7. Any Grade 3 injection site reaction.
8. Any Grade 3 or higher adverse event that cannot be attributed to cervical cancer or other concurrent illnesses.

Hematologic Toxicity:
1. Absolute neutrophil count (ANC) grade 4 for a minimum of 7 days or neutropenic fever defined as Grade 4 neutropenia with temperature of ≥38.5° C.
2. Platelet count grade 4 or bleeding with Grade 3 platelet count.

Dose escalation to the next cohort proceeds in each case, provided that there are no Grade 3 or higher adverse events related to the therapeutic vaccine.

Results

Women are enrolled that have stage II or stage III Cervical Intraepithelial Neoplasia (CIN II/III) who have disease that is sufficiently indolent to allow for a 6 month period of treatment and evaluation to occur prior to surgery. Patients receive 3 doses of LM-LLO-E7 at 3 week intervals as inpatients and return for follow up visits to assess their response to the vaccine, collect samples for analysis, and assess their disease. Samples for immunologic analysis are collected throughout the trial and assayed upon the completion of the study.

Safety is assessed through standard physical, hematologic and serum chemistry measures, and by blood cultures to assess serum *Listeria*. Immunologic activity is assessed in the areas of serum cytokine release, activated T cell responses to tumor antigen, macrophage activation, and delayed hypersensitivity responses (DTH) to tumor antigen.

Clinically, patients are grouped by primary endpoints. Namely, whether patients exhibit sufficient remission of their disease to make surgery unnecessary. Patients that do require surgery, are grouped regarding whether they exhibit lesser disease than the control group. LM-LLO-E7 reduces the fraction of women that subsequently require surgery and/or the degree of disease among those that require surgery.

Example 12

Passaging of Listeria vaccine vectors through Mice Elicits Increased Immune Responses to Heterologous and Endogenous Antigens Materials and Experimental Methods Bacterial Strains

*L. monocytogenes* strain 10403S, serotype 1 (ATCC, Manassas, Va.) was the wild type organism used in these studies and the parental strain of the constructs described below. Strain 10403S has an $LD_{50}$ of approximately $5 \times 10^4$ CFU when injected intraperitoneally into BALB/c mice. "Lm-Gag" is a recombinant LM strain containing a copy of the HIV-1 strain HXB (subtype B laboratory strain with a syncytia-forming phenotype) gag gene stably integrated into the listerial chromosome using a modified shuttle vector pKSV7. Gag protein was expressed and secreted by the strain, as determined by Western blot. All strains were grown in brain-heart infusion (BHI) broth or agar plates (Difco Labs, Detroit, Mich.).

Bacterial Culture

Bacteria from a single clone expressing the passenger antigen and/or fusion protein were selected and cultured in BHI broth overnight. Aliquots of this culture were frozen at −70° C. with no additives. From this stock, cultures were grown to 0.1-0.2 O.D. at 600 nm, and aliquots were again frozen at −70° C. with no additives. To prepare cloned bacterial pools, the above procedure was used, but after each passage a number of bacterial clones were selected and checked for expression of the target antigen, as described herein. Clones in which expression of the foreign antigen was confirmed were used for the next passage.

Passage of Bacteria in Mice 6-8 week old female BALB/c (H-2d) mice were purchased from Jackson Laboratories (Bar Harbor, Me.) and were maintained in a pathogen-free microisolator environment. The titer of viable bacteria in an aliquot of stock culture, stored frozen at −70° C., was determined by plating on BHI agar plates on thawing and prior to use. In all, $5 \times 10^5$ bacteria were injected intravenously into BALB/c mice. After 3 days, spleens were harvested, homogenized, and serial dilutions of the spleen homogenate were incubated in BHI broth overnight and plated on BHI agar plates. For further passage, aliquots were again grown to 0.1-0.2 O.D., frozen at −70° C., and bacterial titer was again determined by serial dilution. After the initial passage (passage 0), this sequence was repeated for a total of 4 times.

Intracellular Cytokine Stain for IFN-Gamma

Lymphocytes were cultured for 5 hours in complete RPMI-10 medium supplemented with 50 U/ml human recombinant IL-2 and 1 microliter/ml Brefeldin A (Golgistop™; PharMingen, San Diego, Calif.) in the presence or absence of either the cytotoxic T-cell (CTL) epitope for HIV-GAG (AMQMLKETI; SEQ ID No: 24), *Listeria* LLO (GYKDGNEYI; SEQ ID No: 25) or the HPV virus gene E7 (RAHYNIVTF (SEQ ID No: 14), at a concentration of 1 micromole. Cells were first surface-stained, then washed and subjected to intracellular cytokine stain using the Cytofix/Cytoperm kit in accordance with the manufacturer's recommendations (PharMingen, San Diego, Calif.). For intracellular IFN-gamma stain, FITC-conjugated rat anti-mouse IFN-gamma monoclonal antibody (clone XMG 1.2) and its isotype control Ab (rat IgG1; both from PharMingen) was used. In all, $10^6$ cells were stained in PBS containing 1% Bovine Serum Albumin and 0.02% sodium azide (FACS Buffer) for 30 minutes at 4° C. followed by 3 washes in FACS buffer. Sample data were acquired on either a FACScan™ flowcytometer or FACSCalibur™ instrument (Becton Dickinson, San Jose, Calif.). Three-color flow cytometry for CD8 (PERCP conjugated, rat anti-mouse, clone 53-6.7 Pharmingen, San Diego, Calif.), CD62L (APC conjugated, rat anti-mouse, clone MEL-14), and intracellular IFN-gamma was performed using a FACSCalibur™ flow cytometer, and data were further analyzed with CELLQuest software (Becton Dickinson, Mountain View, Calif.). Cells were gated on CD8 high and $CD62L^{low}$ before they were analyzed for $CD8^+$ and intracellular IFN-gamma staining.

Results

Passaging in Mice Increases the Virulence of Recombinant *Listeria monocytogenes*

Three different constructs were used to determine the impact of passaging on recombinant *Listeria* vaccine vectors. Two of these constructs carry a genomic insertion of the passenger antigen: the first comprises the HIV gag gene (Lm-Gag), and the second comprises the HPV E7 gene (Lm-E7). The third (Lm-LLO-E7) comprises a plasmid with the fusion gene for the passenger antigen (HPV E7) fused with a truncated version of LLO and a gene encoding prfA, the positive regulatory factor that controls *Listeria* virulence factors. This plasmid was used to complement a prfA negative mutant so that in a live host, selection pressures would favor conservation of the plasmid, because without it the bacterium is avirulent. All 3 constructs had been propagated extensively in vitro for many bacterial generations.

Figure 11A:
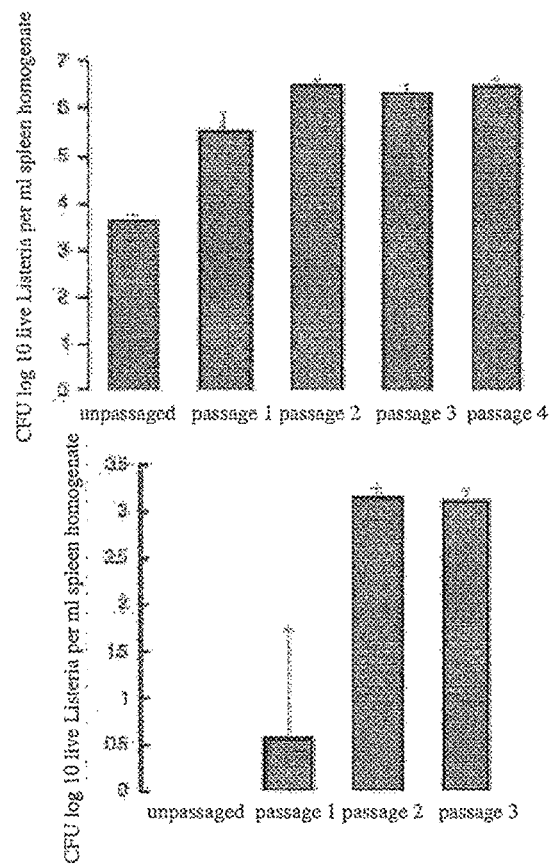
FIGS. 11A-11B.
Figure 11B:
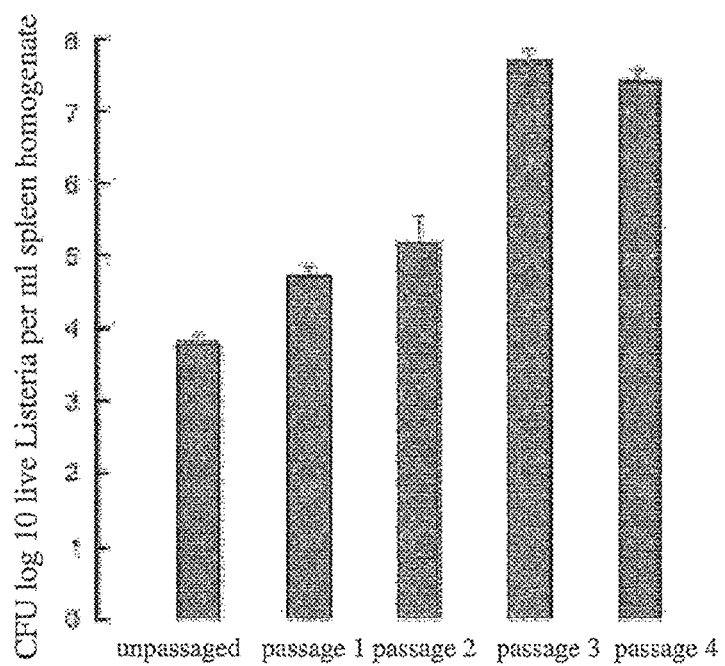

Passaging the bacteria resulted in an increase in bacterial virulence, as measured by numbers of surviving bacteria in the spleen, with each of the first 2 passages. For Lm-Gag and Lm-LLO-E7, virulence increased with each passage up to passage 2 (FIG. 11A). The plasmid-containing construct, Lm-LLO-E7, demonstrated the most dramatic increase in virulence. Prior to passage, the initial immunizing dose of Lm-LLO-E7 had to be increased to $10^7$ bacteria and the spleen had to be harvested on day 2 in order to recover bacteria (whereas an initial dose of $10^5$ bacteria for Lm-Gag was harvested on day 3). After the initial passage, the standard dosage of Lm-LLO-E7 was sufficient to allow harvesting on day 3. For Lm-E7, virulence increased by 1.5 orders of magnitude over unpassaged bacteria (FIG. 11B).

Thus, passage through mice increases the virulence of *Listeria* vaccine strains.

Passaging Increases the Ability of *L. monocytogenes* to Induce CD8+ T Cells

Figure 12:
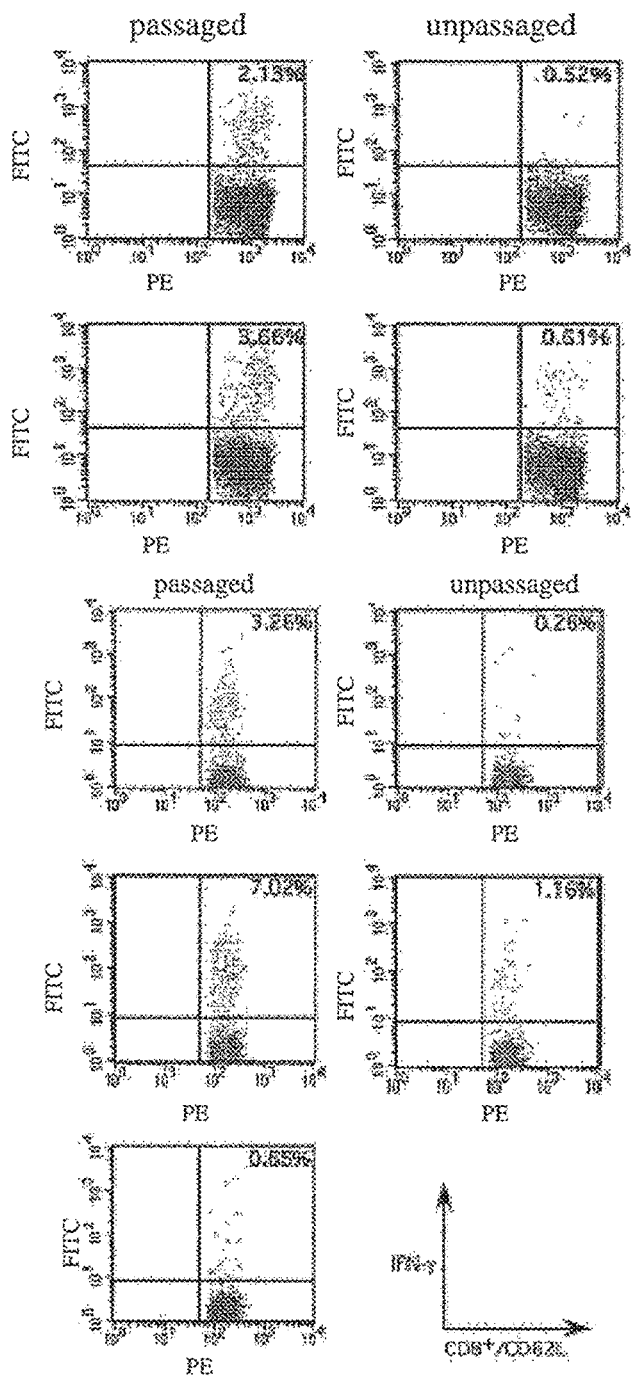
FIG. 12. Induction of antigen-specific CD8$^+$ T-cells for HIV-Gag and LLO after administration of passaged Lm-Gag versus unpassaged Lm-Gag. Mice were immunized with $10^3$ (A, B, E, F) or $10^5$ (C, D, G, H) CFU passaged *Listeria* vaccine vectors, and antigen-specific T-cells were analyzed. B, D, F, H: unpassaged *Listeria* vaccine vectors. A-D immune response to MHC class I HIV-Gag peptide. E-H: immune response to an LLO peptide. I: splenocytes from mice immunized with $10^5$ CFU passaged Lm-Gag stimulated with a control peptide from HPV E7.

Next, the effect of passaging on induction of antigen-specific CD8+ T cells was determined by intracellular cytokine staining with immunodominant peptides specific for MHC-class I using HIV-Gag peptide AMQMLKETI (SEQ ID No: 24) and LLO 91-99 (GYKDGNEYI; SEQ ID No: 25). Injection of $10^3$ CFU passaged bacteria (Lm-Gag) into mice elicited significant numbers of HIV-Gag-specific CD8+ T cells, while the same dose of non-passaged Lm-Gag induced no detectable Gag-specific CD8+ T cells. Even increasing the dose of unpassaged bacteria 100-fold did not compensate for their relative avirulence; in fact, no detectable Gag-specific CD8+ T cells were elicited even at the higher dose. The same dose increase with passaged bacteria increased Gag-specific T cell induction by 50% (FIG. 12). The same pattern of induction of antigen-specific CD8+ T cells was observed with LLO-specific CD8+ T cells, showing that these results were not caused by the properties of the passenger antigen, since they were observed with LLO, an endogenous *Listeria* antigen.

Thus, passage through mice increases the immunogenicity of *Listeria* vaccine strains.

Example 13

A PrfA-Containing Plasmid is Stable in an LM Strain with a PrfA Deletion in the Absence of Antibiotics Materials and Experimental Methods Bacteria

*L. monocytogenes* strain XFL7 contains a 300 base pair deletion in the prfA gene XFL7 carries pGG55 which partially restores virulence and confers CAP resistance, and is described in United States Patent Application Publication No. 200500118184.

Development of Protocol for Plasmid Extraction from *Listeria*

1 mL of *Listeria monocytogenes* Lm-LLO-E7 research working cell bank vial was inoculated into 27 mL BH1 medium containing 34 µg/mL CAP and grown for 24 hours at 37° C. and 200 rpm.

Seven 2.5 mL samples of the culture were pelleted (15000 rpm for 5 minutes), and pellets were incubated at 37° C. with 50 µl lysozyme solution for varying amounts of time, from 0-60 minutes.

Lysozyme Solution:
29 µl 1 M dibasic Potassium Phosphate
21 µl 1 M monobasic Potassium Phosphate
500 µl 40% Sucrose (filter sterilized through 0.45/µm filter)
450 µl water
60 µl lysozyme (50 mg/mL)

After incubation with the lysozyme, the suspensions were centrifuged as before and the supernatants discarded. Each pellet was then subjected to plasmid extraction by a modified version of the QIAprep Spin Miniprep Kit® (Qiagen, Germantown, Md.) protocol. The changes to the protocol were as follows:
1. The volumes of buffers PI, P2 and N3 were all increased threefold to allow complete lysis of the increased biomass.
2. 2 mg/mL of lysozyme was added to the resuspended cells before the addition of P2. The lysis solution was then incubated at 37° C. for 15 minutes before neutralization.
3. The plasmid DNA was resuspended in 30 µL rather than 50 µL to increase the concentration.

In other experiments, the cells were incubated for 15 min in P1 buffer+Lysozyme, then incubated with P2 (lysis buffer) and P3 (neutraliztion buffer) at room temperature.

Equal volumes of the isolated plasmid DNA from each subculture were run on an 0.8% agarose gel stained with ethidium bromide and visualized for any signs of structural or segregation instability.

The results showed that plasmid extraction from *L. monocytogenes* Lm-LLO-E7 increases in efficiency with increasing incubation time with lysozyme, up to an optimum level at approximately 50 minutes incubation.

These results provide an effective method for plasmid extraction from *Listeria* vaccine strains.

Replica Plating

Dilutions of the original culture were plated onto plates containing LB or TB agar in the absence or presence of 34 µg/mL CAP. The differences between the counts on selective and non-selective agar were used to determine whether there was any gross segregational instability of the plasmid.

Results

The genetic stability (i.e. the extent to which the plasmid is retained by or remains stably associated with the bacteria in the absence of selection pressure; e.g. antibiotic selection pressure) of the pGG55 plasmid in *L. monocytogenes* strain XFL7 in the absence of antibiotic was assessed by serial sub-culture in both Luria-Bertani media (LB: 5 g/L NaCl, 10 g/ml soy peptone, 5 g/L yeast extract) and Terrific Broth media (TB: 10 g/L glucose, 11.8 g/L soy peptone, 23.6 g/L yeast extract, 2.2 g/L $KH_2PO_4$, 9.4 g/L $K_2HPO_4$), in duplicate cultures. 50 mL of fresh media in a 250 mL baffled shake flask was inoculated with a fixed number of cells (1 ODmL), which was then subcultured at 24 hour intervals. Cultures were incubated in an orbital shaker at 37° C. and 200 rpm. At each subculture the $OD_{600}$ was measured and used to calculate the cell doubling time (or generation) elapsed, until 30 generations were reached in LB and 42 in TB. A known number of cells (15 ODmL) at each subculture stage (approximately every 4 generations) were pelleted by centrifugation, and the plasmid DNA was extracted using the Qiagen QIAprep Spin Miniprep® protocol described above. After purification, plasmid DNA was subjected to agarose gel electrophoresis, followed by ethidium bromide staining. While the amount of plasmid in the preps varied slightly between samples, the overall trend was a constant amount of plasmid with respect to the generational number of the bacteria (FIGS. 13A-B). Thus, pGG55 exhibited stability in strain XFL7, even in the absence of antibiotic.

Figure 14:
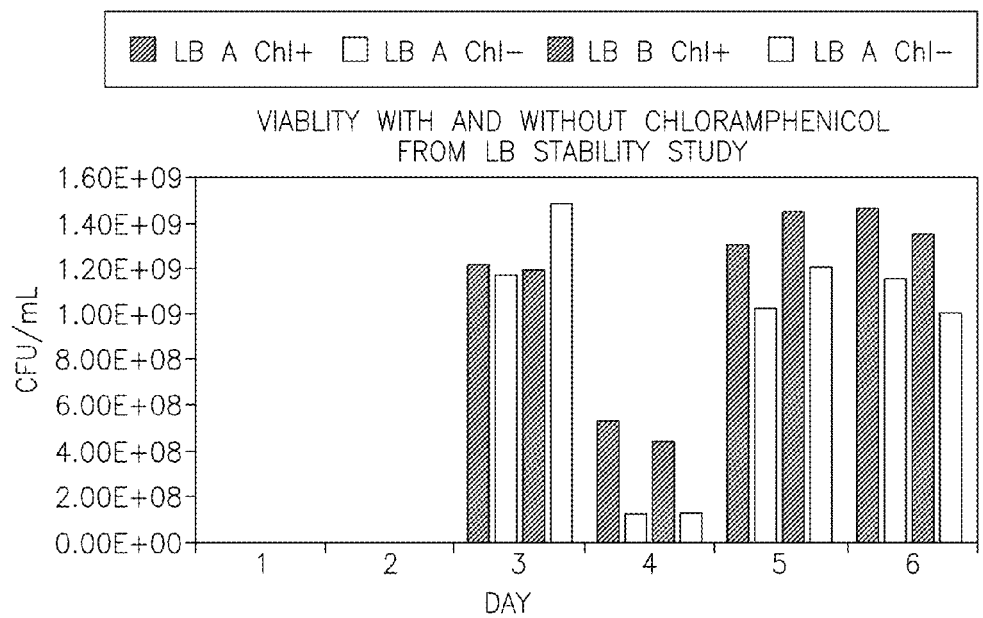
FIG. 14. Numbers of viable bacteria chloramphenicol (CAP)-resistant and CAP-sensitive colony-forming units (CFU) from bacteria grown in LB. Dark bars: CAP$^+$; white bars: CAP$^-$. The two dark bars and two white bars for each time point represent duplicate samples.
Figure 15:
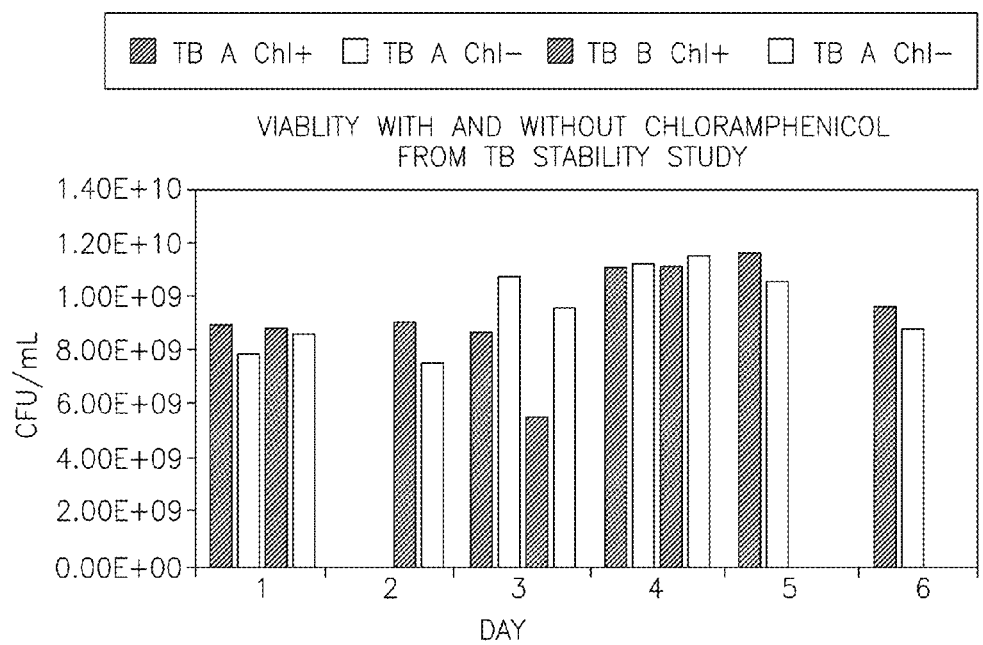
FIG. 15. Numbers of viable bacteria CAP-resistant and CAP-sensitive CFU from bacteria grown in TB. Dark bars: CAP+; white bars: CAP. The two dark bars and two white bars for each time point represent duplicate samples.

Plasmid stability was also monitored during the stability study by replica plating on agar plates at each stage of the subculture. Consistent with the results from the agarose gel electrophoresis, there was no overall change in the number of plasmid-containing cells throughout the study in either LB or TB liquid culture (FIGS. 14 and 15, respectively).

These findings demonstrate that prfA-encoding plasmids exhibit stability in the absence of antibiotic in *Listeria* strains containing mutations in prfA.

Example 14

Optimization of Cryopreservation Conditions for Listeria Vaccine Strains

Materials and Experimental Methods

An LB Research Working Cell Bank (RCB) was produced by the following protocol: 5 ODmL samples were taken from 200 mL cultures grown in LB or TB with 34 μg/mL CAP in 2 L shake flasks at several different $OD_{600}$. The 5 ODmL samples were cryopreserved using 20% v/v glycerol and frozen at less than −70° C. for one day, then were thawed and used to inoculate 50 mL of the same media used for the starter cultures. The initial growth kinetics of these cultures was measured by monitoring the $OD_{600}$ and comparing the growth curves for any sign of lag phase.

An RWCB containing 50 vials of Lm-LLO-E7, cryopreserved in mid-log phase, was produced. Cells from the original glycerol stocks, CTL 2003#0810N, were streaked out onto an LB-agar plate with 34 μg/mL CAP. After a 24-hour incubation, single colonies were selected and grown in 5 mL of LB-CAP for 24 hours at 37° C., which was then used to inoculate 50 mL of LB-CAP. At an $OD_{600}$ of 0.7, cells were cryopreserved after adding glycerol to 20% v/v. The culture was 1-mL aliquots were placed into fifty sterile cryovials and stored below −70° C.

Results

Figure 16:
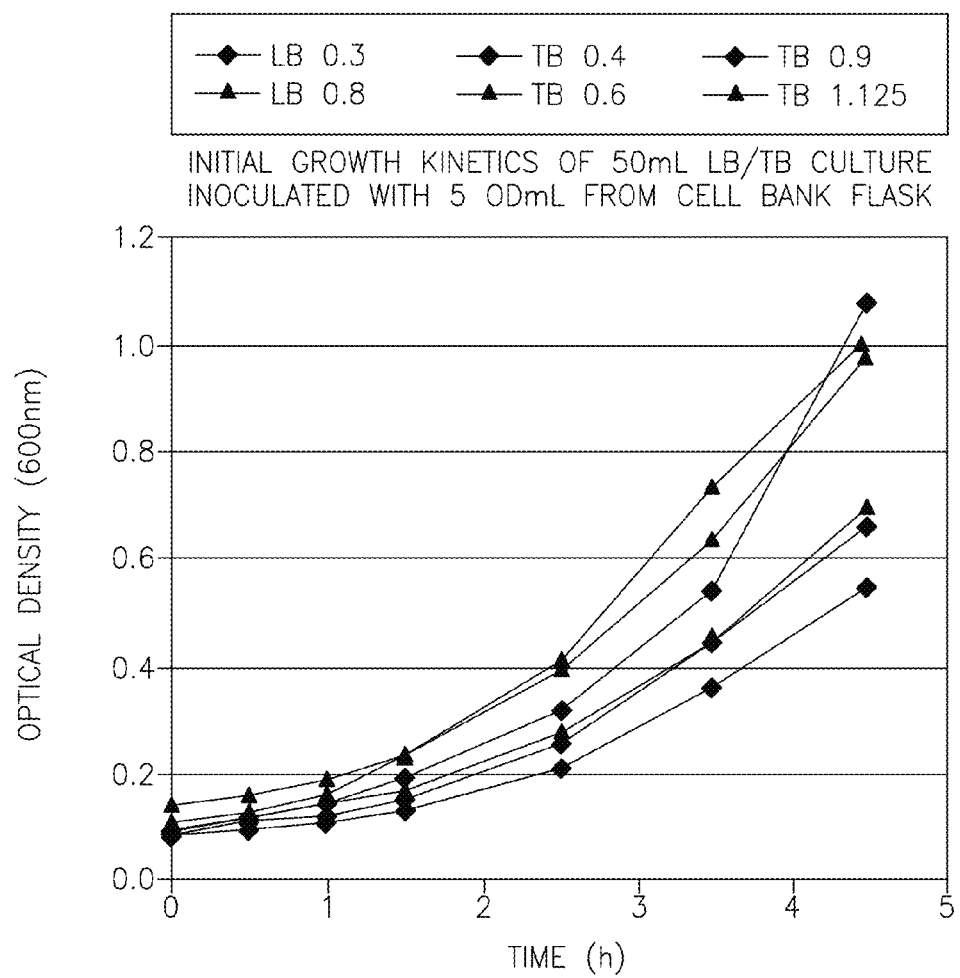
FIG. 16. Growth of *L. monocytogenes* following short-term cryopreservation.

In order to determine the optimum culture density at which to cryopreserve the *L. monocytogenes* strain XFL7 carrying the pGG55 plasmid (which will be referred to as Lm-LLO-E7), bacteria were grown in 200 mL (milliliter) baffled shake flasks in either LB or TB. At various 600 Å optical densities ($OD_{600}$), 5 ODmL (i.e. the product of the $OD_{600}$ reading and the volume of culture in ml) aliquots were removed, glycerol was added to 20% v/v, and the cells were frozen at −70° C. After 24 h (hours) storage at −70° C., the 5 ODmL samples were thawed and used to inoculate 50 mL of fresh media of the same type (LB or TB), and initial growth kinetics of the cultures were monitored. All the cultures immediately entered exponential growth without showing any signs of a lag phase (FIG. 16). Thus, among the $OD_{600}$ utilized, the highest $OD_{600}$ (0.8 for LB and 1.1 for TB) were determined to be optimum for short-term cryopreservation.

Figure 17:
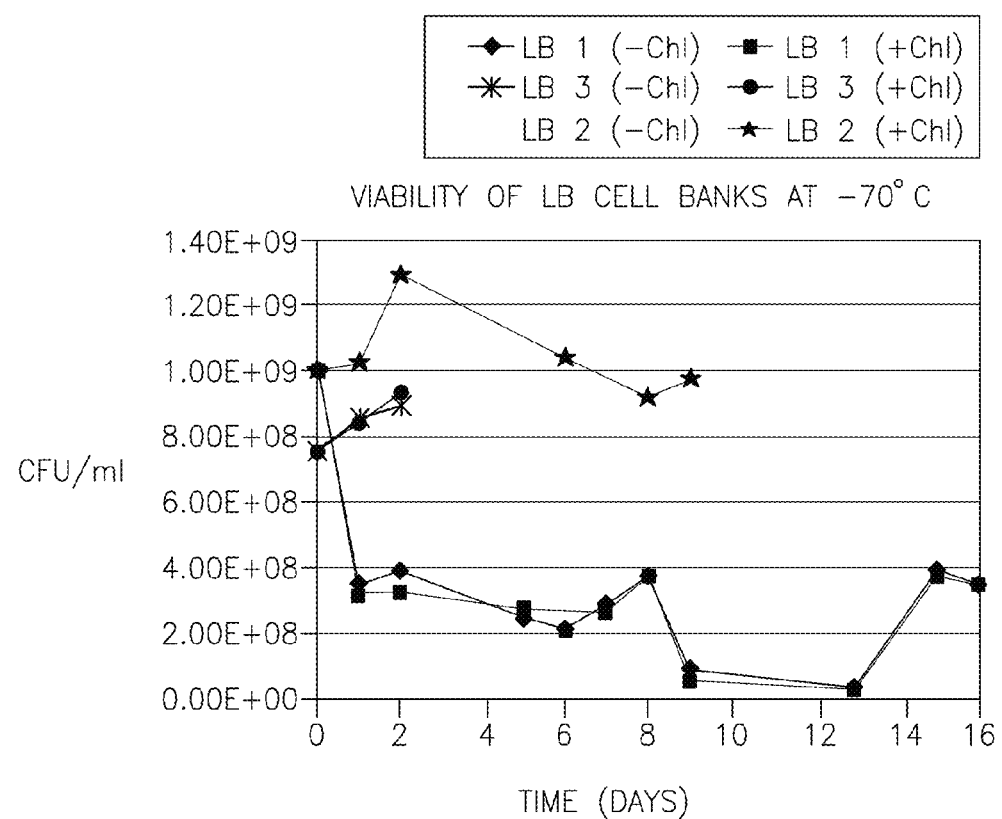
FIG. 17. Viability of LB RCB following storage at −70° C.

Next, an LB Research Working Cell Bank (RCB) was produced by adding 20% v/v glycerol to an 0.8 $OD_{600}$ culture and storing below −70° C. (see Materials and Experimental Methods section above). Viability of the RCB was determined before freezing by replica plating as described for Example 13. Vials of the RCB were thawed after defined intervals, and viability was determined. As depicted in FIG. 17, the viability in the first LB cell bank appeared to decrease from $1 \times 10^9$ to $3 \times 10^8$ CFU/mL following storage at −70° C.

A second and a third LB RCB were generated, this time at $OD_{600}$ of 0.72 and 0.74, respectively. These two RCB exhibited viabilities ranging between 8 and $12 \times 10^8$ CFU/mL, with no decrease in viability, throughout the course of the study. The difference between these RCB and first are likely due to difference in the $OD_{600}$ at the time of cryopreservation. Thus, an optical density of 0.8 likely corresponds to the end of exponential growth and the beginning of stationary phase of Lm-LLO-E7 in. Consequently, an $OD_{600}$ of 0.7 was used subsequently. The second RCB was assigned the number 2003#0933A and was utilized to inoculate the cultures used in subsequent experiments.

Figure 18:
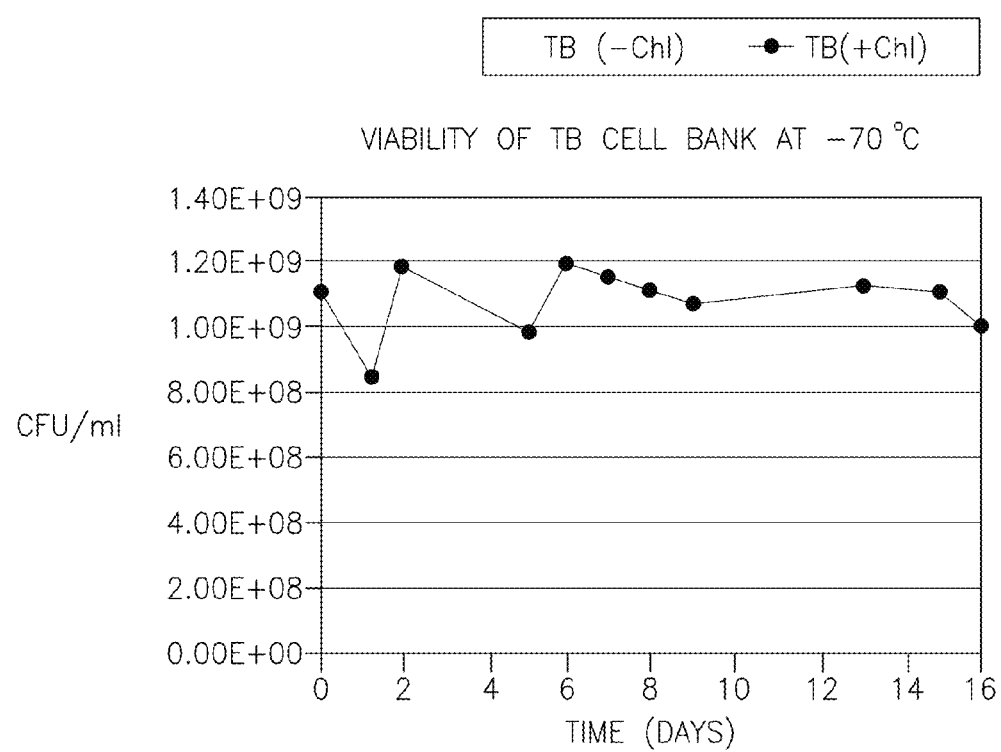
FIG. 18. Viability of TB RCB following storage at −70° C.

In addition, a TB RCB was generated from cultures at an $OD_{600}$ of 1.1. The number of viable cells remained stable at $1 \times 10^9$ CFU/mL (FIG. 18).

These findings demonstrate that methods of the present invention (e.g. conditions of 20% glycerol and $OD_{600}$ of 0.7) have utility in generating cryopreserved *Listeria* vaccine strains and stocks with stable long-term viability.

Example 15

Optimization of Media for Growth of Listeria Vaccine Strains in Shake Flask Fermentations Materials and Experimental Methods Cultures 50 mL volumes of each of the four different defined media were inoculated with 250 μL aliquots of the LB RCB and incubated in 250 mL shake flasks at 37° C. overnight. 20 ODmL of the 50 mL culture were then used to inoculate 200 mL of the same media in 2 L shake flasks. This type of cell propagation procedure encourages viability and exponential growth of the bacteria.

Results

Figure 19:
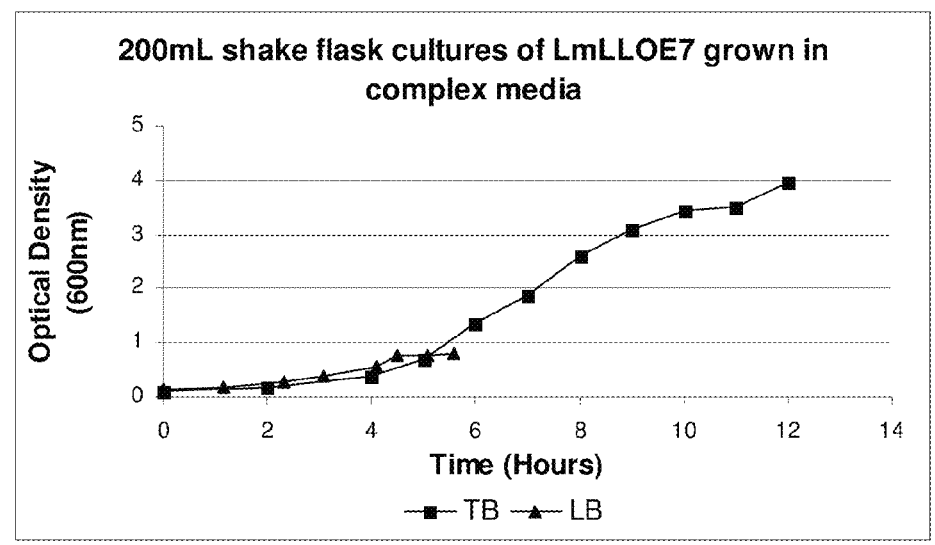
FIG. 19. Growth curve of 200 mL LB and TB cultures of Lm-LLO-E7.

The growth curves of the *Listeria* vaccine strain in LB and TB were investigated in more detail in order to assess its growth potential. The maximum $OD_{600}$ reached in TB and LB were 4 and 0.8 units, which correspond to about $1 \times 10^{10}$ and $9 \times 10^8$ CFU/mL, respectively (FIG. 19).

Experiments were then performed to develop a defined synthetic medium that could support a similar growth to that of TB. A MOPS pH buffer was used instead of a phosphate buffer because its superior buffering capacity would be appropriate for the demands of shake flask growth. The formula outlined in Table 3A below was used as the starting point. In addition to the pH buffer and standard components ("basic components"), the medium contained supplements expected to improve growth of the vaccine strain. These supplements were divided into four groups: essential compounds, amino acids, vitamins and trace elements.

TABLE 3A

Original defined media composition.

| Component | Amount per Litre |
|---|---|
| Basic components | |
| MOPS | 20.93 g |
| $KH_2PO_4$ | 0.656 g |
| $Na_2HPO_4$—$7H_2O$ | 1.639 g |
| Glucose | 10 g |
| $MgSO_4$ | 0.41 g |
| Supplements | |
| Essential components | |
| Ferric Citrate | 0.1 g |
| Methionine | 0.1 g |
| Cysteine | 0.1 g |
| Glutamine | 0.6 g |
| Riboflavin | 5 mg |
| Thioctic acid | 5 μg |
| Amino acids | |
| Leucine | 0.1 g |
| Isoleucine | 0.1 g |
| Valine | 0.1 g |
| Arginine | 0.1 g |
| Histidine | 0.1 g |
| Tryptophan | 0.1 g |
| Phenylalanine | 0.1 g |
| Vitamins | |
| Adenine | 0.25 mg |
| Biotin | 0.5 mg |
| Thiamine HCl | 1 mg |
| Pyridoxal HCl | 1 mg |

TABLE 3A-continued

Original defined media composition.

| Component | Amount per Litre |
|---|---|
| Para-aminobenzoic acid | 1 mg |
| Calcium pantothenate | 1 mg |
| Nicotinamide | 1 mg |
| Trace Elements | |
| Cobalt chloride hexahydrate (CoCl$_2$•6H$_2$O) | 0.02 g |
| Copper (II) chloride dihydrate (CuCl$_2$•2H$_2$O) | 0.019 g |
| Boric acid (H$_3$BO$_3$) | 0.016 g |
| Manganese sulfate monohydrate (MnSO$_4$•H$_2$O) | 0.016 g |
| Sodium molybdate dihydrate (Na$_2$MoO$_4$•2H$_2$O) | 0.02 g |
| Zinc chloride heptahydrate (ZnCl$_2$•7H$_2$O) | 0.02 g |
| Ferric Sulfate (Fe$_2$(SO$_4$)$_3$ × H$_2$O) | 0.01 g |
| Calcium Chloride dihydrate (CaCl$_2$•2H$_2$0) | 0.01 g |

In order to determine whether supplementation with the three latter groups (amino acids, vitamins, trace elements) improved the growth of Lm-LLO-E7, bacteria were grown in 50 mL starter cultures, then in 250 mL cultures, of the following media in shake flasks:
1. Bulk medium (i.e. water plus the basic components in Table 3A), essential components, amino acids, vitamins and trace elements.
2. Bulk medium, essential components, amino acids and vitamins.
3. Bulk medium, essential components and amino acids.
4. Bulk medium and essential components.

Figure 20:
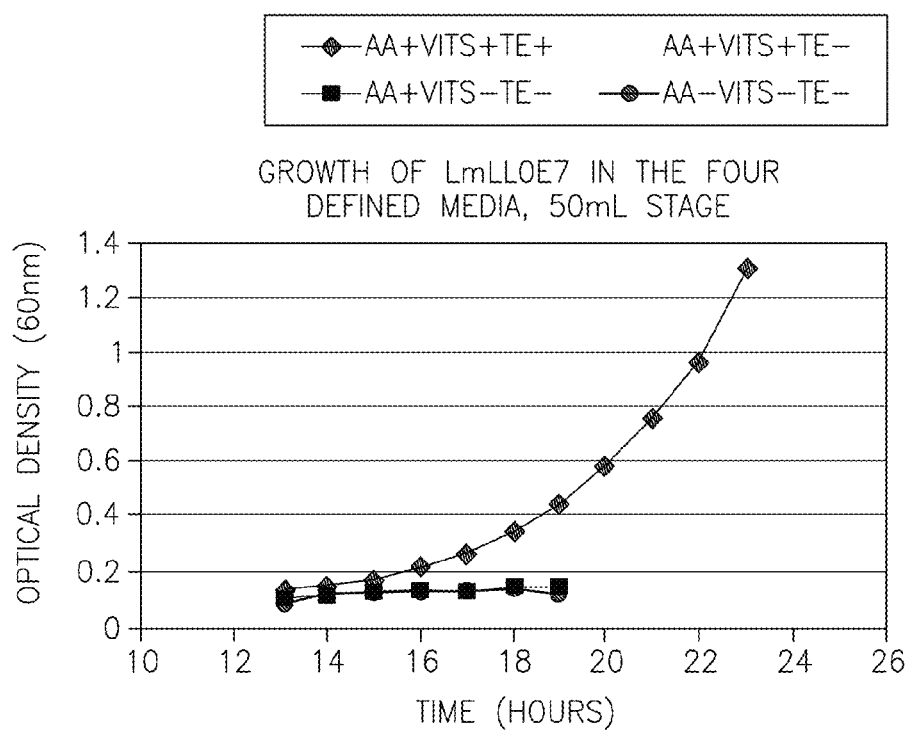
FIG. 20. Growth of Lm-LLO-E7 in 4 defined media with and without AA, vitamins and trace elements, at the 50 mL stage. "AA+Vits+TE+" denotes bulk medium, essential components, AA, vitamins and trace elements; "AA+Vits+TE−" denotes bulk medium, essential components, AA, and vitamins; "AA+Vits−TE−" denotes bulk medium, essential components, and AA; "AA−Vits−TE−" denotes bulk medium and essential components.
Figure 21:
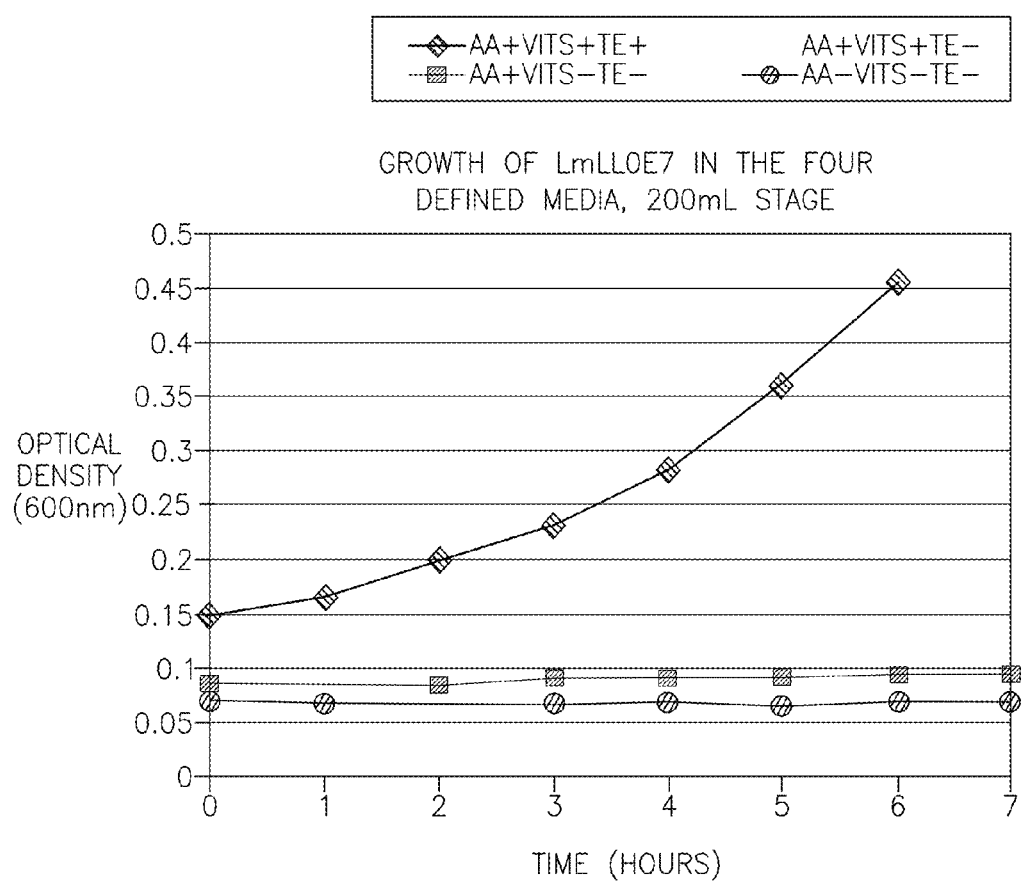
FIG. 21. Growth of Lm-LLO-E7 in 4 defined media with and without amino acids, vitamins and trace elements, at the 200 mL stage. Groups are labeled as for FIG. 23.

Presence of both AA and vitamins was necessary to support significant growth in the 50 mL cultures, and the presence of trace elements enhanced the growth rate (FIG. 20). However, at the 200 mL stage the presence of trace elements did not influence the growth rate (FIG. 21). It is possible that the trace elements supported the adaptation of Lm-LLO-E7 from the LB cell bank into the defined medium at the 50 mL stage. Based on these results, all four of the groups in Table 3A were included in the defined medium in subsequent experiments.

The next experiment investigated the effect of increasing the concentrations of the 4 groups of supplements of Table 3. The concentrations of all the components of these four groups were increased by a factor of 2 or 4 to produce "2X" and "4X" defined media, respectively. In addition, 4X defined media containing 1, 2 or 3 g/L of inorganic nitrogen in the form of NH$_4$SO$_4$ were tested. The growth of these five cultures was compared to the media of Table 3A ("control") in the 50 mL-200 mL protocol described above.

Figure 22:
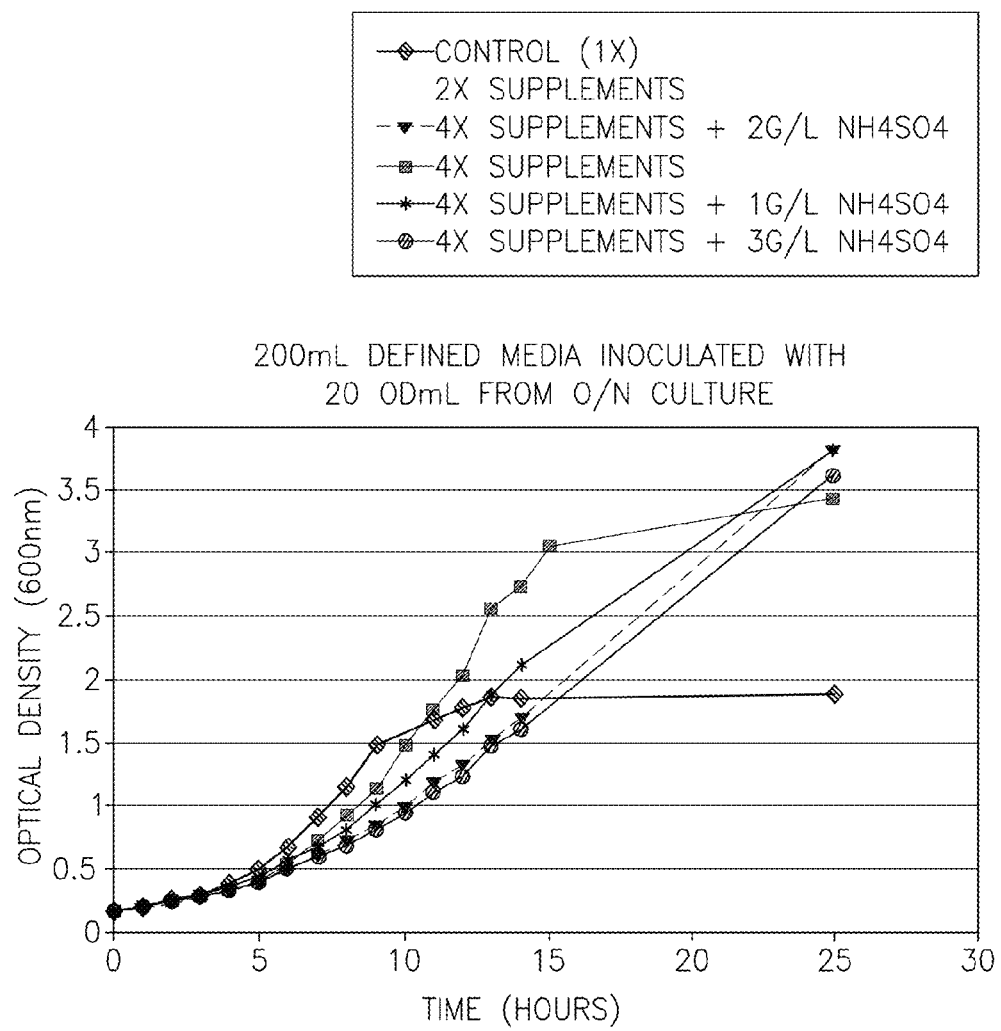
FIG. 22. Growth of Lm-LLO-E7 in 200 mL cultures of defined media with different concentrations of supplements, with and without inorganic nitrogen.

All media tested exhibited similar growth for the first four hours. At this point, the growth in the control media began to decelerate, stopping completely at 13 hours, while the 2X and 4X media continued to support exponential growth (FIG. 22). The flasks containing the 2X and 4X media reached final OD$_{600}$ of 2.5 units and 3.5, respectively. Inclusion of NH$_4$SO$_4$ slightly increased final biomass concentrations, but considerably decreased the growth rate.

Thus, increasing the nutrient level, but not inclusion of NH$_4$SO$_4$, significantly improved the growth of the vaccine strain in defined media. Based on these results, NH$_4$SO$_4$ was not included in subsequent experiments.

Figure 23:
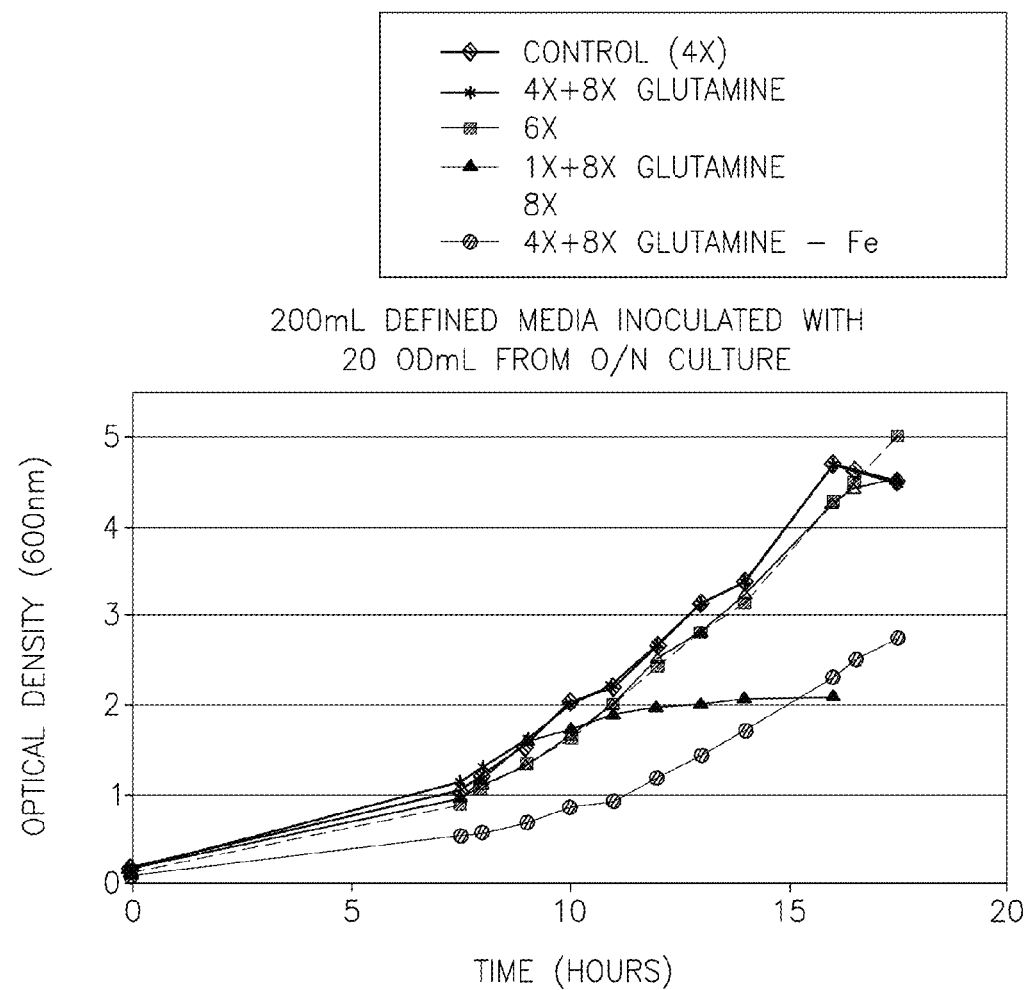
FIG. 23. Growth of Lm-LLO-E7 in 200 mL cultures of defined media supplemented with different concentrations of supplements, with and without glutamine and iron.

Next, the effect in 50 mL and 200 mL cultures of the following additional modifications to the media was examined: 1) further increasing the concentration of the 4 groups of supplements from Table 3A (to 6 and 8 times the original concentration); 2) increasing the concentration of glutamine (a source of organic nitrogen) to 8 times the original concentration; and 3) removing iron from the media. As depicted in FIG. 23 (results from 200 mL cultures), further increasing the concentration of either glutamine or the 4 groups of supplements did not enhance the final biomass concentration of Lm-LLO-E7. Removal of iron, by contrast, reduced the maximum biomass concentration.

The effect of increasing the glucose concentration of the 4X media was examined Increasing glucose concentration from 10 to 15 g/L significantly improved growth rate and biomass.

The final OD$_{600}$ of each of the 4X supplements was 4.5, which corresponded to $1.1 \times 10^{10}$ CFU/mL, approximately the same as the final biomass obtained with TB. Thus, a defined media was developed that supported growth of a Listeria vaccine strain to the same extent as TB.

In conclusion, media containing 4× the original concentration of the four groups of supplements from Table 3A (referred to henceforth as "4X media") supported optimal growth of Lm-LLO-E7 in 50 mL and 200 mL shake flask cultures. Iron was required for optimal growth. Increasing the glucose from 10 to 15 g/L increased the total biomass achieved. The resulting optimized defined media recipe is depicted in Table 3B.

TABLE 3B

Optimized defined media composition.

| COMPONENT | AMOUNT PER LITRE |
|---|---|
| BASIC COMPONENTS | |
| KH$_2$PO$_4$ | 2.2 g |
| Na$_2$HPO$_4$—7H$_2$O | 10.4 g |
| Glucose | 15 g |
| MgSO$_4$ | 0.41 g |
| SUPPLEMENTS | |
| Essential components | |
| Ferric Citrate | 0.4 g |
| Methionine | 0.4 g |
| Cysteine | 0.4 g |
| Glutamine | 2.4 g |
| Riboflavin | 20 mg |
| Thioctic acid | 20 µg |
| Amino acids | |
| Leucine | 0.4 g |
| Isoleucine | 0.4 g |
| Valine | 0.4 g |
| Arginine | 0.4 g |
| Histidine | 0.4 g |
| Tryptophan | 0.4 g |
| Phenylalanine | 0.4 g |
| Vitamins | |
| Adenine | 0.25 g |
| Biotin | 2 mg |
| Thiamine HCl | 4 mg |
| Pyridoxal HCl | 4 mg |
| Para-aminobenzoic acid | 4 mg |
| Calcium pantothenate | 4 mg |
| Nicotinamide | 4 mg |
| Trace Elements | |
| Cobalt chloride hexahydrate (CoCl$_2$•6H$_2$O) | 0.02 g |
| Copper (II) chloride dihydrate (CuCl$_2$•2H$_2$O) | 0.019 g |
| Boric acid (H$_3$BO$_3$) | 0.016 g |
| Manganese sulfate monohydrate (MnSO$_4$•H$_2$O) | 0.016 g |
| Sodium molybdate dihydrate (Na$_2$MoO$_4$•2H$_2$O) | 0.02 g |
| Zinc chloride heptahydrate (ZnCl$_2$•7H$_2$O) | 0.02 g |
| Ferric Sulfate (Fe$_2$(SO$_4$)$_3$ × H$_2$O) | 0.01 g |
| Calcium Chloride dihydrate (CaCl$_2$•2H$_2$O) | 0.01 g |
| Citric Acid | 0.6 g |

Example 16

Optimization of Media for Growth of Listeria Vaccine Strains in Batch Fermentations Materials and Experimental Methods FT Applikon 5/7L fermenter vessels containing 4500 mL of either TB or defined medium with 34 µg/mfL CAP were utilized in this Example. 20 ODmL of Lm-LLO-E7 was used to inoculate a 200 mL starter culture containing CAP, which was grown at 37° C. in an orbital shaker at 200 rpm for 10 hours until it reached mid-log phase; 450 ODmL of this culture was used to inoculate the fermenter vessels. The temperature, pH and dissolved oxygen concentration were continuously monitored and controlled during the fermentation at levels of 37° C., 7.0, and 20% of saturation.

Results

Factors such as dissolved oxygen concentration or pH likely limited the growth of Lm-LLO-E7 in the previous Example, as they are not controlled in shake flasks. Consistent with this possibility, the pH of the cultures in the shake flasks had decreased to approximately 5.5 units. In a batch fermenter, by contrast, pH and dissolved oxygen levels are continuously monitored and controlled. Thus, separate experiments were performed in this Example to optimize the media used for batch fermentations.

Figure 24A:
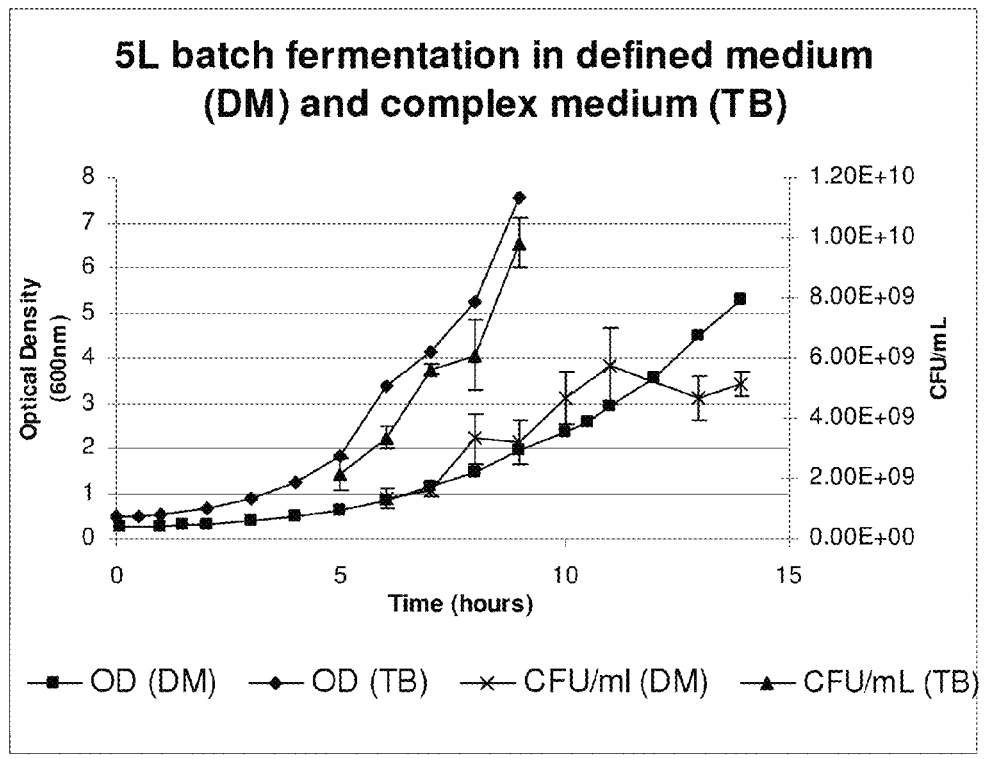
FIGS. 24A-24C.

200 mL cultures of Lm-LLO-E7 were grown overnight in either TB or the defined medium from Table 3B until they reached mid-log phase ($OD_{600}$ of 1-2). 450 ODmLs of the starter culture was then used to inoculate 5 L batch fermenters containing the same media. The bacteria grown in the TB culture began to grow exponentially immediately upon innoculation, with a specific growth rate of 0.5 $h^{-1}$, then entered into a deceleration phase about 7 hours after inoculation, reaching stationary phase at a viable cell density of $2.1 \times 10^{10}$ CFU/mL (FIG. 24A). The bacteria grown in the defined media also exhibited exponential growth; however, the growth rate was 0.25 $h^{-1}$, and the final viable cell density was $1.4 \times 10^{10}$ CFU/mL. A total yield of $8.9 \times 10^{13}$ CFR was obtained from the batch fermentation. Both batch fermentations entered into stationary phase as a result of carbon limitation, as evidenced by the finding that the glucose concentration had reached zero at stationary phase. Since LM cannot utilize AA as a carbon source, the cells were unable to grow in the absence of carbohydrate.

Figure 24B:
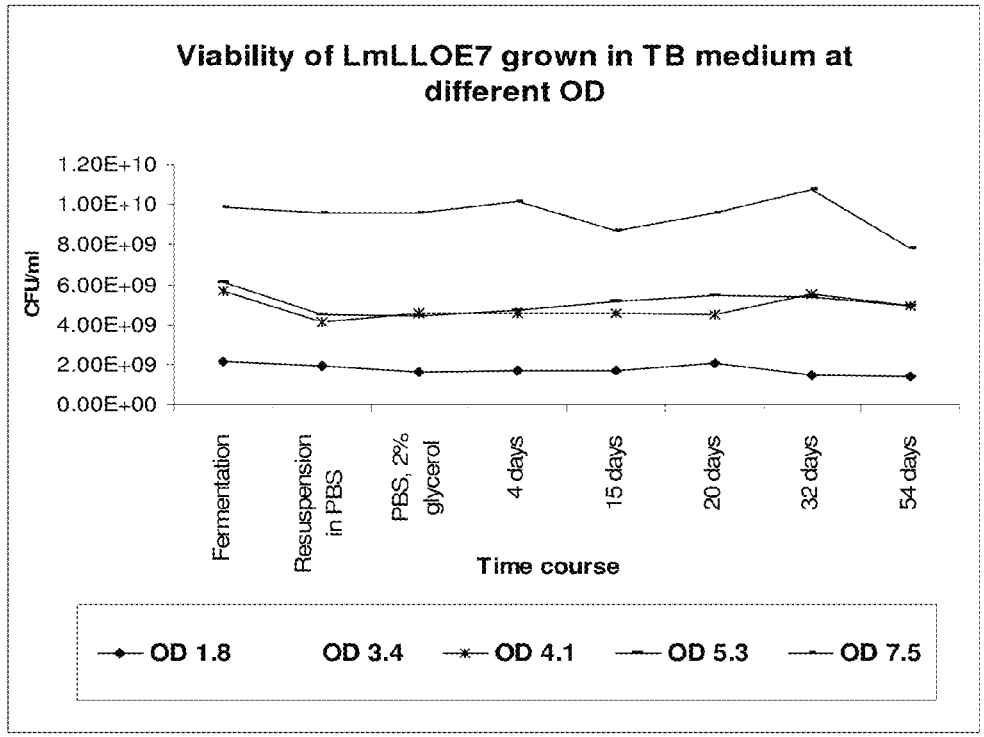
Figure 24C:
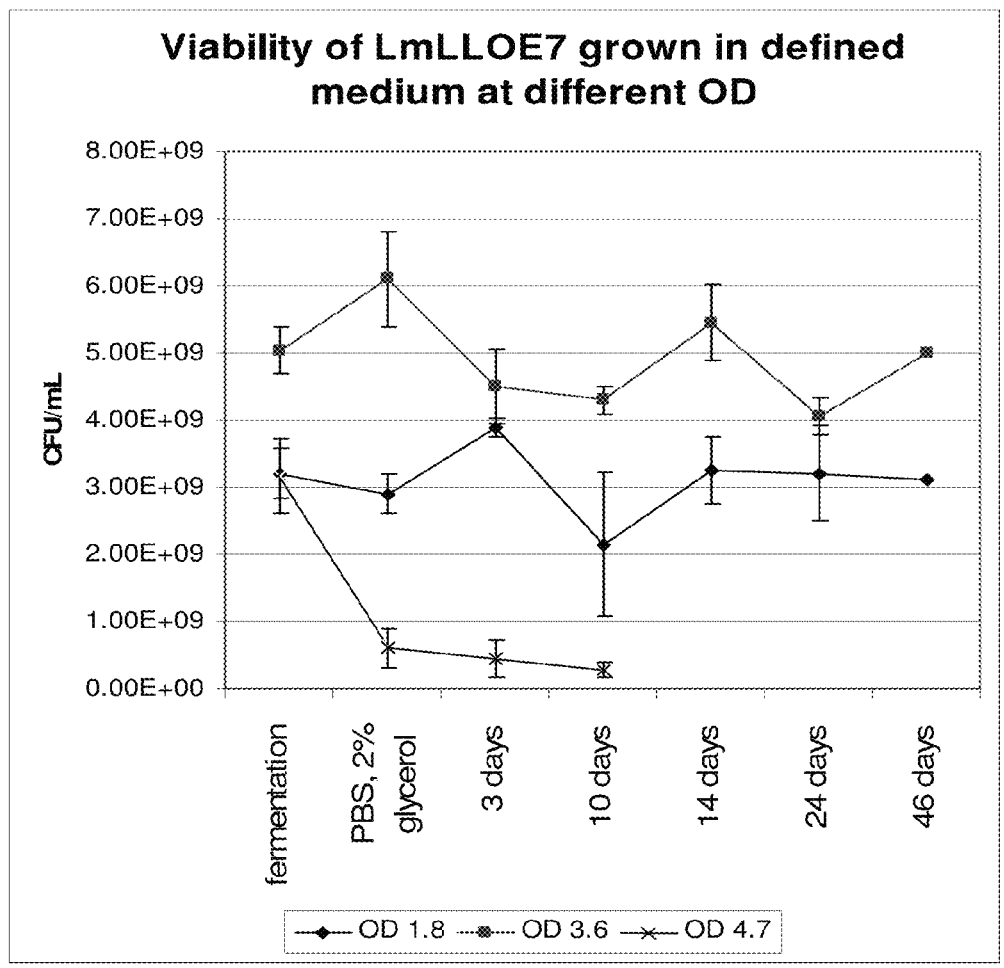
Figure 25:
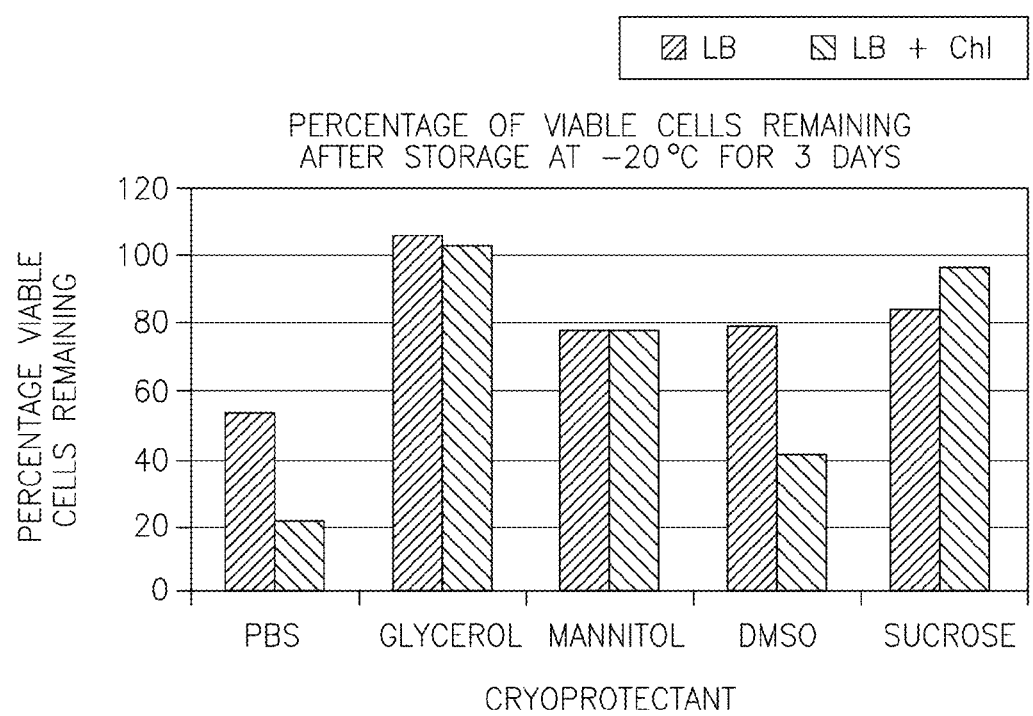
FIG. 25. Percentage of viable cells remaining after storage at −20° C. for 3 days.
Figure 26:
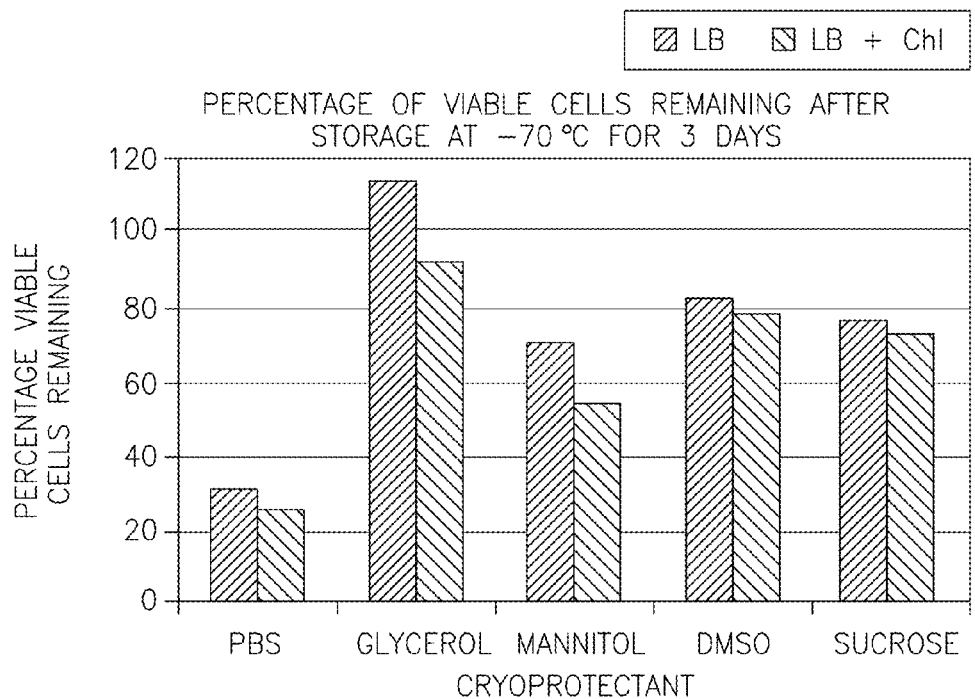
FIG. 26. Percentage of viable cells remaining after storage at −70° C. for 3 days FIGS. 27A-27C.
Figure 27A:
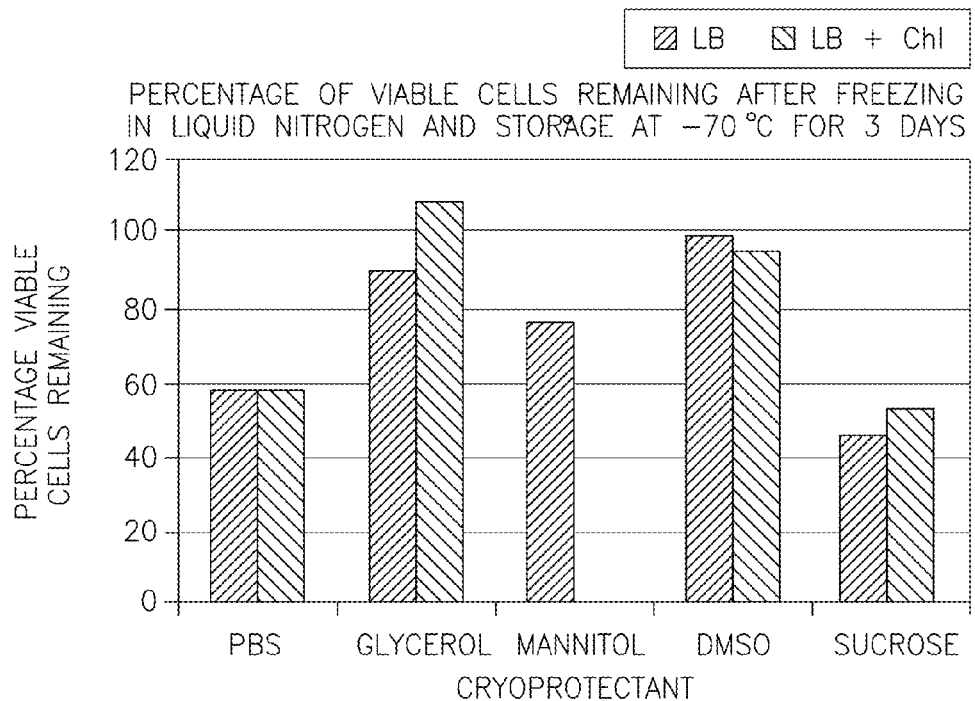
FIG. 27A. Percentage of viable cells remaining following snap freezing in liquid nitrogen and storage at −70° C. for 3 days.
Figure 27B:
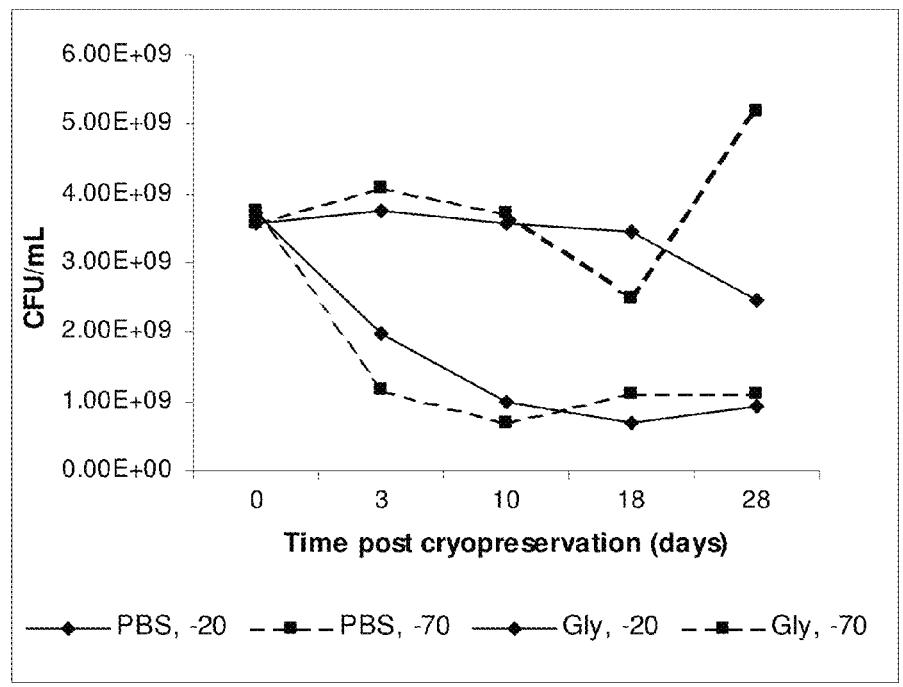
FIG. 27B. Summary of viability studies for several conditions.
Figure 27C:
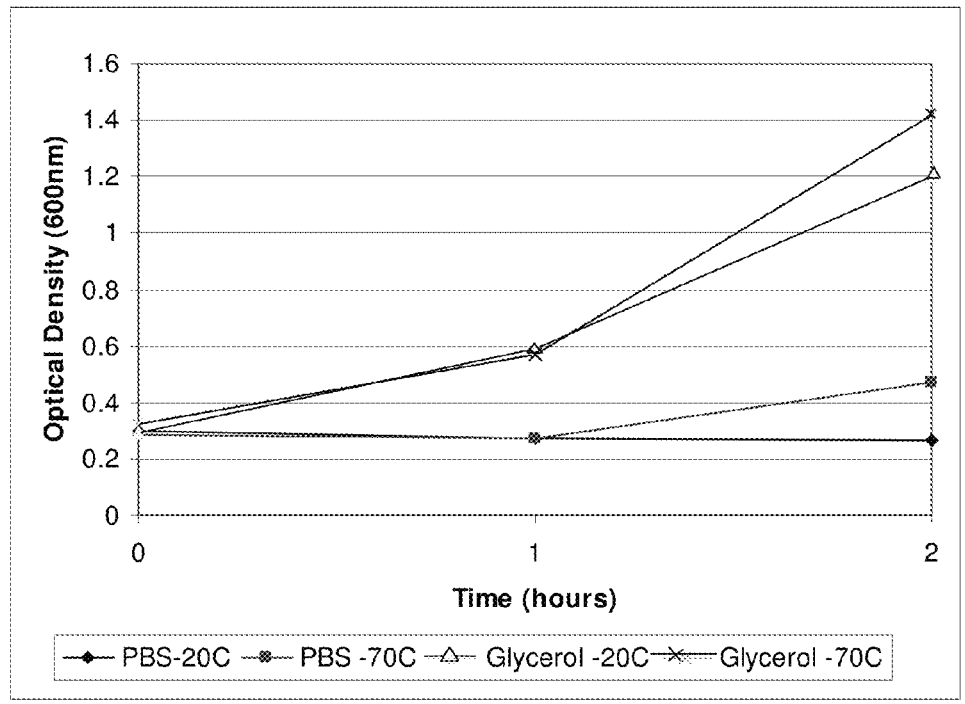
FIG. 27C. Growth kinetics of cryopreserved samples after thawing.
Figure 28:
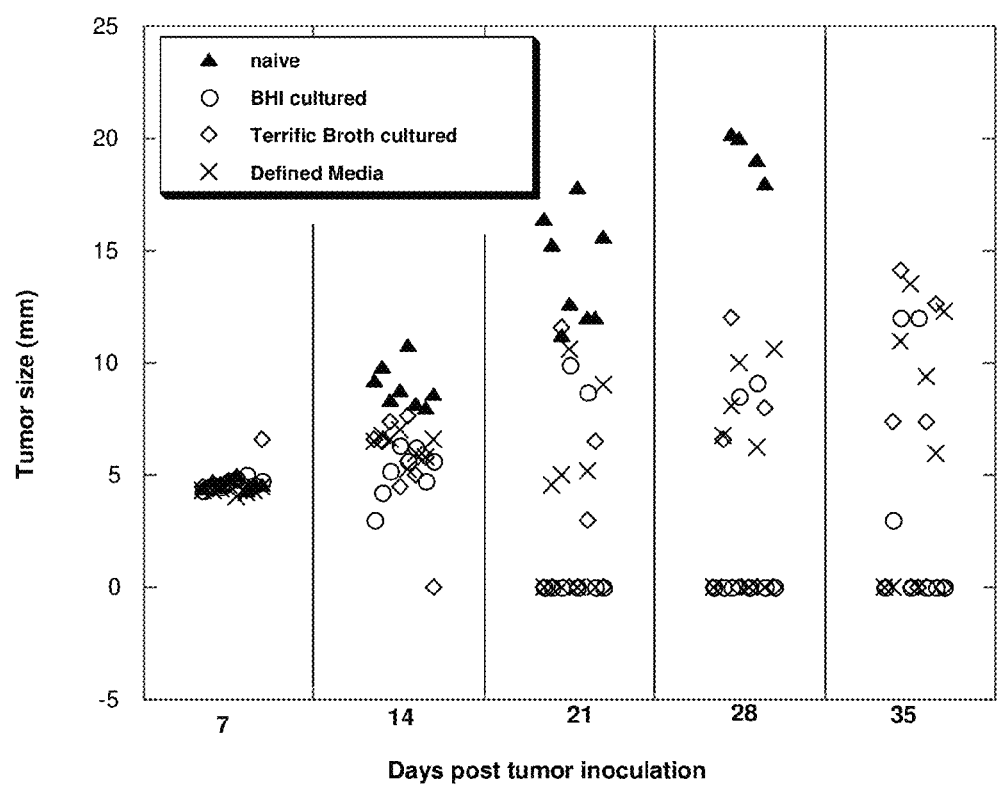
FIG. 28. *Listeria* vaccine vectors grown in defined media effectively protect mice against growth of established tumors. "BHI cultured"—vectors cultured in Brain-Heart Infusion media "Terrific Broth cultured" and "defined media cultured"—vectors cultured in indicated media.

At all densities tested, the bacteria grown in TB retained their viability throughout subsequent steps in the process (FIG. 24B). Bacteria grown in defined media maintained their viability up to an OD of 3-4 (FIG. 24C).

It was further found that, to prevent iron precipitation, the iron and magnesium salts could be dissolved separately in water and heated to 60° C., then filter-sterilized and simultaneously added to the fermenter culture medium.

Example 17

Further Optimization of Cryopreservation Conditions for Listeria Vaccine Strains The next experiment examined the viability of cryopreserved Lm-LLO-E7 in the presence of each of 4 different additives: namely, glycerol, mannitol, DMSO and sucrose. PBS was used as a control. In addition, three different storage methods were compared: −20° C., −70° C., and snap freezing in liquid nitrogen followed by storage at −70° C.

A shake flask containing 200 mL of the 4X media from Table 3B was grown to an $OD_{600}$ of 1.6. Fifteen 10 mL samples were pelleted by centrifugation, the supernatants removed, and the cells resuspended in 10 mL of PBS containing 2% w/v of the appropriate cryoprotectant. One mL aliquots of each resuspended sample were transferred into vials and stored using the appropriate method. Viability was measured by replica plating (with and without CAP) before storage and after 3-28 days or storage, and the percentage of viable cells remaining was calculated. 2% w/v glycerol at −70° C. was found to be the best short-term cryopreservation method; with the bacteria exhibiting approximately 100% viability. The cell viability remained high over the 3-28 days under several of the conditions utilized (FIGS. 25-28).

Conclusion-Examples 13-18

The genetic stability of the pGG55 plasmid in Lm-LLO-E7 showed no signs of structural or segregational instability after 35 or 42 cell generations. A RCB was produced, and the viability of the cells preserved in the RCB remained constant at approximately $1 \times 10^9$ CFU/mL after freezing and thawing. The ability of two complex media to support the growth of Lm-LLO-E7 was assessed. LB and TB supported growth to maximum cell densities of approximately $9 \times 10^8$ and $1 \times 10^{10}$ CFU/mL, corresponding to $OD_{600}$ of 0.8 and 4.0 units, respectively. A defined media that supported growth to an extent similar to TB was developed and optimized for shake flask cultivations. Lm-LLO-E7 reached a higher biomass concentration in 5 L batch fermenters compared to shake flask cultivation, likely due to the ability to control the pH in fermenters. The optimum method for cryopreservation of the cells was also investigated. Lm-LLO-E7 cryopreserved in PBS containing 2% w/v glycerol exhibited approximately 100% viability following storage at less than −70° C. for 3 days.

Having described the embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed:

1. A method of treating cervical dysplasia in a human subject, the method comprising the step of administering to said subject a recombinant *Listeria* strain, said recombinant *Listeria* strain comprising a recombinant polypeptide comprising an N-terminal fragment of an LLO protein, comprising the sequence of SEQ ID NO:1, fused to a Human Papilloma Virus (HPV) E7 antigen, thereby treating a cervical dysplasia in a human subject.

2. The method of claim 1, wherein said administering is intravenous administering.

3. The method of claim 1, wherein said recombinant *Listeria* strain is administered to said human subject at a dose of $5.10^7$, $3.3 \times 10^8$ or from $1 \times 10^9$ to $1 \times 10^{10}$ organisms.

4. The method of claim 1, wherein said recombinant *Listeria* strain is a recombinant *Listeria monocytogenes* strain.

5. The method of claim 1, wherein said recombinant *Listeria* strain has been passaged through an animal host, prior to the step of administering.

6. The method of claim 1, wherein said recombinant polypeptide is expressed by said recombinant *Listeria* strain.

7. The method of claim 1, wherein said recombinant *Listeria* strain comprises a plasmid that encodes said recombinant polypeptide.

8. The method of claim 7, wherein said plasmid comprises a gene encoding a bacterial transcription factor.

9. The method of claim 7, wherein said plasmid comprises a gene encoding a metabolic enzyme.

10. The method of claim 1, further comprising the step of boosting said human subject with said recombinant *Listeria* strain.

11. The method of claim 1, further comprising the step of inoculating said human subject with an immunogenic composition that comprises said E7 antigen.

12. The method of claim 1, wherein said recombinant *Listeria* strain has been stored in a frozen or lyophilized cell bank.

13. The method of claim 12, wherein said recombinant *Listeria* strain exhibits viability upon thawing or reconstitution of greater than 90%.

14. A method of inducing an immune response against a cervical dysplasia in a human subject, the method comprising the step of administering to said subject a recombinant *Listeria* strain, said recombinant *Listeria* strain comprising a recombinant polypeptide comprising an N-terminal fragment of an LLO protein, comprising the sequence of SEQ ID NO: 1, fused to a Human Papilloma Virus (HPV) E7 antigen, thereby inducing an immune response against a cervical dysplasia in a human subject.

15. The method of claim 14, wherein said administering is intravenous administering.

16. The method of claim 14, wherein said recombinant *Listeria* strain is administered to said human subject at a dose of $5.10^7$, $3.3 \times 10^8$ or from $1 \times 10^9$ to $1 \times 10^{10}$ organisms.

17. The method of claim 14, wherein said recombinant *Listeria* strain is a recombinant *Listeria monocytogenes* strain.

18. The method of claim 14, wherein said recombinant *Listeria* strain has been passaged through an animal host, prior to the step of administering.

19. The method of claim 14, wherein said recombinant polypeptide is expressed by said recombinant *Listeria* strain.

20. The method of claim 14, wherein said recombinant *Listeria* strain comprises a plasmid that encodes said recombinant polypeptide.

21. The method of claim 20, wherein said plasmid expresses a *Listeria* transcription factor.

22. The method of claim 20, wherein said plasmid comprises a gene encoding a metabolic enzyme.

23. The method of claim 14, further comprising the step of boosting said human subject with said recombinant *Listeria* strain.

24. The method of claim 14, further comprising the step of inoculating said human subject with an immunogenic composition that comprises said E7 antigen.

25. The method of claim 14, wherein said recombinant *Listeria* strain has been stored in a frozen or lyophilized cell bank.

26. The method of claim 25, wherein said recombinant *Listeria* strain exhibits viability upon thawing or reconstitution of greater than 90%.

* * * * *

SEQUENCE LISTING

```
<160> NUMBER OF SEQ ID NOS: 25

<210> SEQ ID NO 1
<211> LENGTH: 32
<212> TYPE: PRT
<213> ORGANISM: Listeria monocytogenes
```

<400> SEQUENCE: 1

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
                20                  25                  30

<210> SEQ ID NO 2
<211> LENGTH: 14
<212> TYPE: PRT
<213> ORGANISM: Listeria monocytogenes

<400> SEQUENCE: 2

Lys Thr Glu Glu Gln Pro Ser Glu Val Asn Thr Gly Pro Arg
1               5                   10

<210> SEQ ID NO 3
<211> LENGTH: 28
<212> TYPE: PRT
<213> ORGANISM: Listeria monocytogenes

<400> SEQUENCE: 3

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
                20                  25

<210> SEQ ID NO 4
<211> LENGTH: 20
<212> TYPE: PRT
<213> ORGANISM: Listeria monocytogenes

<400> SEQUENCE: 4

Lys Asn Glu Glu Val Asn Ala Ser Asp Phe Pro Pro Pro Pro Thr Asp
1               5                   10                  15

Glu Glu Leu Arg
                20

<210> SEQ ID NO 5
<211> LENGTH: 33
<212> TYPE: PRT
<213> ORGANISM: Listeria monocytogenes

<400> SEQUENCE: 5

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
                20                  25                  30

Arg

<210> SEQ ID NO 6
<211> LENGTH: 17
<212> TYPE: PRT
<213> ORGANISM: Streptococcus pyogenes

<400> SEQUENCE: 6

Lys Gln Asn Thr Ala Ser Thr Glu Thr Thr Thr Thr Asn Glu Gln Pro
1               5                   10                  15

Lys

<210> SEQ ID NO 7
<211> LENGTH: 17

-continued

```
<212> TYPE: PRT
<213> ORGANISM: Streptococcus equisimilis

<400> SEQUENCE: 7

Lys Gln Asn Thr Ala Asn Thr Glu Thr Thr Thr Asn Glu Gln Pro
1               5                   10                  15

Lys

<210> SEQ ID NO 8
<211> LENGTH: 22
<212> TYPE: DNA
<213> ORGANISM: Artificial Sequence
<220> FEATURE:
<223> OTHER INFORMATION: Primer for amplifying E7

<400> SEQUENCE: 8
ggctcgagca tggagataca cc                                           22

<210> SEQ ID NO 9
<211> LENGTH: 28
<212> TYPE: DNA
<213> ORGANISM: Artificial Sequence
<220> FEATURE:
<223> OTHER INFORMATION: Primer for amplifying E7

<400> SEQUENCE: 9
ggggactagt ttatggtttc tgagaaca                                     28

<210> SEQ ID NO 10
<211> LENGTH: 31
<212> TYPE: DNA
<213> ORGANISM: Artificial Sequence
<220> FEATURE:
<223> OTHER INFORMATION: Primer for generating hly promoter and gene
      fragment

<400> SEQUENCE: 10
gggggctagc cctcctttga ttagtatatt c                                 31

<210> SEQ ID NO 11
<211> LENGTH: 28
<212> TYPE: DNA
<213> ORGANISM: Artificial Sequence
<220> FEATURE:
<223> OTHER INFORMATION: Primer for generating hly promoter and gene
      fragment

<400> SEQUENCE: 11
ctccctcgag atcataattt acttcatc                                     28

<210> SEQ ID NO 12
<211> LENGTH: 55
<212> TYPE: DNA
<213> ORGANISM: Artificial Sequence
<220> FEATURE:
<223> OTHER INFORMATION: Primer for amplifying PrfA gene

<400> SEQUENCE: 12
gactacaagg acgatgaccg acaagtgata acccgggatc taaataaatc cgttt       55

<210> SEQ ID NO 13
<211> LENGTH: 27
<212> TYPE: DNA
<213> ORGANISM: Artificial Sequence
<220> FEATURE:
<223> OTHER INFORMATION: Primer for amplifying PrfA gene
```

<400> SEQUENCE: 13
cccgtcgacc agctcttctt ggtgaag                                27

<210> SEQ ID NO 14
<211> LENGTH: 9
<212> TYPE: PRT
<213> ORGANISM: Artificial Sequence
<220> FEATURE:
<223> OTHER INFORMATION: phycoerythrin (PE)-conjugated E7 peptide

<400> SEQUENCE: 14

Arg Ala His Tyr Asn Ile Val Thr Phe
1               5

<210> SEQ ID NO 15
<211> LENGTH: 441
<212> TYPE: PRT
<213> ORGANISM: Listeria monocytogenes

<400> SEQUENCE: 15

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

```
Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
                420                 425                 430

Ile Ser Trp Asp Glu Val Asn Tyr Asp
                435                 440

<210> SEQ ID NO 16
<211> LENGTH: 416
<212> TYPE: PRT
<213> ORGANISM: Listeria monocytogenes

<400> SEQUENCE: 16

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Val Ala Pro Ala Ser Pro Pro Ala Ser
            35                  40                  45

Pro Lys Thr Pro Ile Glu Lys Lys His Ala Asp Glu Ile Asp Lys Tyr
50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
                180                 185                 190

Tyr Ala Gln Ala Tyr Ser Asn Val Ser Ala Lys Ile Asp Tyr Asp Asp
            195                 200                 205

Glu Met Ala Tyr Ser Glu Ser Gln Leu Ile Ala Lys Phe Gly Thr Ala
```

```
                  210                 215                 220
Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
                260                 265                 270

Ala Val Thr Lys Glu Gln Leu Gln Ala Leu Gly Val Asn Ala Glu Asn
                275                 280                 285

Pro Pro Ala Tyr Ile Ser Ser Val Ala Tyr Gly Arg Gln Val Tyr Leu
                290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 17
<211> LENGTH: 529
<212> TYPE: PRT
<213> ORGANISM: Listeria monocytogenes

<400> SEQUENCE: 17

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Met Ala Pro Pro Ala Ser Pro Pro Ala Ser
                35                  40                  45

Pro Lys Thr Pro Ile Glu Lys Lys His Ala Asp Glu Ile Asp Lys Tyr
50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
                115                 120                 125

Ala Leu Val Lys Ala Asn Ser Glu Leu Val Glu Asn Gln Pro Asp Val
                130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175
```

```
Asn Val Asn Asn Ala Val Asn Thr Leu Val Glu Arg Trp Asn Glu Lys
                180                 185                 190

Tyr Ala Gln Ala Tyr Pro Asn Val Ser Ala Lys Ile Asp Tyr Asp Asp
            195                 200                 205

Glu Met Ala Tyr Ser Glu Ser Gln Leu Ile Ala Lys Phe Gly Thr Ala
        210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
        290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Lys Ser Lys Leu Ala His Phe
450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu

<210> SEQ ID NO 18
<211> LENGTH: 25
<212> TYPE: DNA
<213> ORGANISM: Artificial Sequence
<220> FEATURE:
<223> OTHER INFORMATION: Primer for amplifying E7

<400> SEQUENCE: 18
gcggatccca tggagataca cctac                                    25
```

<210> SEQ ID NO 19
<211> LENGTH: 22
<212> TYPE: DNA
<213> ORGANISM: Artificial Sequence
<220> FEATURE:
<223> OTHER INFORMATION: Primer for amplifying E7

<400> SEQUENCE: 19
gctctagatt atggtttctg ag                                              22

<210> SEQ ID NO 20
<211> LENGTH: 98
<212> TYPE: PRT
<213> ORGANISM: Human papillomavirus type 16

<400> SEQUENCE: 20

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 21
<211> LENGTH: 105
<212> TYPE: PRT
<213> ORGANISM: Human papillomavirus type 16

<400> SEQUENCE: 21

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 22
<211> LENGTH: 158
<212> TYPE: PRT
<213> ORGANISM: Human papillomavirus type 16

<400> SEQUENCE: 22

Met His Gln Lys Arg Thr Ala Met Phe Gln Asp Pro Gln Glu Arg Pro

```
1               5                   10                  15
Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
                35                  40                  45

Val Tyr Asp Phe Ala Phe Arg Asp Leu Cys Ile Val Tyr Arg Asp Gly
            50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
                100                 105                 110

Cys Gln Lys Pro Leu Cys Pro Glu Glu Lys Gln Arg His Leu Asp Lys
                115                 120                 125

Lys Gln Arg Phe His Asn Ile Arg Gly Arg Trp Thr Gly Arg Cys Met
                130                 135                 140

Ser Cys Cys Arg Ser Ser Arg Thr Arg Glu Thr Gln Leu
145                 150                 155

<210> SEQ ID NO 23
<211> LENGTH: 158
<212> TYPE: PRT
<213> ORGANISM: Human papillomavirus type 16

<400> SEQUENCE: 23

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
                35                  40                  45

Phe Lys Asp Leu Phe Val Val Tyr Arg Asp Ser Ile Pro His Ala Ala
            50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
                115                 120                 125

Asn Ile Ala Gly His Tyr Arg Gly Gln Cys His Ser Cys Cys Asn Arg
                130                 135                 140

Ala Arg Gln Glu Arg Leu Gln Arg Arg Glu Thr Gln Val
145                 150                 155

<210> SEQ ID NO 24
<211> LENGTH: 9
<212> TYPE: PRT
<213> ORGANISM: Human immunodeficiency virus

<400> SEQUENCE: 24

Ala Met Gln Met Leu Lys Glu Thr Ile
1               5
```

```
<210> SEQ ID NO 25
<211> LENGTH: 9
<212> TYPE: PRT
<213> ORGANISM: Listeria monocytogenes

<400> SEQUENCE: 25

Gly Tyr Lys Asp Gly Asn Glu Tyr Ile
1               5
```